(12) United States Patent
McGrath et al.

(10) Patent No.: US 12,188,899 B2
(45) Date of Patent: Jan. 7, 2025

(54) SENSING COMPOSITIONS, METHODS, AND DEVICES FOR THE DETECTION OF MOLECULES USING A NANOPORE DEVICE

(71) Applicant: Ontera Inc., Santa Cruz, CA (US)

(72) Inventors: Denise Ann McGrath, Scotts Valley, CA (US); Tyler Daniel Shropshire, Santa Cruz, CA (US); Andrew Martin Smith, Santa Cruz, CA (US)

(73) Assignee: Oxford Nanopore Technologies plc, Oxford (GB)

( * ) Notice: Subject to any disclaimer, the term of this patent is extended or adjusted under 35 U.S.C. 154(b) by 693 days.

(21) Appl. No.: 17/274,159

(22) PCT Filed: Sep. 6, 2019

(86) PCT No.: PCT/US2019/050087
§ 371 (c)(1),
(2) Date: Mar. 5, 2021

(87) PCT Pub. No.: WO2020/068400
PCT Pub. Date: Apr. 2, 2020

(65) Prior Publication Data
US 2021/0310988 A1 Oct. 7, 2021

Related U.S. Application Data

(60) Provisional application No. 62/728,584, filed on Sep. 7, 2018, provisional application No. 62/728,672, filed on Sep. 7, 2018.

(51) Int. Cl.
*G01N 27/327* (2006.01)
*C12Q 1/6806* (2018.01)
*G01N 27/447* (2006.01)

(52) U.S. Cl.
CPC ..... *G01N 27/44747* (2013.01); *C12Q 1/6806* (2013.01)

(58) Field of Classification Search
CPC ....... G01N 27/44747; G01N 33/48721; C12Q 1/5806
See application file for complete search history.

(56) References Cited

U.S. PATENT DOCUMENTS

| 9,104,774 B2 | 8/2015 | Falkenberg et al. |
| 9,670,526 B2 | 6/2017 | Kokoris et al. |
| 2012/0193231 A1* | 8/2012 | Afzali-Ardakani .......... C12Q 1/6869 204/601 |

(Continued)

FOREIGN PATENT DOCUMENTS

| CN | 102725407 A | 10/2012 |
| CN | 13717749 A | 4/2014 |

(Continued)

OTHER PUBLICATIONS

Harrer et al., "Electrochemical Characterization of Thin Film Electrodes Toward Developing a DNA Transistor," Langmuir 2010, 26(24), 19191-19198 (Year: 2010).*

(Continued)

*Primary Examiner* — Alexander S Noguerola
(74) *Attorney, Agent, or Firm* — Fenwick & West LLP

(57) ABSTRACT

The invention relates to compositions, methods, devices, systems, and kits for detecting and characterizing molecules using a nanopore device.

42 Claims, 43 Drawing Sheets

(56) References Cited

U.S. PATENT DOCUMENTS

| | | |
|---|---|---|
| 2016/0200773 A1 | 7/2016 | Morin |
| 2017/0168040 A1 | 6/2017 | Turner et al. |
| 2017/0369944 A1* | 12/2017 | Barrall ............. G01N 33/48721 |

FOREIGN PATENT DOCUMENTS

| | | | |
|---|---|---|---|
| CN | 104254771 A | 12/2014 | |
| CN | 107533045 A | 1/2018 | |
| CN | 108333358 A | 7/2018 | |
| WO | WO 0242496 A2 * | 5/2002 | ............... C12Q 1/68 |
| WO | WO 2012/149042 A2 | 11/2012 | |

OTHER PUBLICATIONS

ThermoFisher product description of polyethylene glycol 300 (Year: 2023).*

CosmEthics online article entitled "Everything you need to know about PEG family", 2014 (Year: 2014).*

Harrer et al., "Electrochemical Protection of Thin Film Electrodes in Solid State Nanopores," Nanotechnology Jul. 8, 2011; 22(27): 275304. doi:10.1088/0957-4484/22/27/275304 (Year: 2011).*

Ermann et al., "Promoting single-file DNA translocations through nanopores using electro-osmotic flow," The Journal of Chemical Physics 149, 163311 (2018) (Year: 2018).*

PCT International Search Report and Written Opinion, PCT/US2019/050087, Jun. 2, 2020, 18 Pages.

Fologea, D. et al., "Detecting Single Stranded DNA with a Solid State Nanopore," Nano Letters, vol. 5, No. 10, Aug. 31, 2005, pp. 1905-1909.

Kowalczyk, S.W. et al., "Slowing down DNA Translocation through a Nanopore in Lithium Chloride," Nano Letters, vol. 12, Jan. 9, 2012, pp. 1038-1044.

Li, J. et al., "The distribution of DNA translocation times in solid-state nanopores," Journal of Physics: Condensed Matter, vol. 22, Oct. 29, 2010, pp. 1-8.

Wang, V. et al., "Current enhancement in solid-state nanopores depends on three-dimensional DNA structure," arXiv:1905.13432v1, May 31, 2019, pp. 1-18.

* cited by examiner

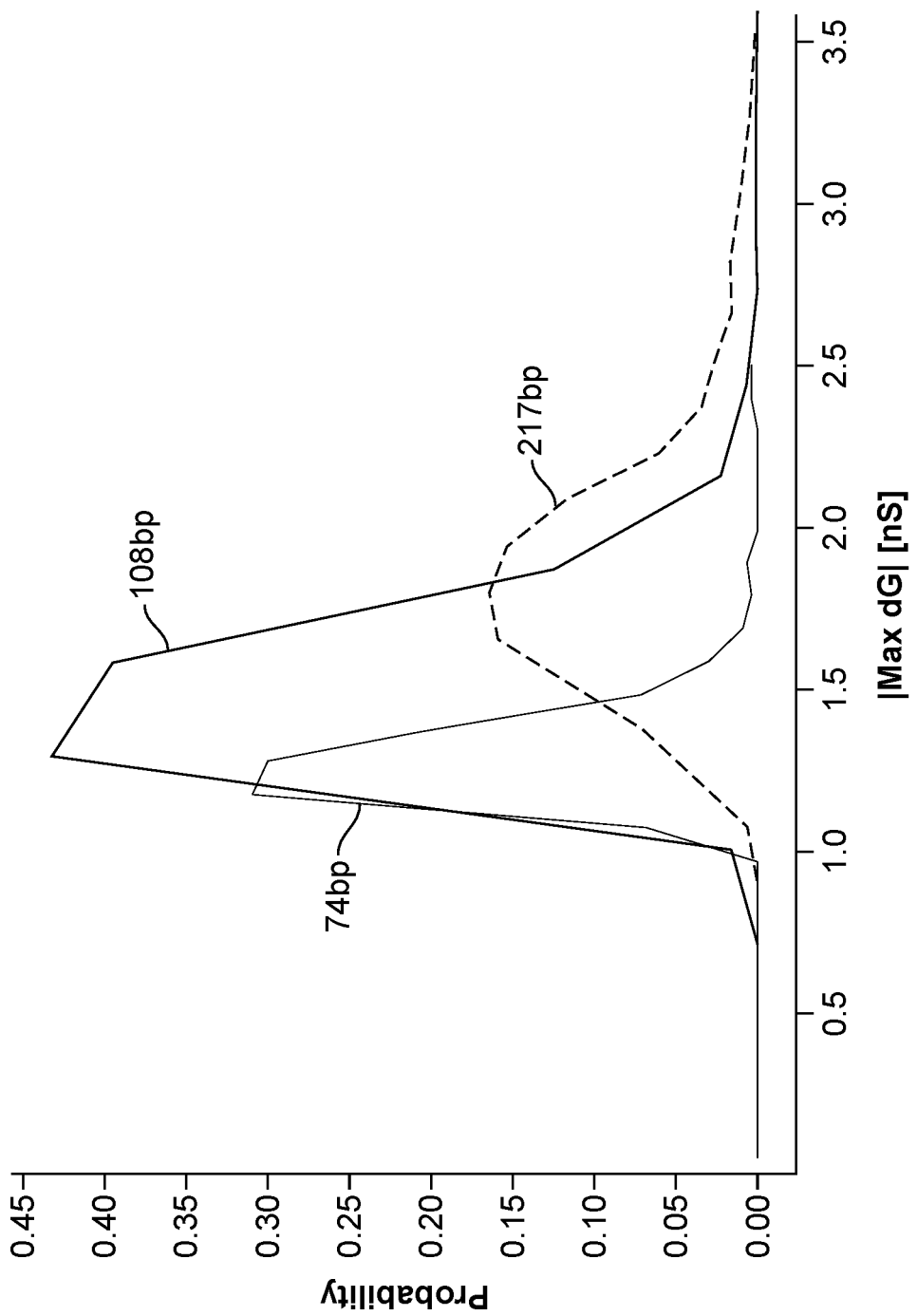

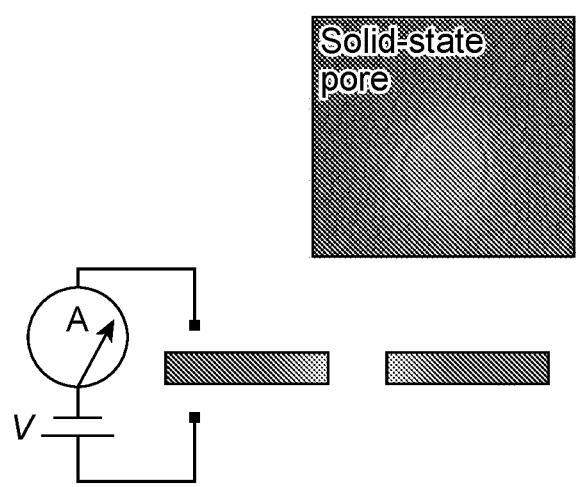
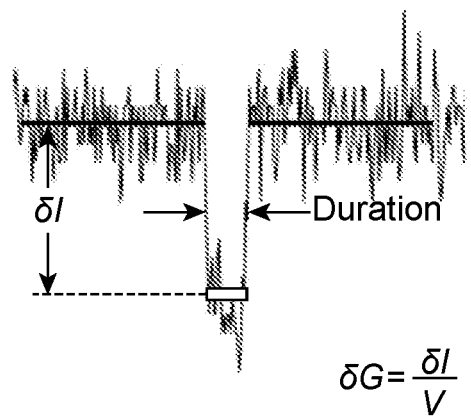
FIG. 7A        FIG. 7B
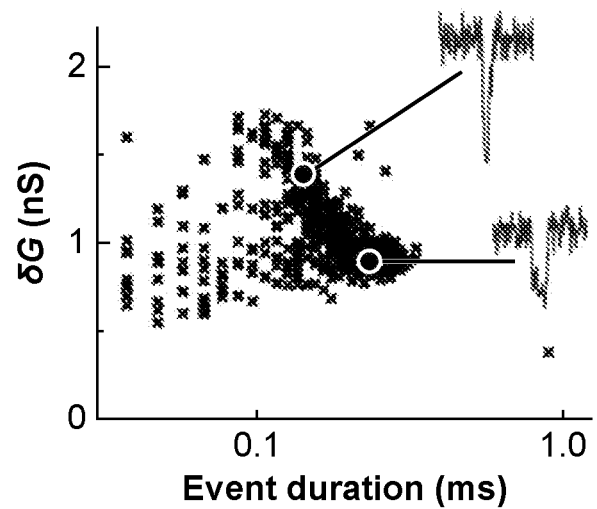
FIG. 7C

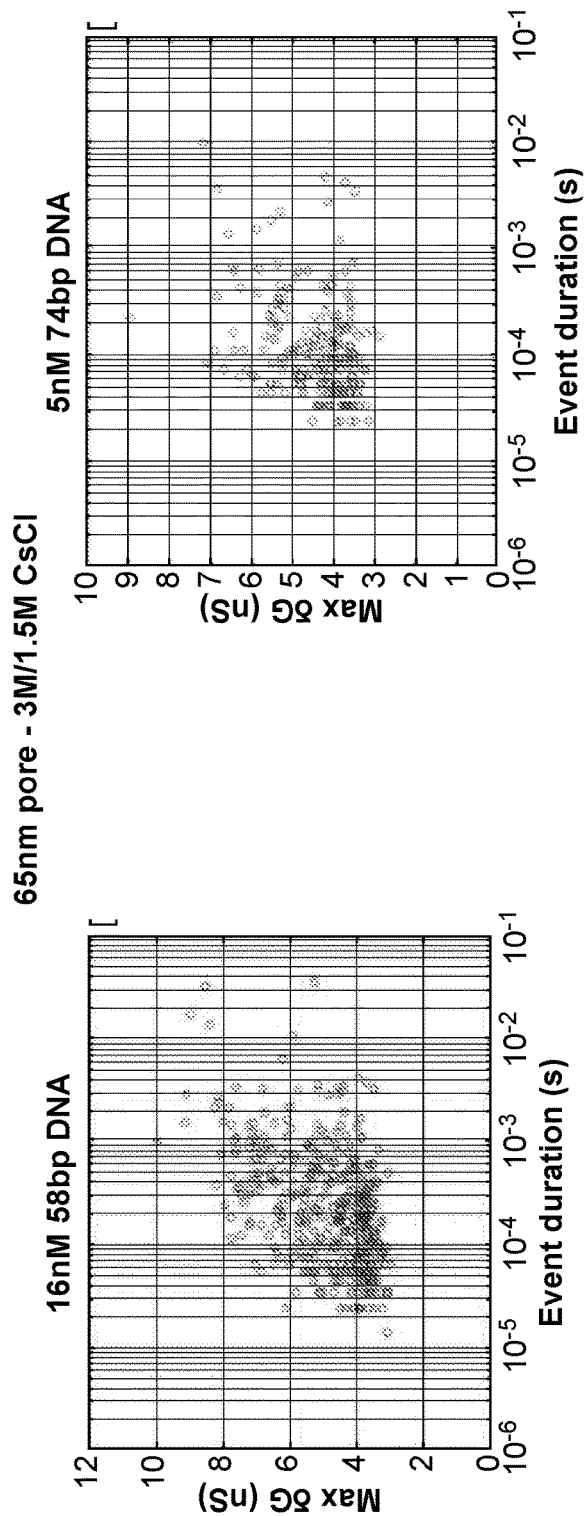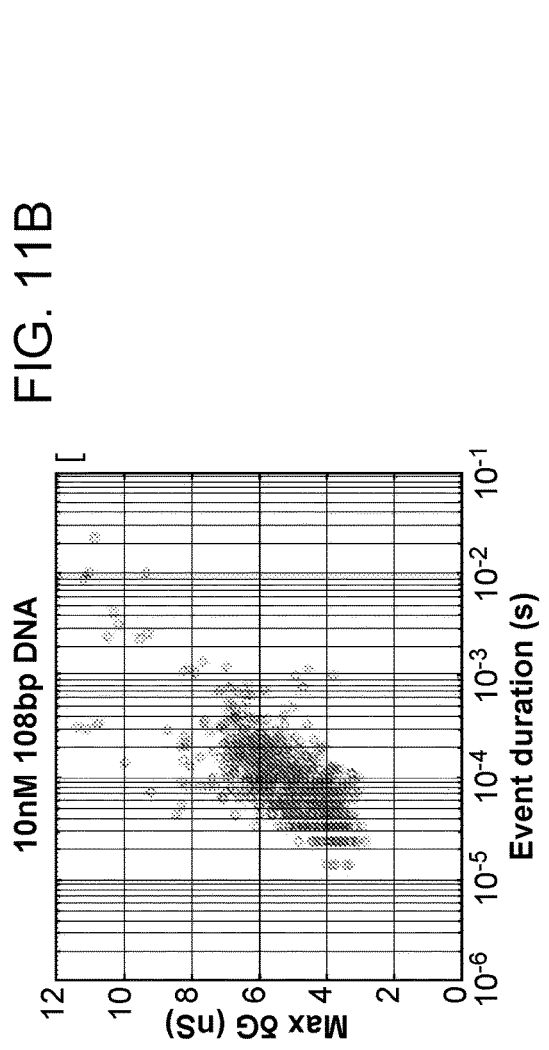
FIG. 11A
FIG. 11B
FIG. 11C

Pore = 25-26nm

*3M/1.5M CsCl

*3M/1.5M CsCl

SENSING COMPOSITIONS, METHODS, AND DEVICES FOR THE DETECTION OF MOLECULES USING A NANOPORE DEVICE

1. CROSS-REFERENCE TO RELATED APPLICATIONS

This application is a national phase of International Application No. PCT/US2019/050087, titled "Sensing Compositions, Methods, and Devices for the Detection of Molecules Using a Nanopore Device." filed on Sep. 6, 2019, which claims the priority under 35 U.S.C. 119(e) of U.S. Provisional Application Nos. 62/728,672 filed on Sep. 7, 2018, and 62/728,584 filed on Sep. 7, 2018, each of which is hereby incorporated by reference in its entirety

2. BACKGROUND

Nanopore devices are versatile devices that use a porous membrane (e.g., single or arrayed pores) for the detection and quantification of single biomolecules in a solution, such as proteins, DNA, and viral particles. The interplay between friction (e.g., viscosity), electrophoretic force and thermal motions imposes limits on biomolecule detection and resolution.

An ongoing challenge in the field of nanopore detection is to develop better sensing techniques that can detect and resolve with better accuracy, the characteristics of biomolecules in a sample that may have similar physical properties to one another such as charge, size, concentration, or structural conformation.

3. SUMMARY

While researching nanopore detection methods we discovered that polyether agents of a generally smaller size or molecular weight facilitate the detection of target molecules passing through pores of a nanopore device. This discovery provides for increase accuracy in the detection or resolution of particular analytes and biomolecules in a nanopore device that could not be previously be detected or resolved using conventional nanopore buffers.

The disclosure provides compositions, methods, devices, systems, and kits for the detection or characterization of an analyte and biomolecules using a nanopore device. These inventive aspects are particularly useful for detecting and resolving biomolecule analytes that have similar physical characteristics, such as length, charge, concentration, and/or structure, and would otherwise not be easily detected, resolved from one another, or capable of characterization.

The compositions, methods, systems, and kits of the disclosure are useful in any application that requires accurate identification of biomolecules. Such applications include, diagnostics for biomarker testing, infectious disease testing, genetic screening (e.g., the identification of genetic locus, inserted transgenes (e.g., genetically modified organisms), copy number, or mutation), and drug or chemical agent screening.

The various inventive aspects are based, at least in part, on the discovery that certain agents when utilized in sensing solutions can facilitate sensitive detection of current signals upon translocation of target analyte molecules through a nanopore of the nanoporous membrane.

The disclosure provides various polyether agent containing sensing solution compositions for detection or characterization of a biomolecule in a sample. The polyether agents can be polymers of 50 monomeric units or less, where the monomeric units can be alkoxy or substituted alkoxy units containing an oxygen atom and a C(2-4) alkyl or substituted C(2-4) alkyl. In certain cases, the polyether agent is monomeric or dimeric. When multiple monomeric units are linked together they generally form a saturated polyalkylene glycol chain. The chain can have a variety of terminal groups including hydroxy or alkoxy terminal groups. Exemplary polyether agents of interest that are useful in the sensing solutions, device, methods and kits described herein include, but are not limited to, ethylene glycol, (poly)ethylene glycol, propylene glycol, (poly)propylene glycol, butylene glycol, (poly)butylene glycol, substituted versions thereof, and alkylated versions thereof.

The disclosure provides numerous salt agents containing sensing solution compositions for detection or characterization of a biomolecule in a sample. This discovery is particularly useful for facilitating enhanced detection of small molecules in larger nanopores.

The disclosure also provides nanopore devices for detection or characterization of a biomolecule in a sample. Also provided are various methods, systems, and kits for detection or characterization of analytes (e.g., biomolecules) using a nanopore device.

4. BRIEF DESCRIPTION OF THE DRAWINGS

A better understanding of the features and advantages of the disclosure will be obtained by reference to the following detailed description that sets forth illustrative embodiments, in which the principles of the invention are utilized, and the accompanying drawings of which:

Figure 3A:
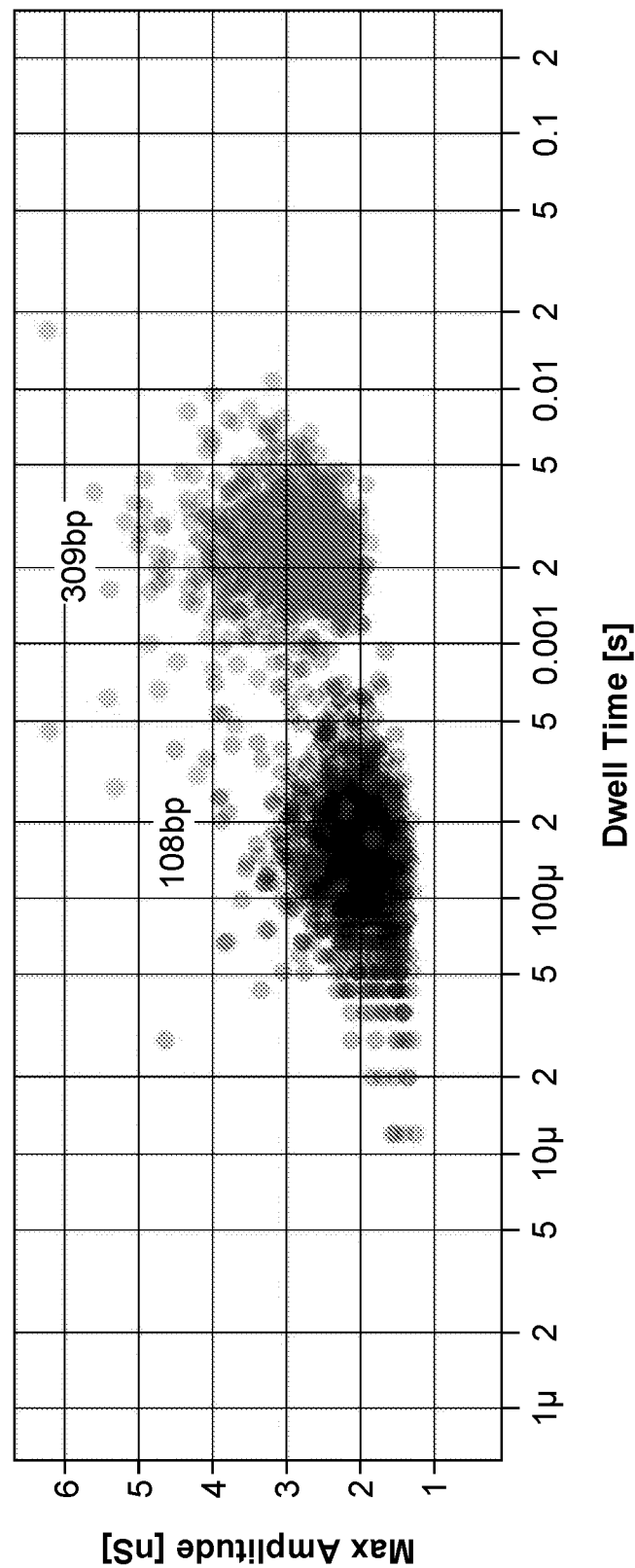
Figure 3B:
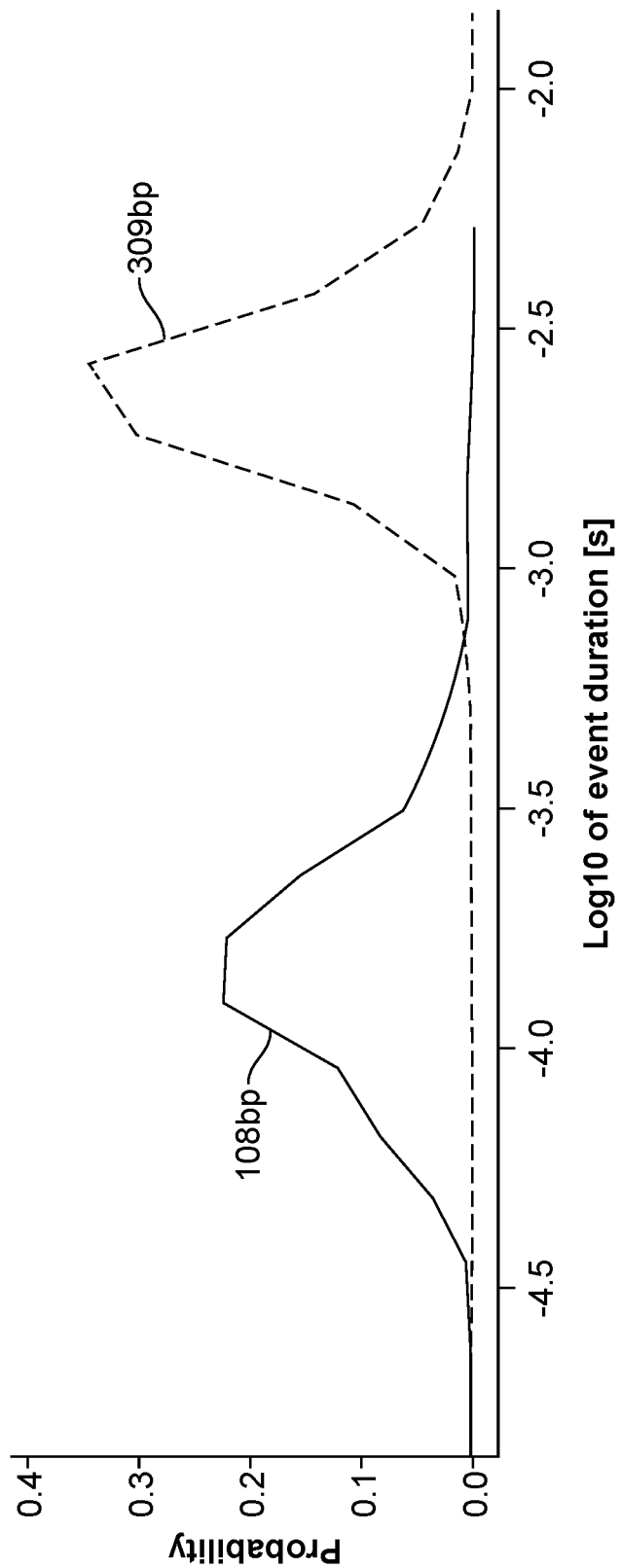
Figure 3C:
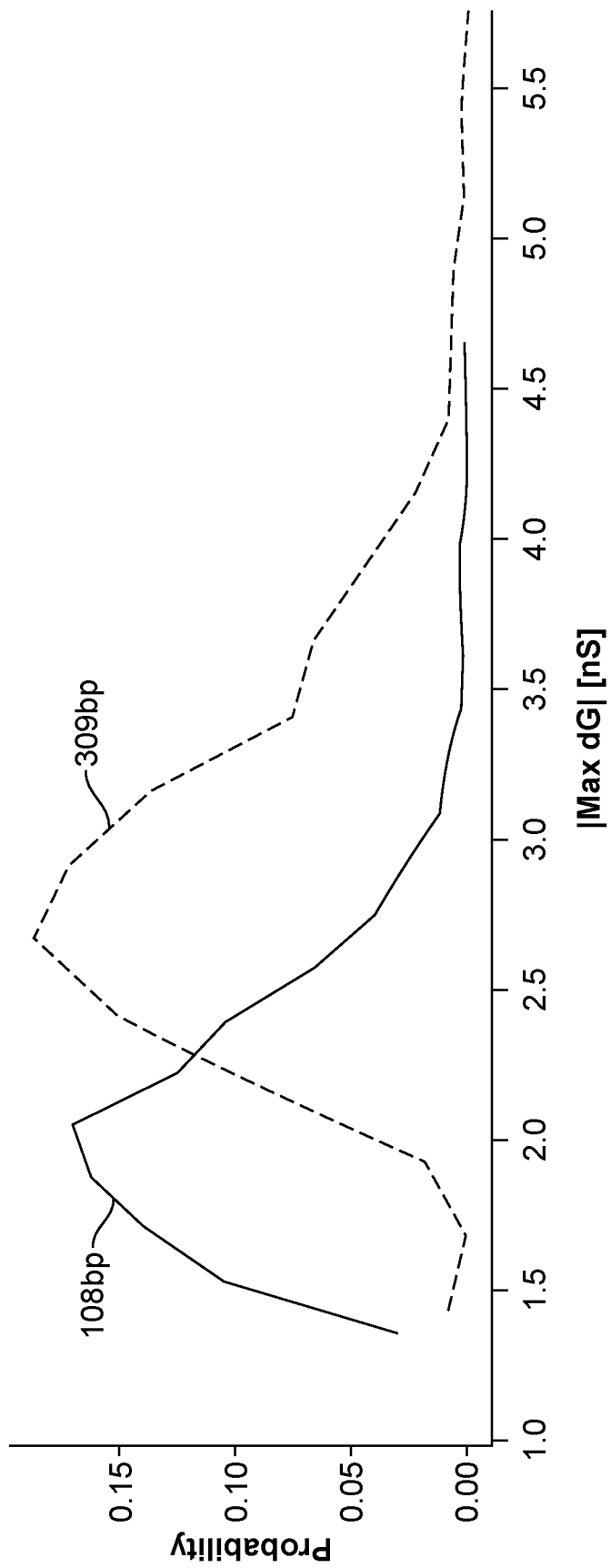

FIGS. 3A-3C show data from a 10% PEG 200 sensing solution. FIG. 3A shows event populations for 108 bp and 309 bp dsDNA. FIG. 3B shows event durations of the 108 bp and 309 bp dsDNA populations on a log scale. FIG. 3C shows the maximum depth of events in each of the 108 bp and 309 bp populations in a histogram.

Figure 4A:
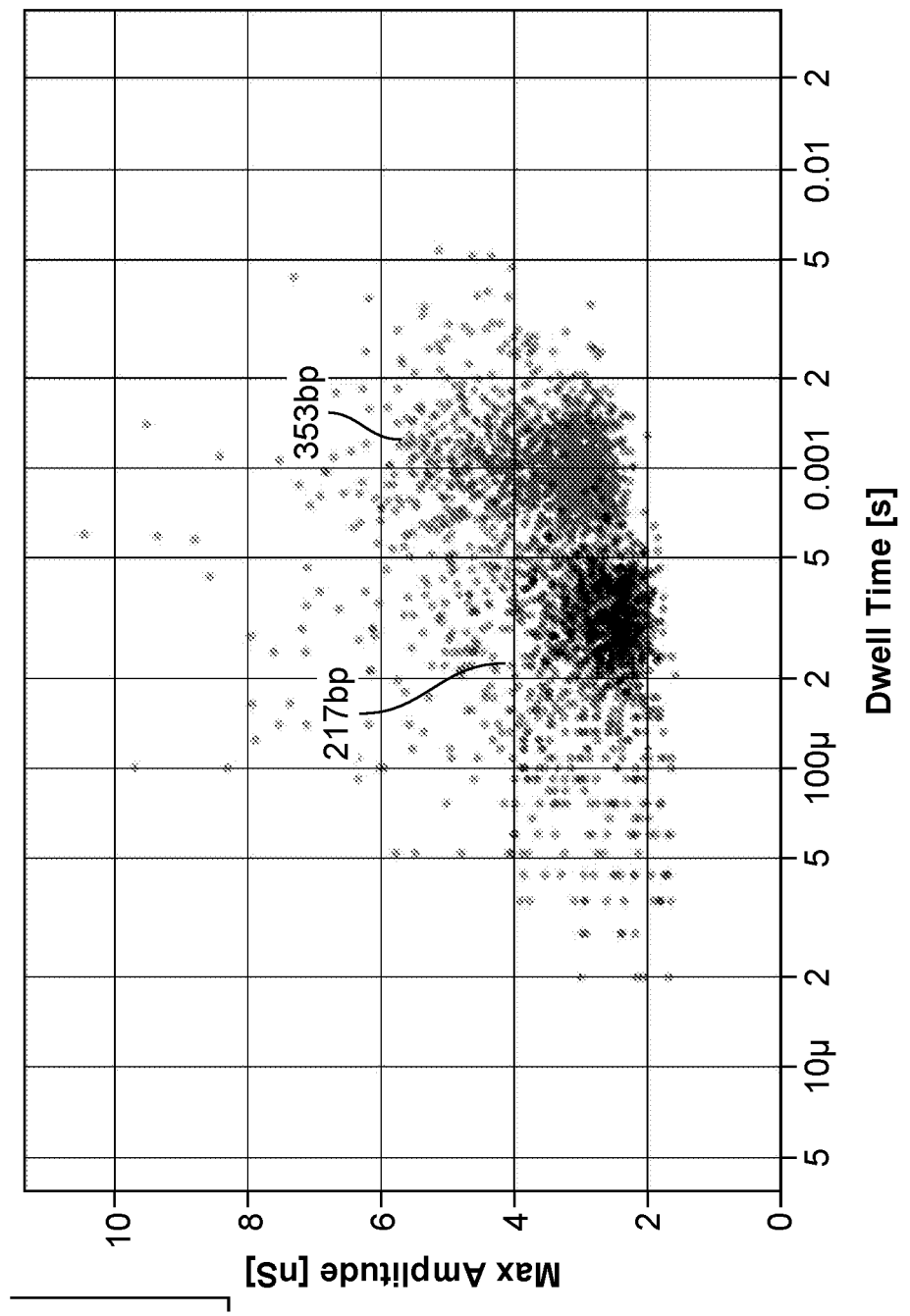
Figure 4B:
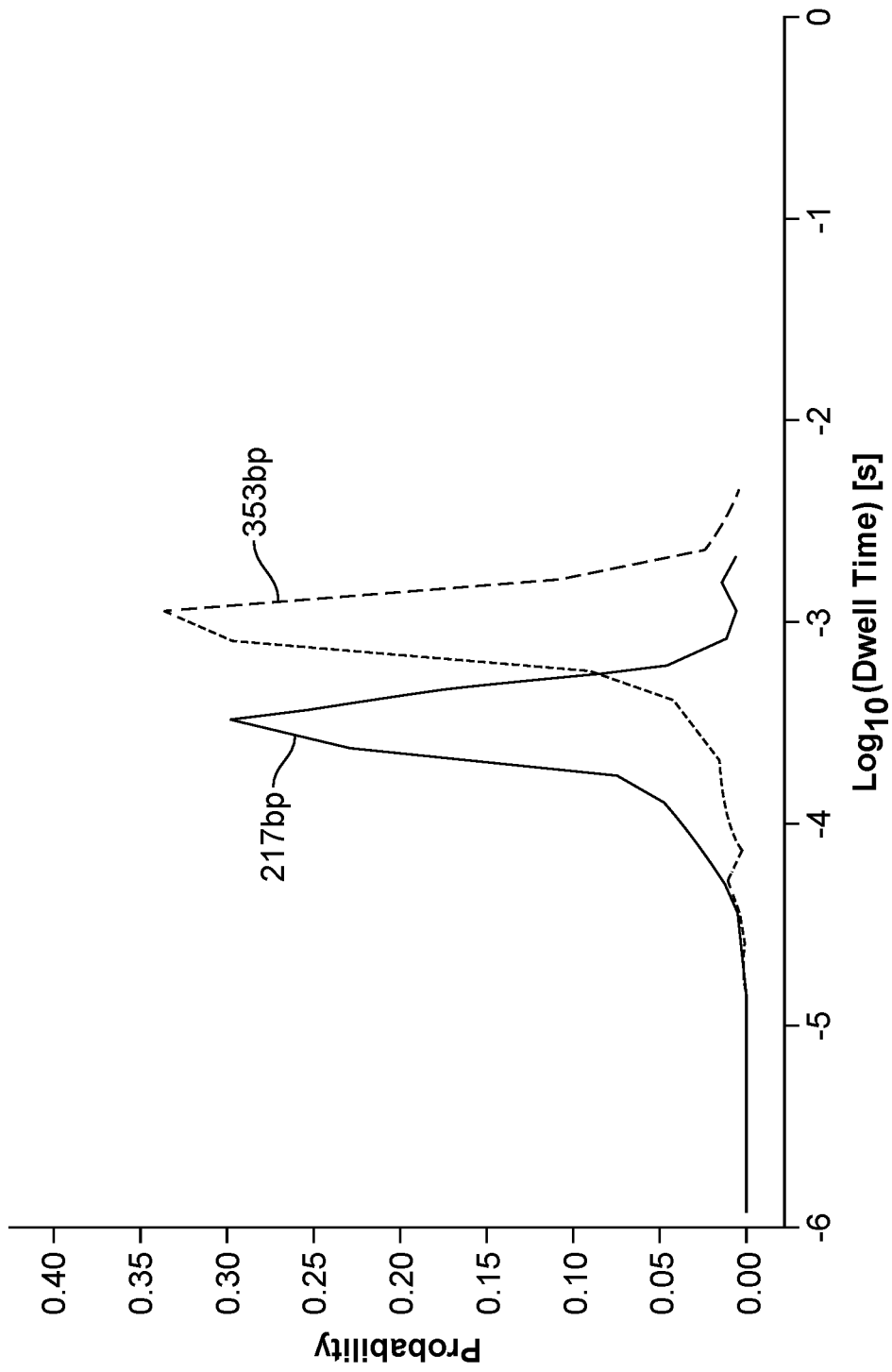
Figure 4C:
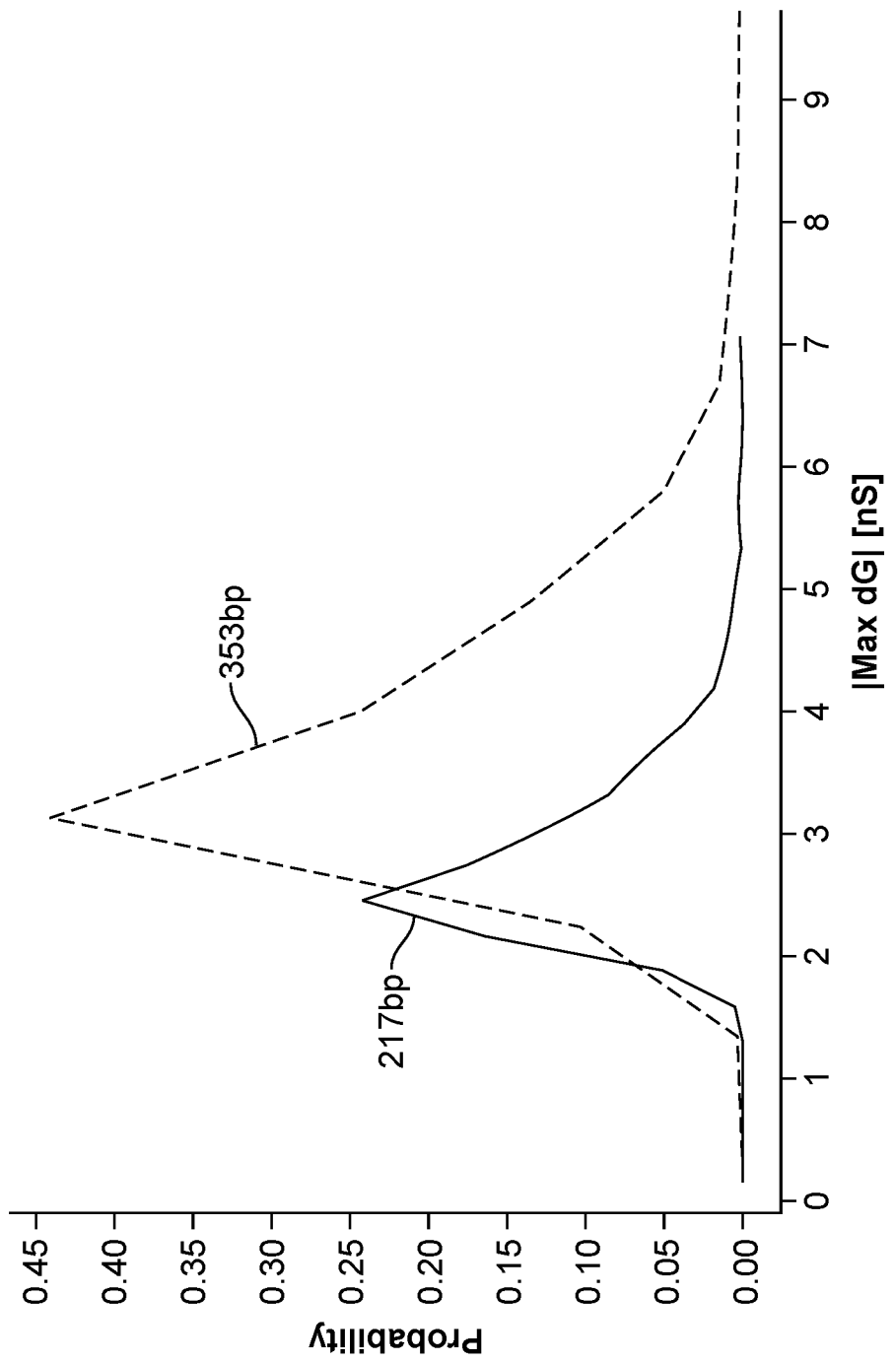
Figure 4D:
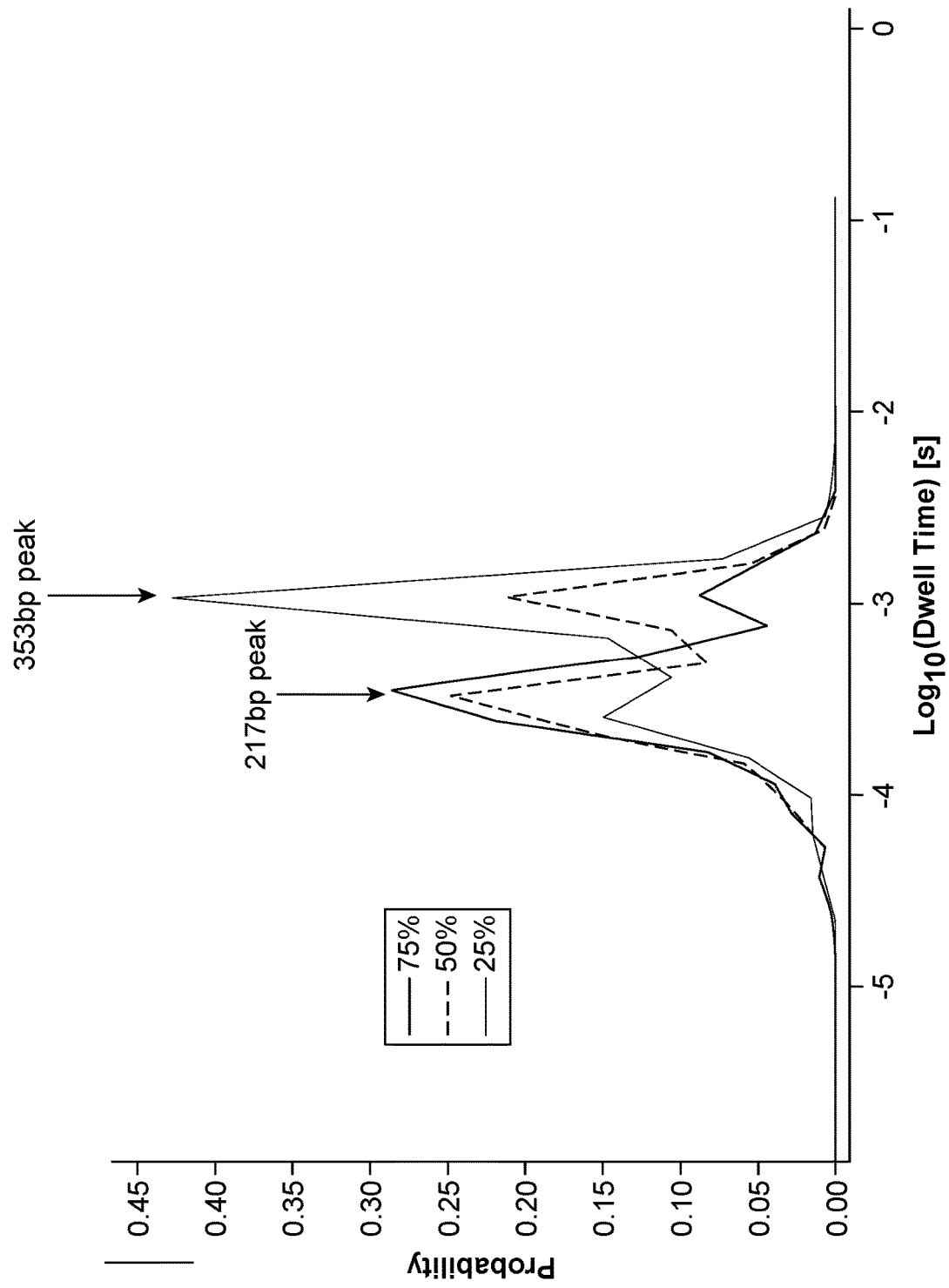
Figure 4E:
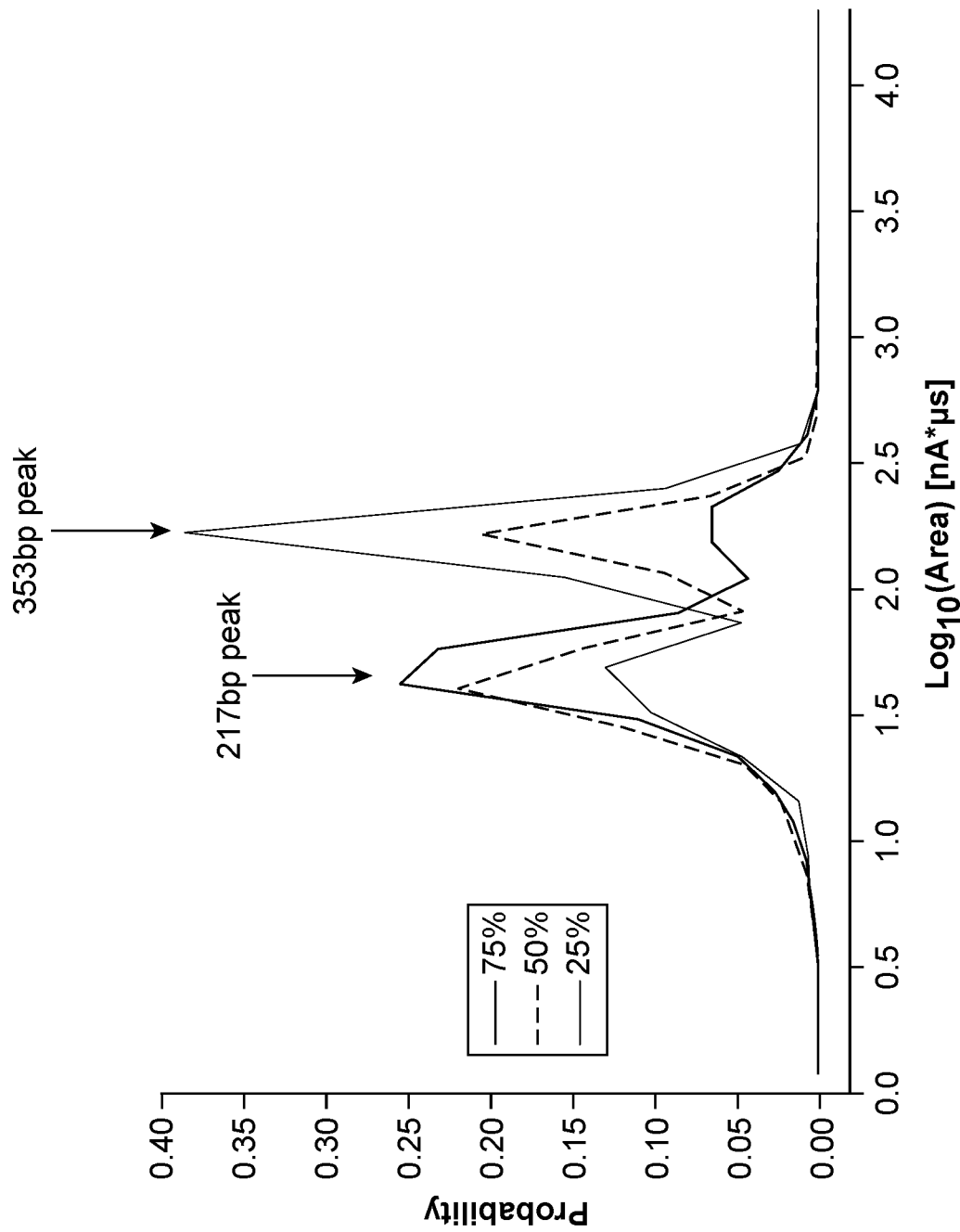

FIGS. 4A-4E show data from a 7% PEG 200 sensing solution. FIG. 4A shows the event plots of 217 bp and 353 bp dsDNA when in isolation. FIG. 4B shows event durations (seconds) of the 217 bp and 353 bp dsDNA populations on a log scale. FIG. 4C shows maximum dG of the 217 bp and 353 bp event populations. FIG. 4D shows a histogram of the dwell times of 25%, 50%, and 75% mixtures of 217 bp with 353 bp dsDNA. FIG. 4E shows a histogram of the event populations from 25%, 50%, and 75% of a 217 bp and a 353 bp dsDNA mixed sample.

Figure 5A:
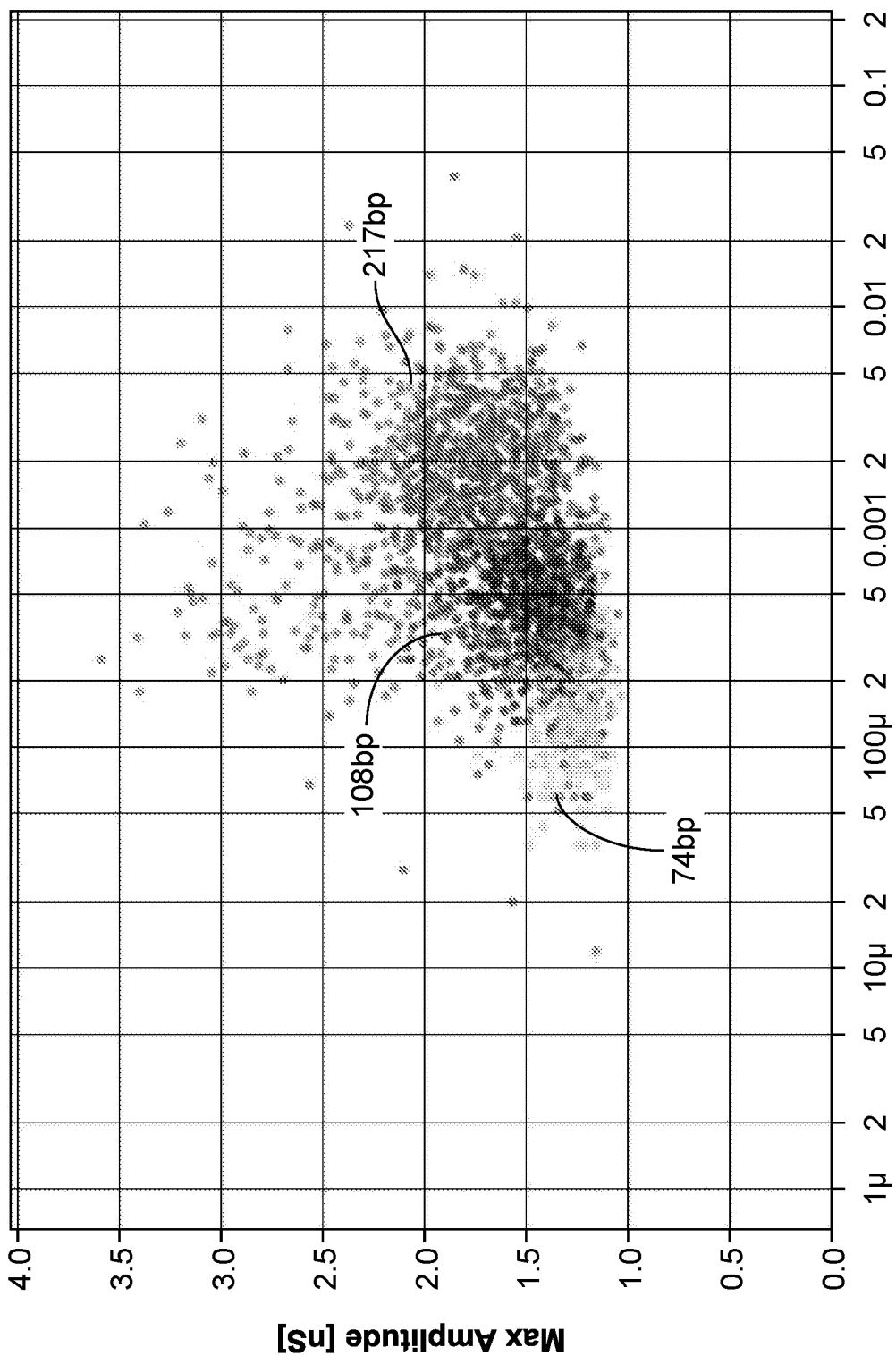
Figure 5B:
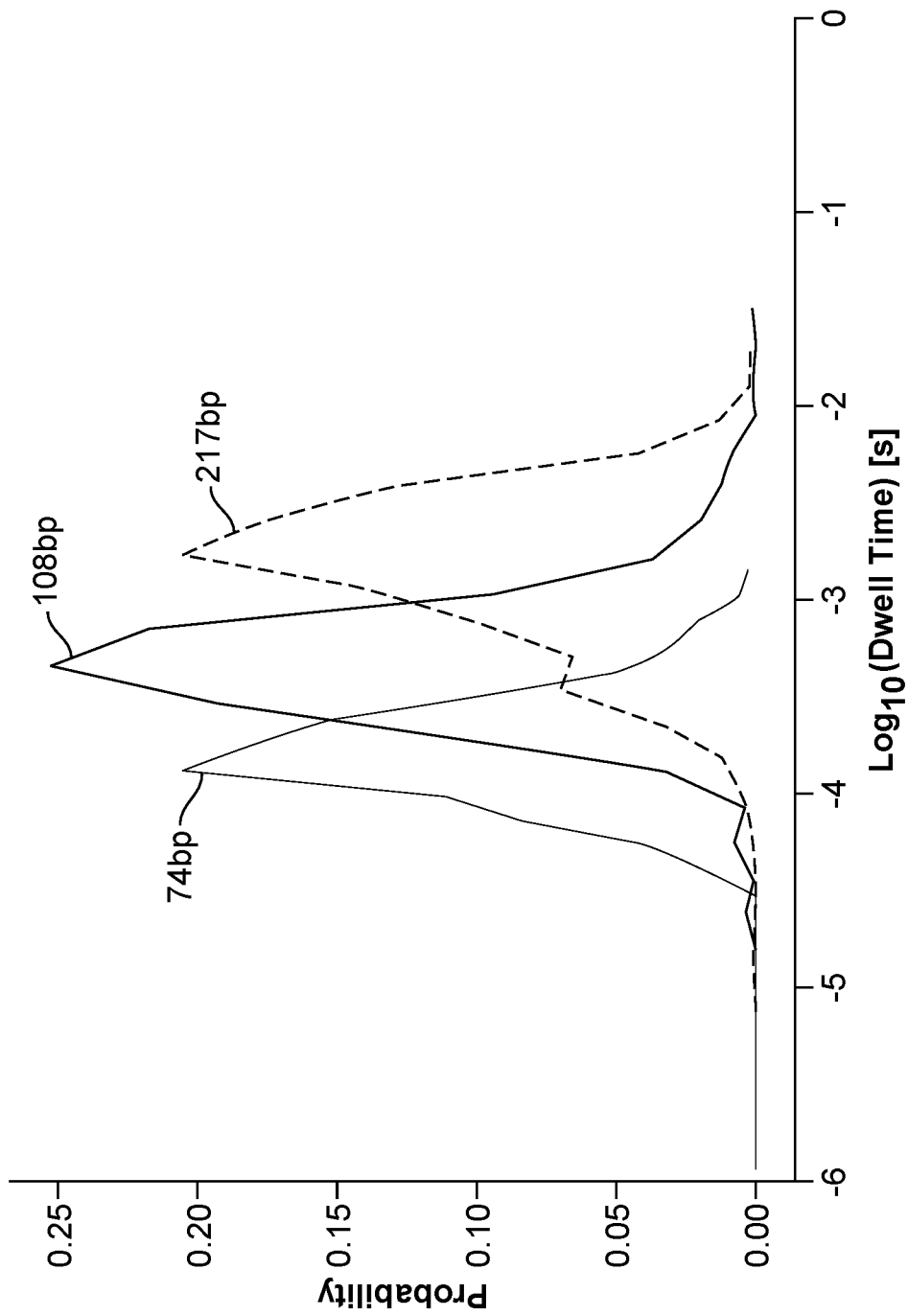
Figure 5D:
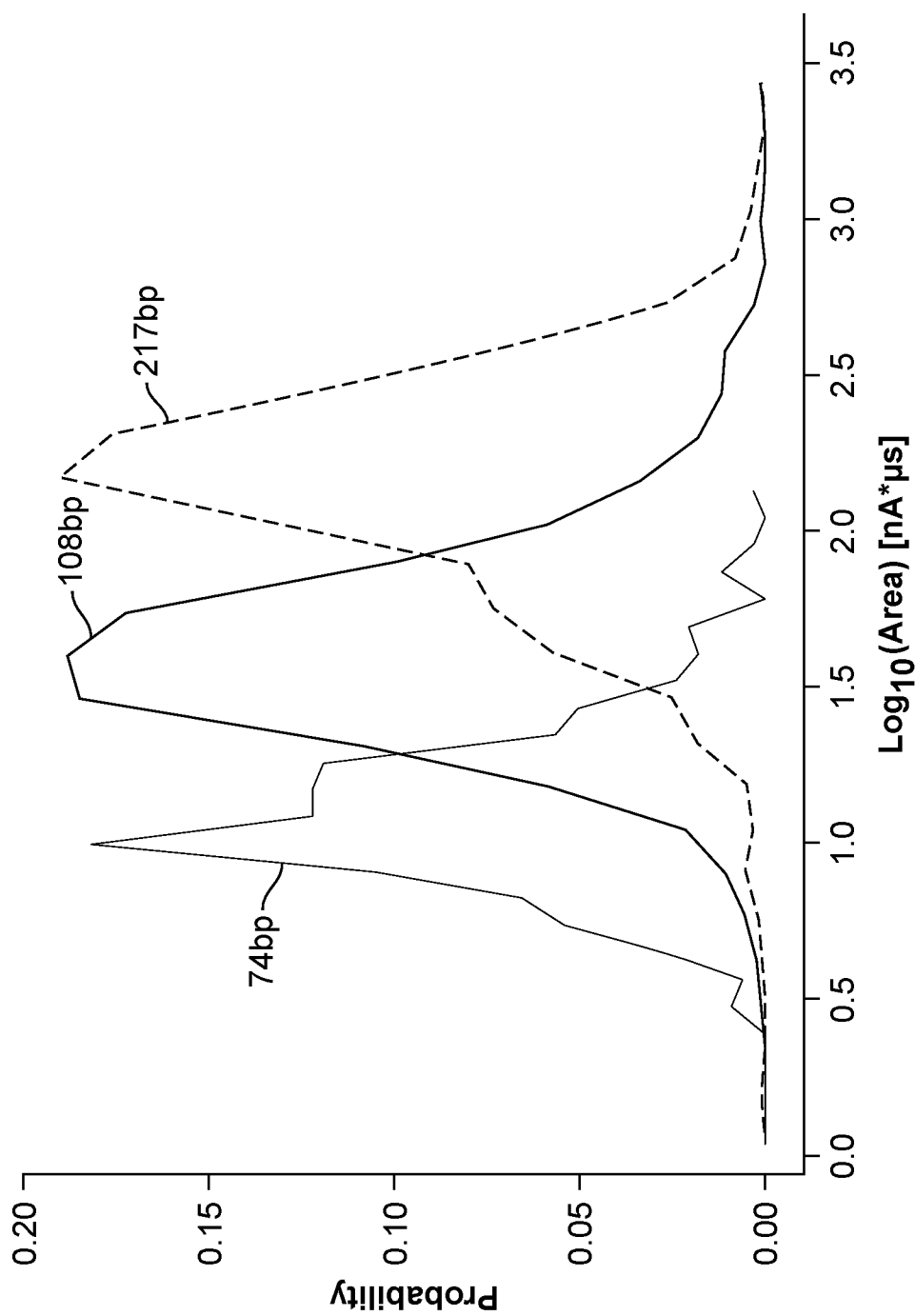

FIGS. 5A-5D show data from a 25% TEG sensing solution. FIG. 5A shows event populations for 74 bp, 108 bp, and 217 bp dsDNA. FIG. 5B shows event population on a log scale (seconds). FIG. 5C shows histograms of the maximum dG signal of each event population. FIG. 5D shows histograms of each event area population on a log scale.

Figure 6A:
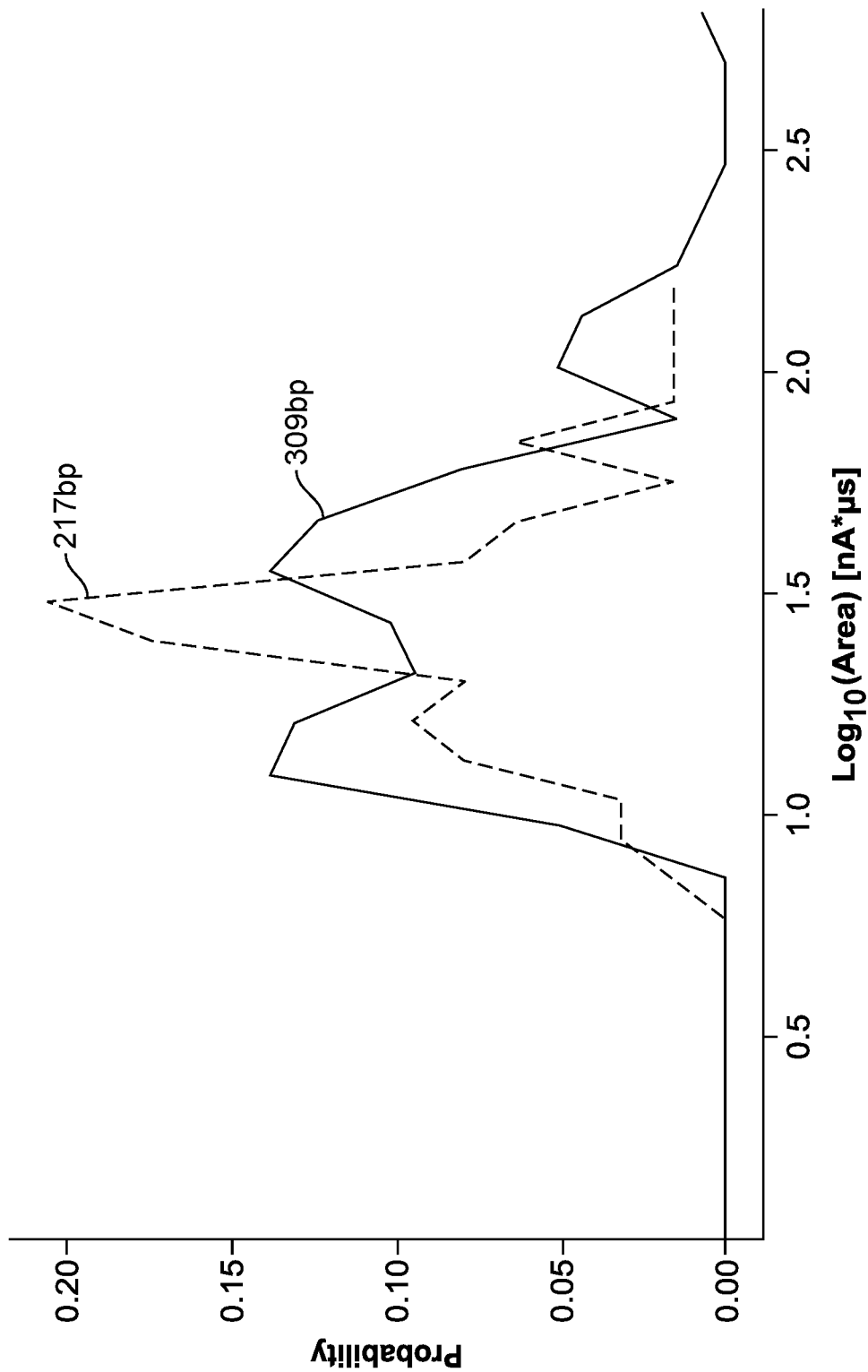
Figure 6B:
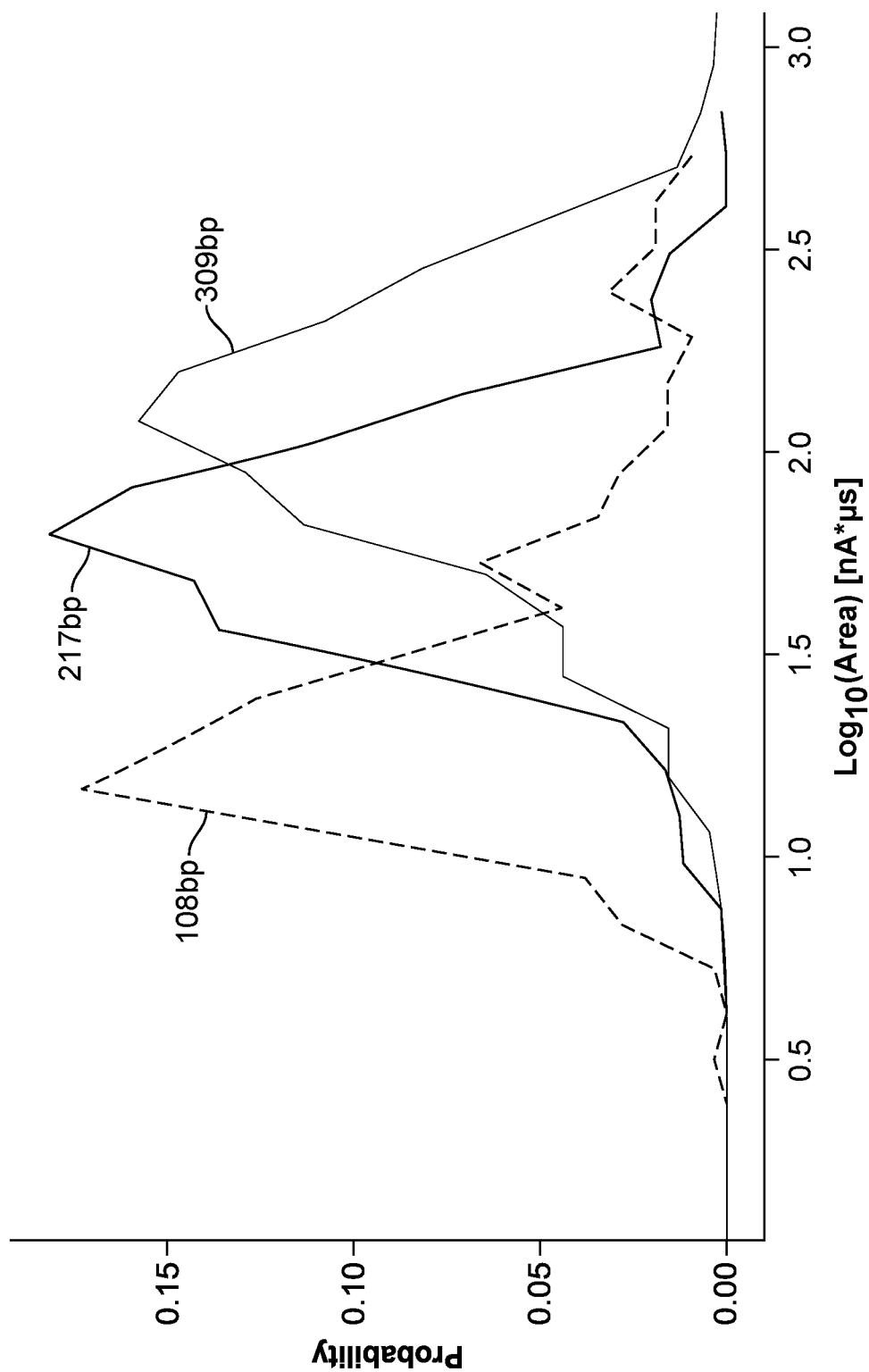

FIGS. 6A-6B show data from a 4M LiCl standard buffer and a 15% TEG sensing solution in a 72 nm nanopore. FIG. 6A shows the event population in a in 4M LiCl buffer for of 217 bp and 309 bp dsDNA. FIG. 6B shows the event area population in a 15% TEG sensing solution for of 217 bp and 309 bp dsDNA.

FIGS. 7A-7C show a schematic diagram of a nanopore device, an example of ionic current detected by such a device during a molecule translocating through a nanopore, and detected events from a 1M LiCl buffer. FIG. 7A shows a schematic diagram of a nanopore with a circuit diagram with electrodes for applying a voltage across the nanopore. FIG. 7B shows a representative event due to translocation of a biomolecule through a pore under an applied voltage. FIG. 7C shows detected events from a 1M LiCl buffer with 27 nm diameter nanopore for a large dsDNA sample, plotted as a function of change in current (6G) and event duration (ms).

Figure 8A:
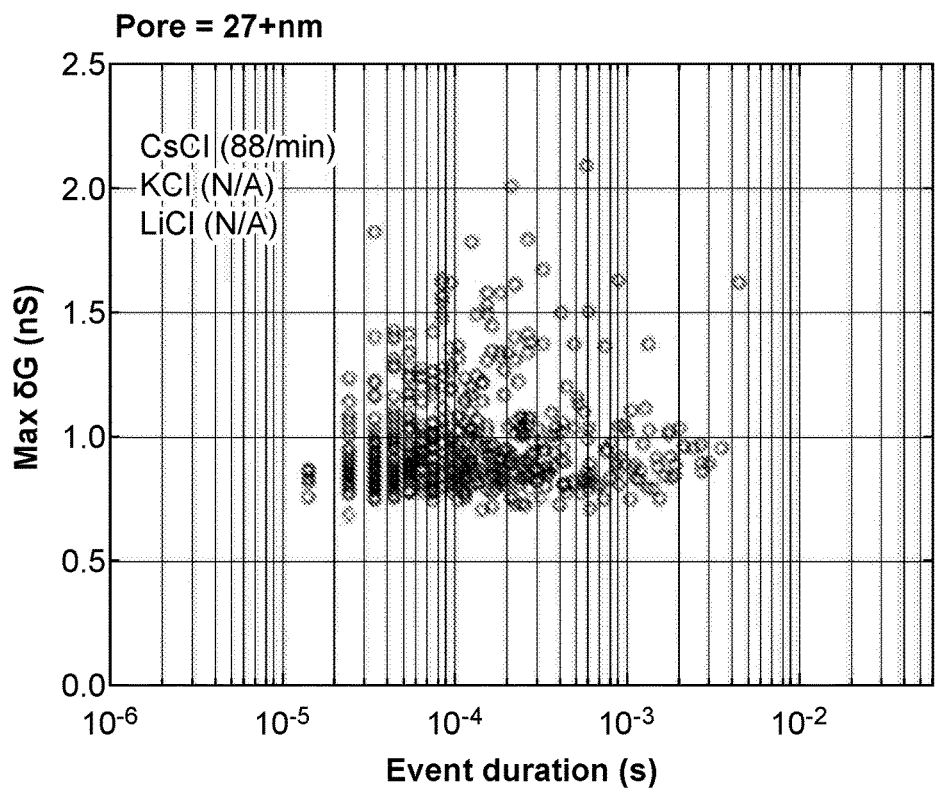
Figure 8B:
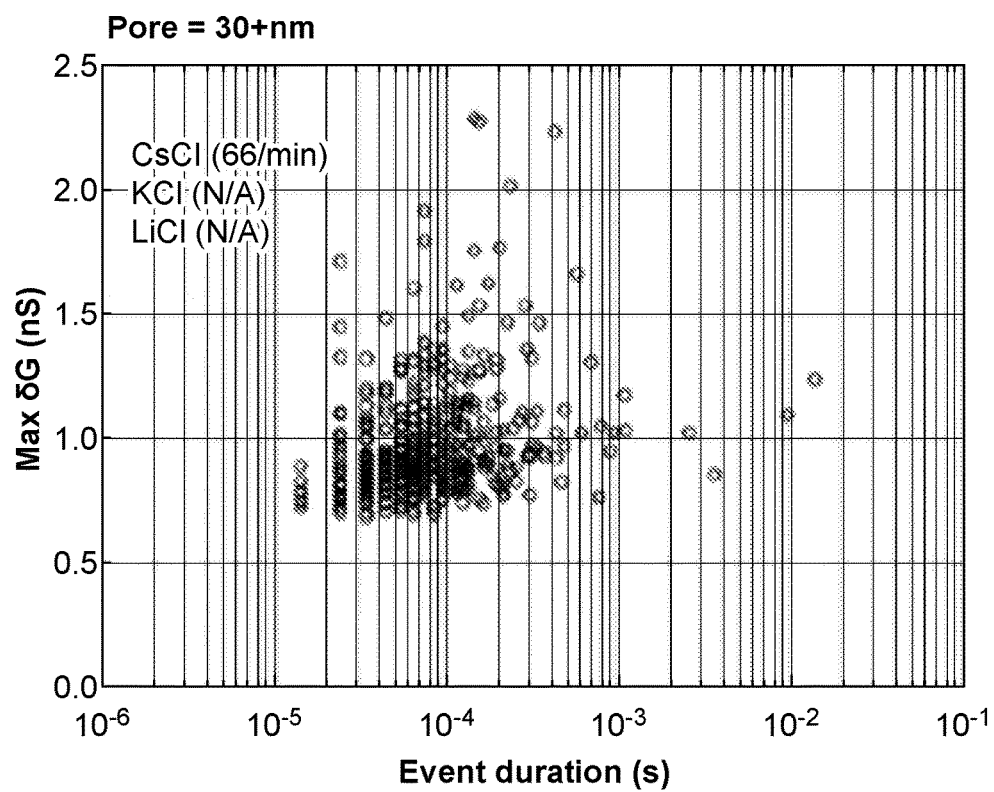

FIGS. 8A-8B show data generated from standard buffers 1M KCl, 1M LiCl, and a 1M CsCl sensing solution. FIG. 8A shows a plot of events detected from a sample with 108 bp dsDNA in a 27 nm diameter nanopore using a CsCl sensing solution. No events were detected in either pore using a KCl or a LiCl buffer. FIG. 8B shows a plot of events detected from a sample with 108 bp dsDNA in a 30 nm diameter nanopore using a CsCl sensing solution. No events were detected in either pore using a KCl or a LiCl buffer.

Figure 9A:
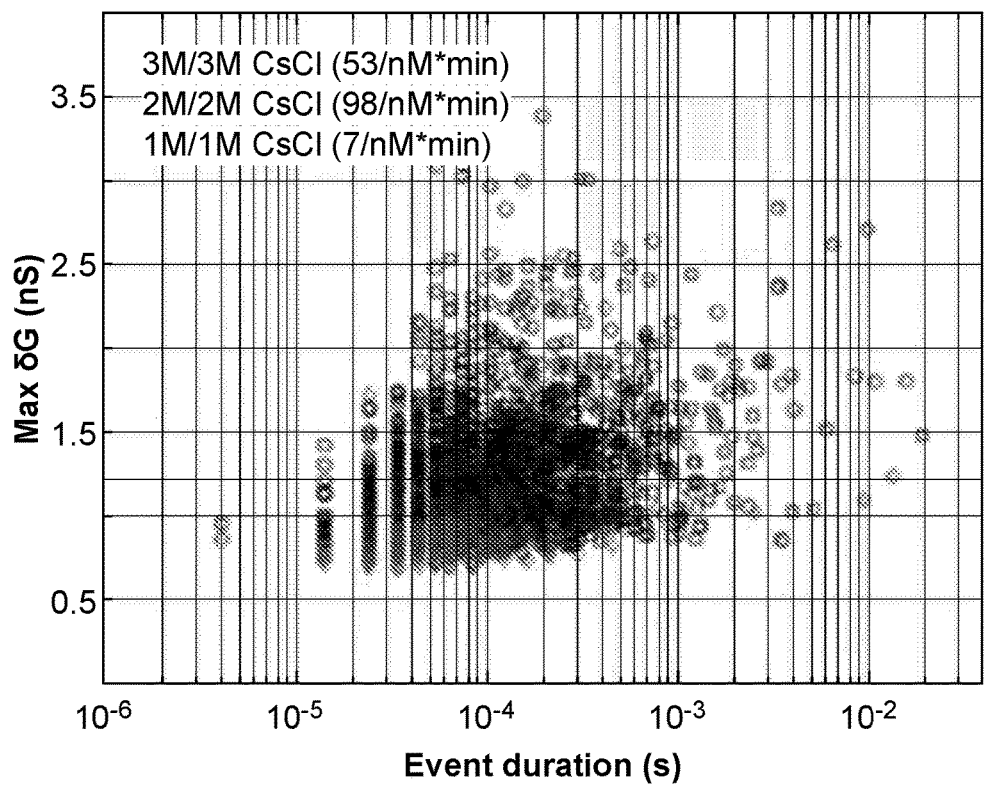
Figure 9B:
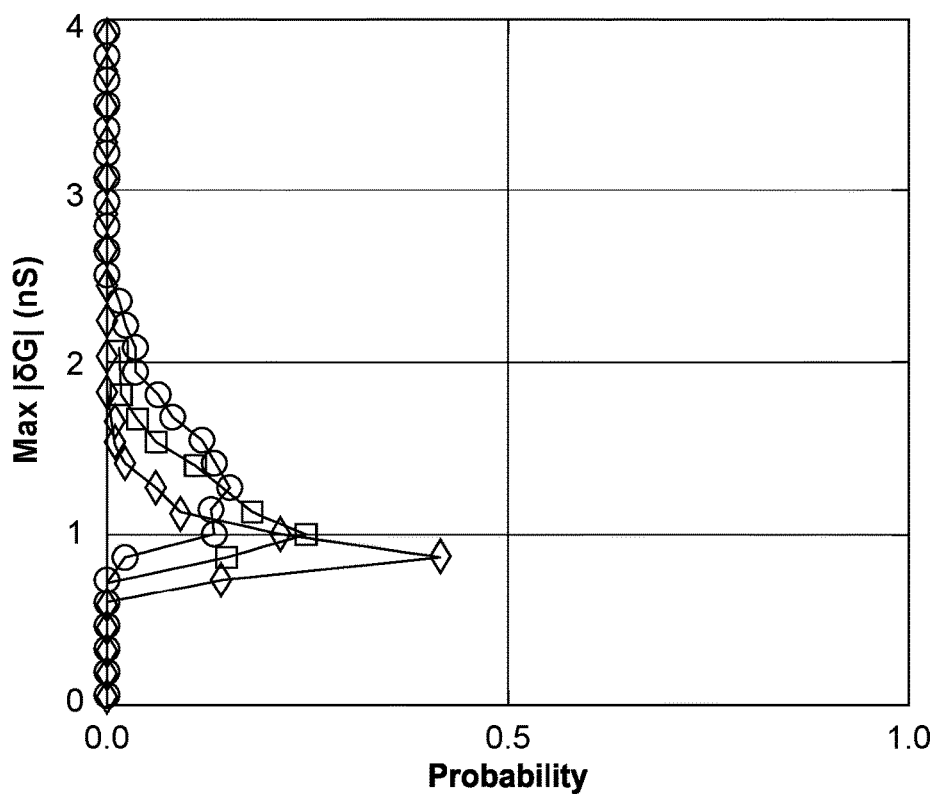

FIGS. 9A-9B show data generated from increasing concentrations of a CsCl sensing solution from 1M to 3M with a 30 nm nanopore. FIG. 9A shows a plot of events detected from a 108 bp dsDNA using a 1M CsCl (diamond), 2M CsCl (square), or 3M CsCl (circle) buffer. FIG. 9B shows a probability histogram for events detected for each buffer based on the change in current (6G).

Figure 10B:
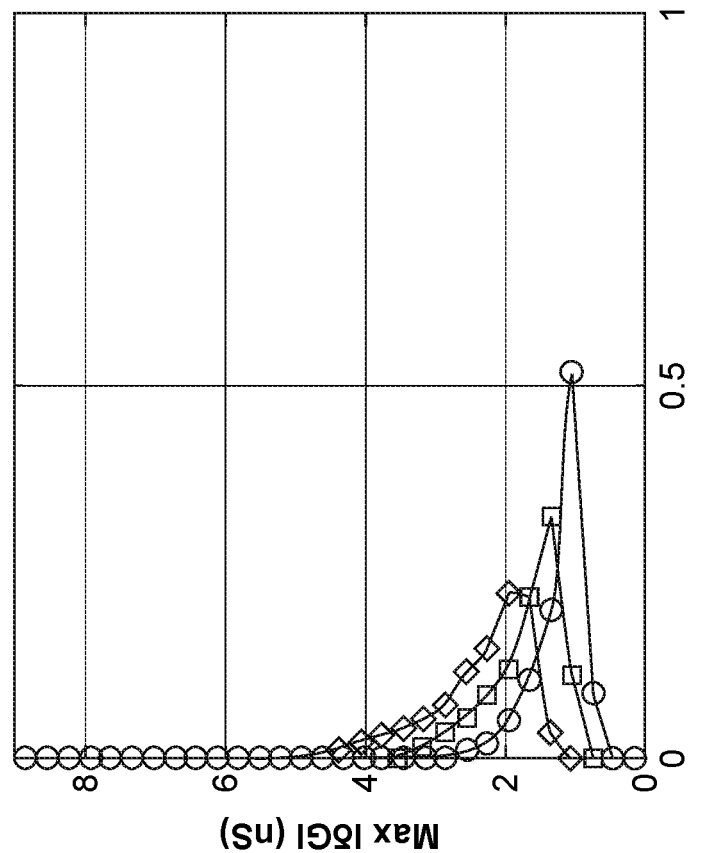
Figure 10A:
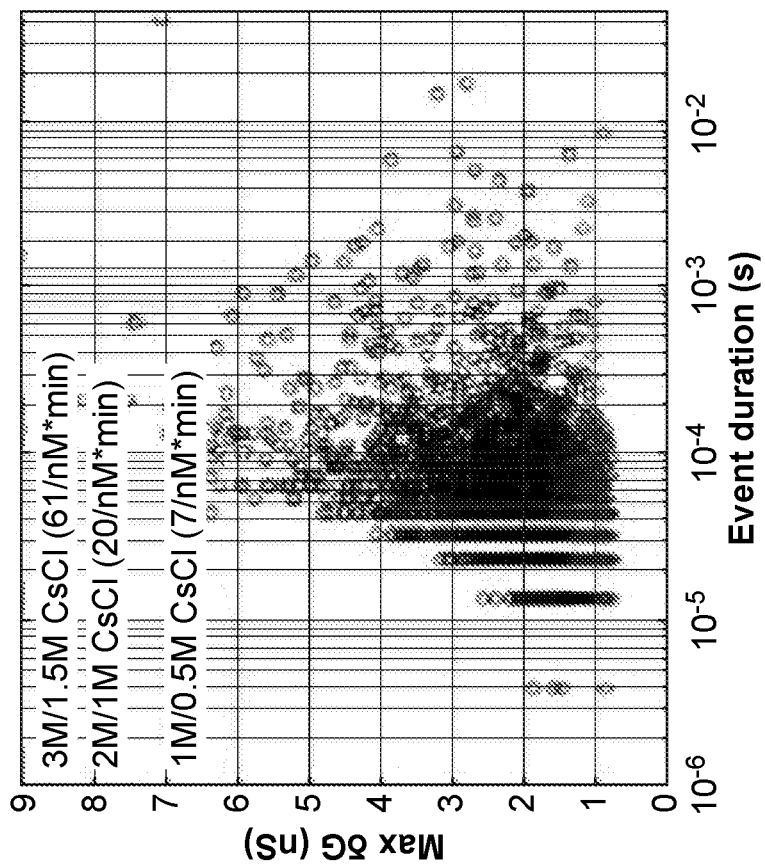

FIGS. 10A-10B shows data generated from CsCl gradient solutions with increasing molarity. FIG. 10A shows a plot of events detected from a 108 bp dsDNA sample in a 30 nm diameter nanopore using a 1M/0.5M CsCl (diamond), 2M/1M CsCl (square), or 3M/1.5M CsCl (circle). FIG. 10B shows a probability histogram for events detected for each CsCl gradient solution based on the change in current (6G).

FIGS. 11A-11C show data generated from a 3M/1.5M CsCl gradient sensing solution with a 65 nm nanopore. FIG. 11A shows a plot of events detected for a 58 bp dsDNA sample. FIG. 11B shows a plot of events detected for a 74 bp dsDNA sample. FIG. 11C shows a plot of events detected for a 108 bp dsDNA sample.

Figure 12:
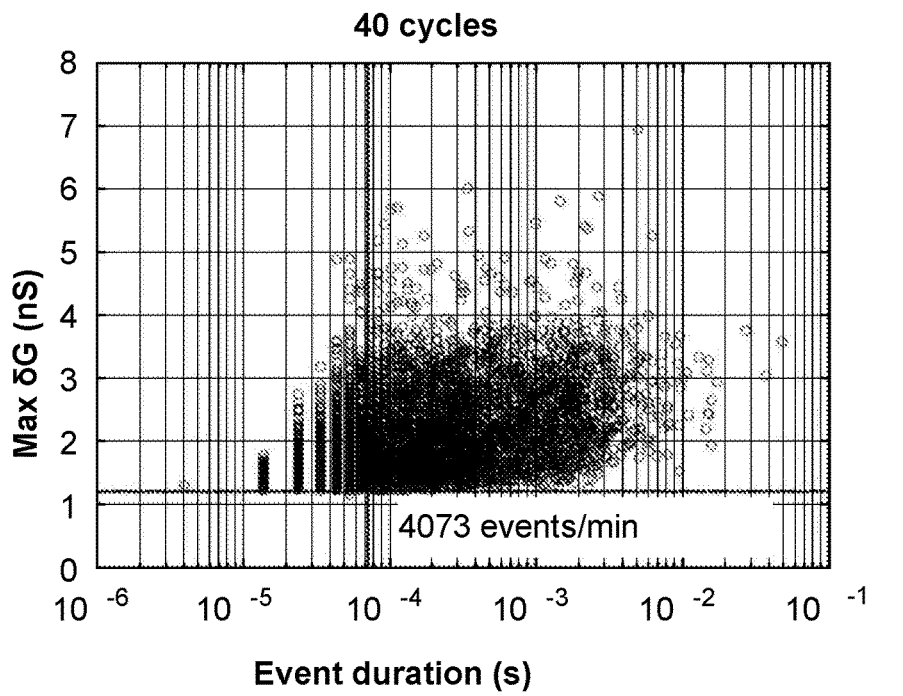
Figure 12:
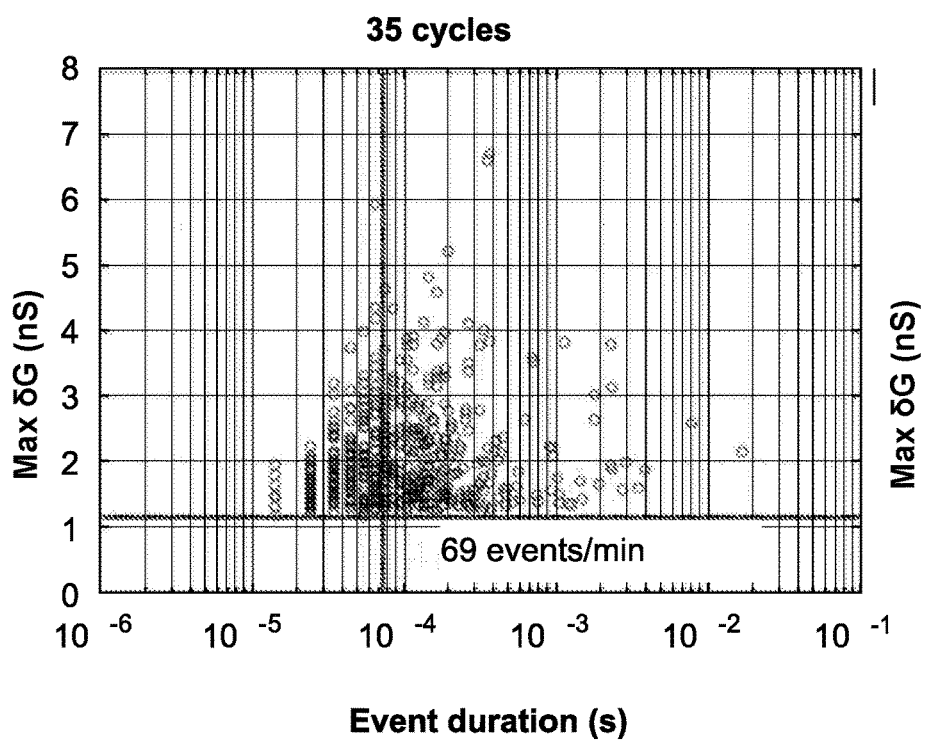
Figure 12:
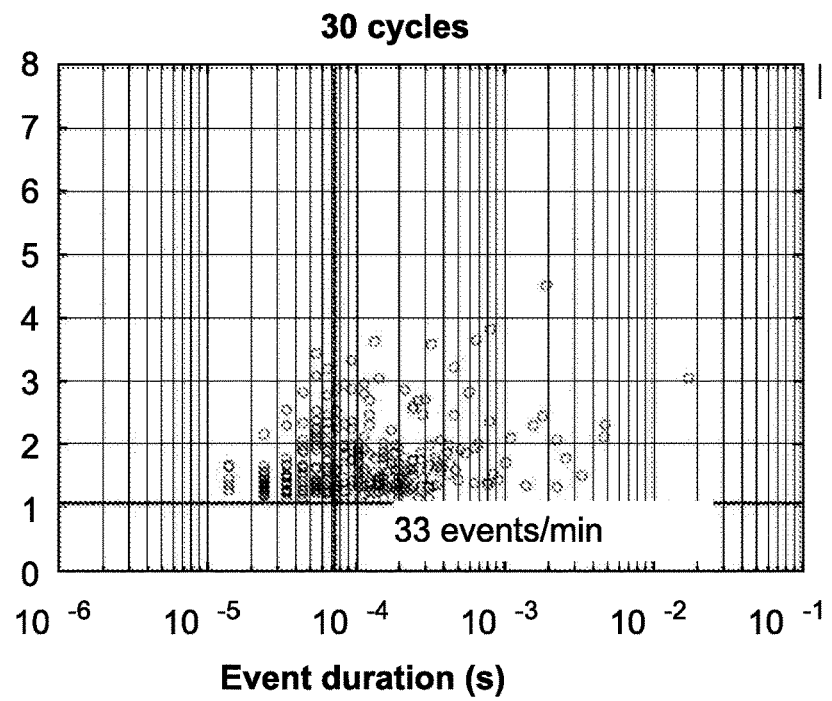
Figure 12:
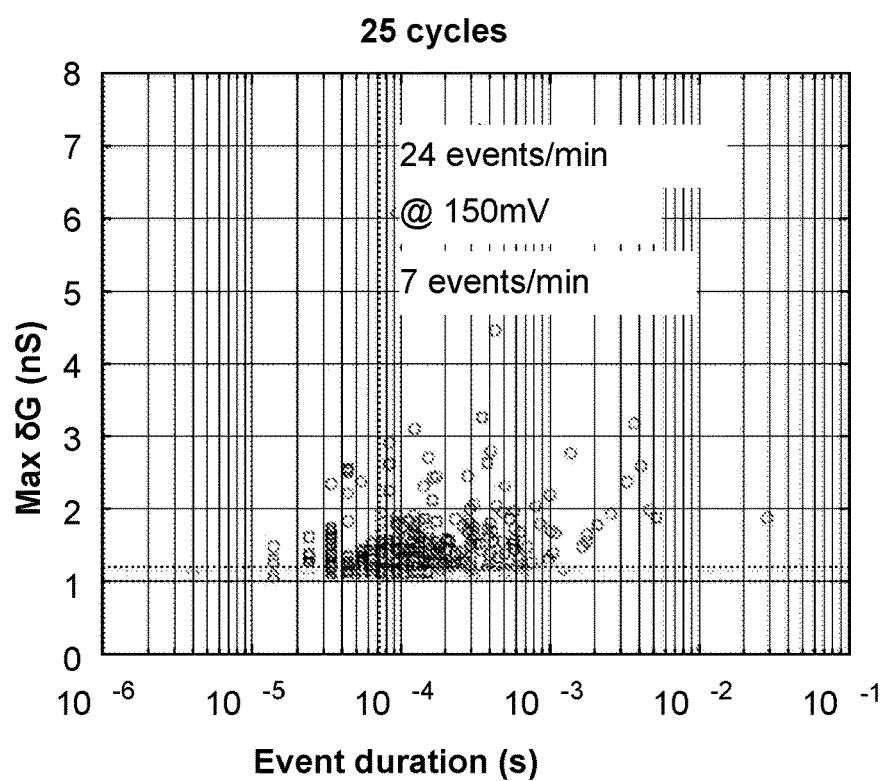
Figure 12:
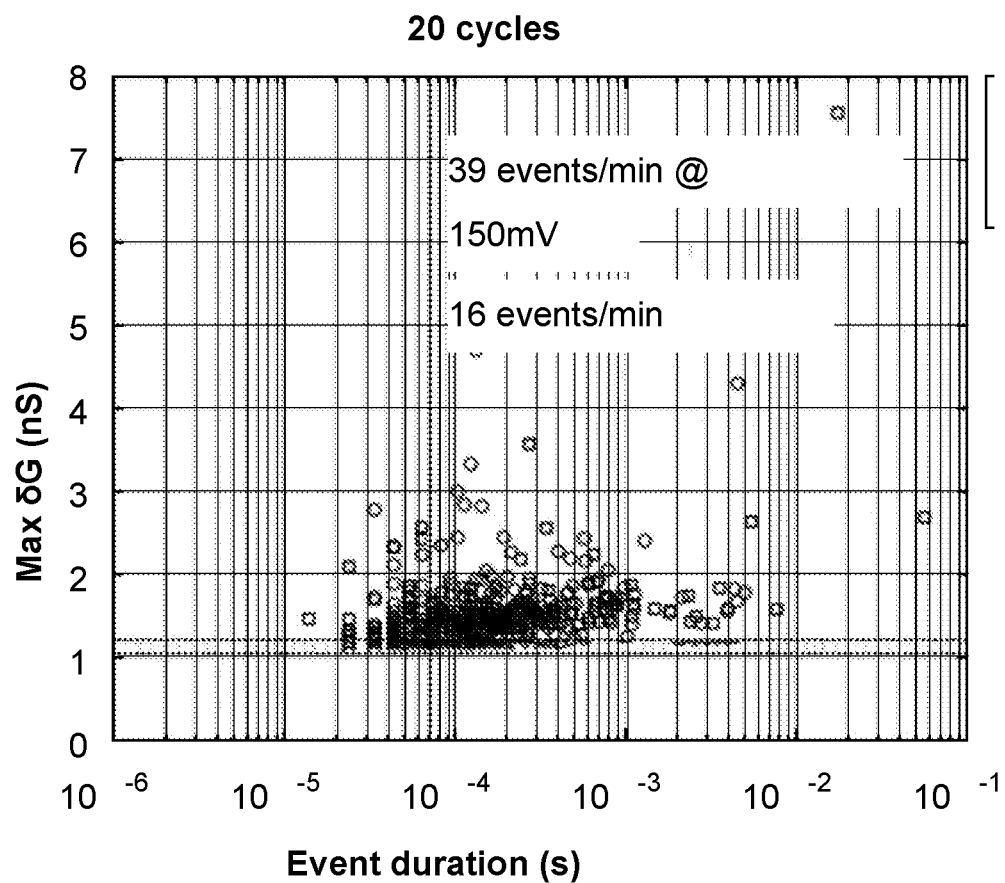

FIG. 12 shows a plot of events detected in a 3M/1.5M CsCl buffer gradient sensing solution with a 25 nm nanopore for a 109 bp dsDNA amplicon collected after 20, 25, 30, 35, or 40 amplification cycles.

Figure 13:
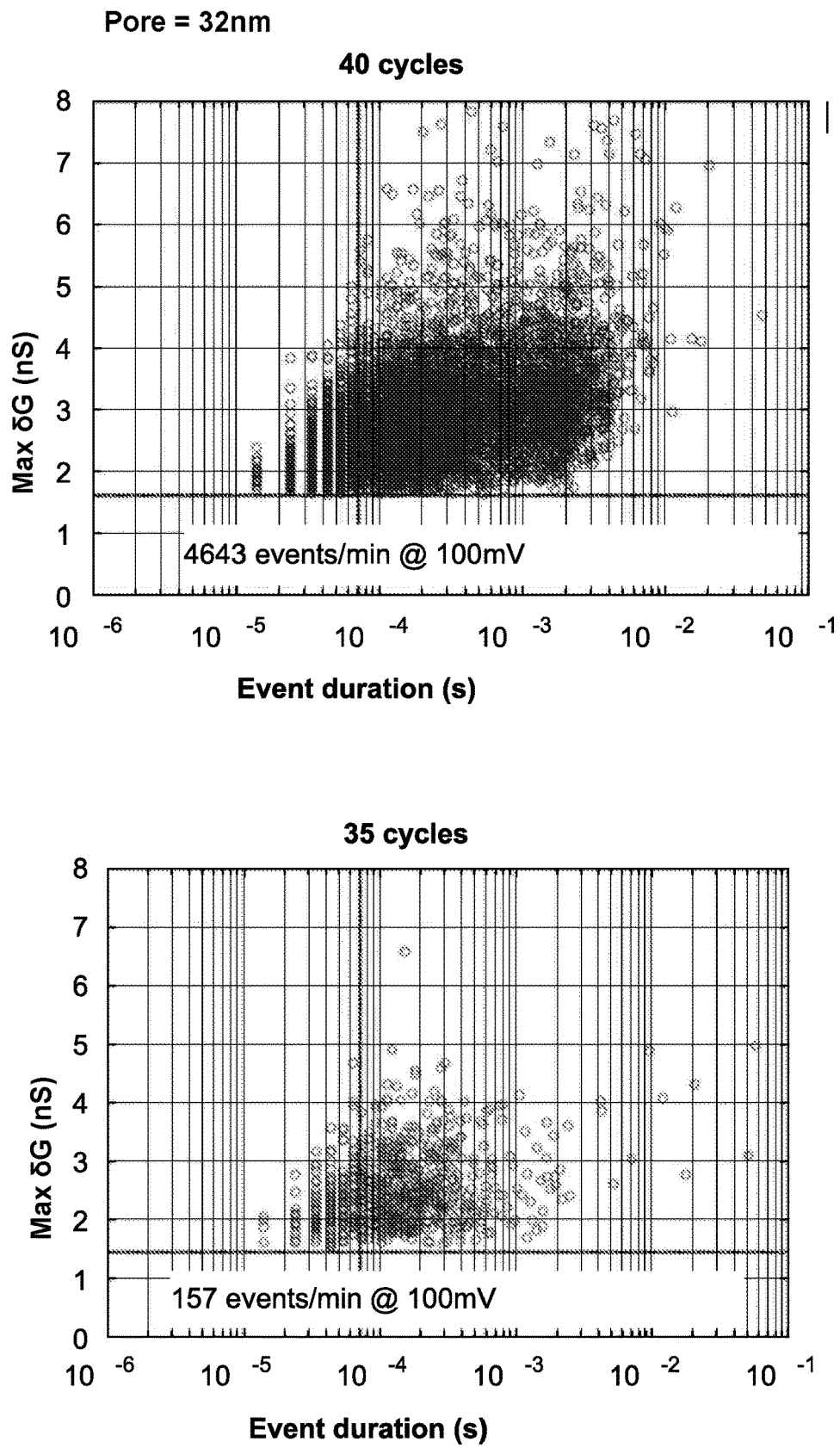
Figure 13:
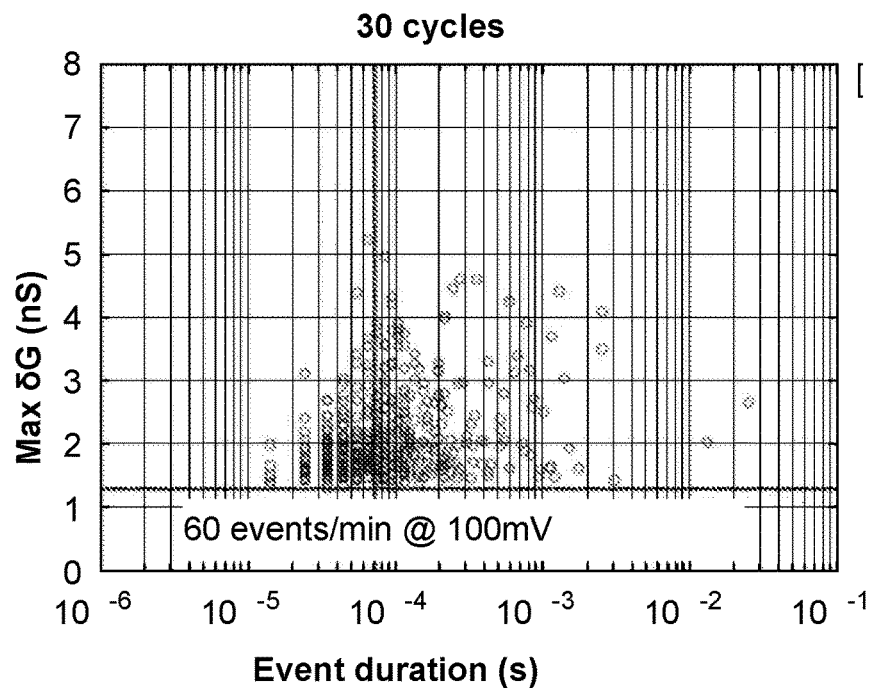
Figure 13:
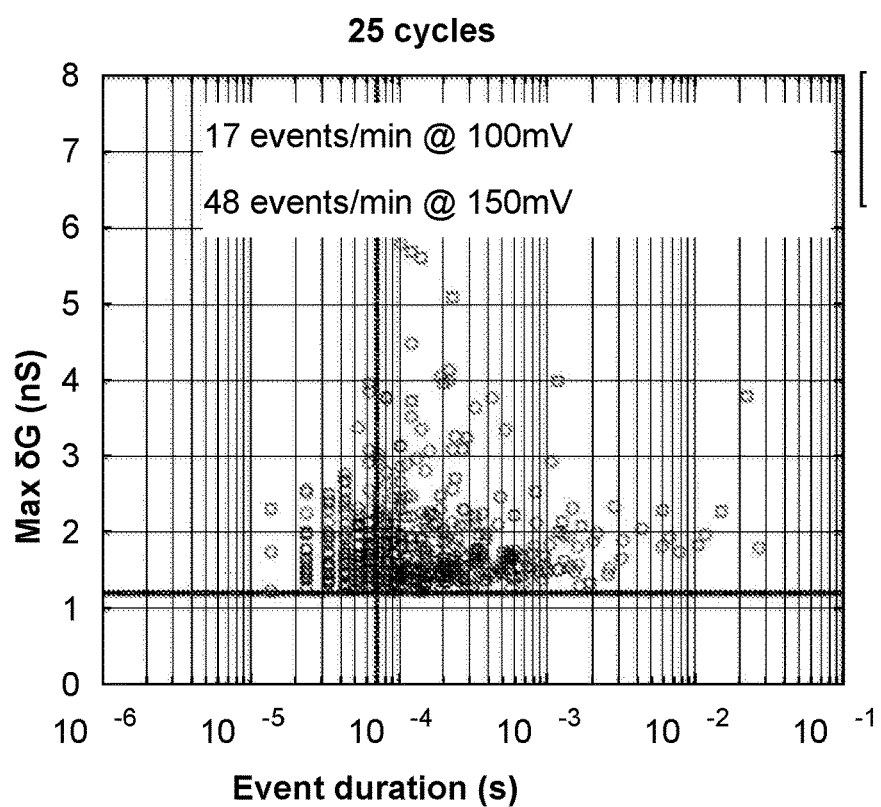
Figure 13:
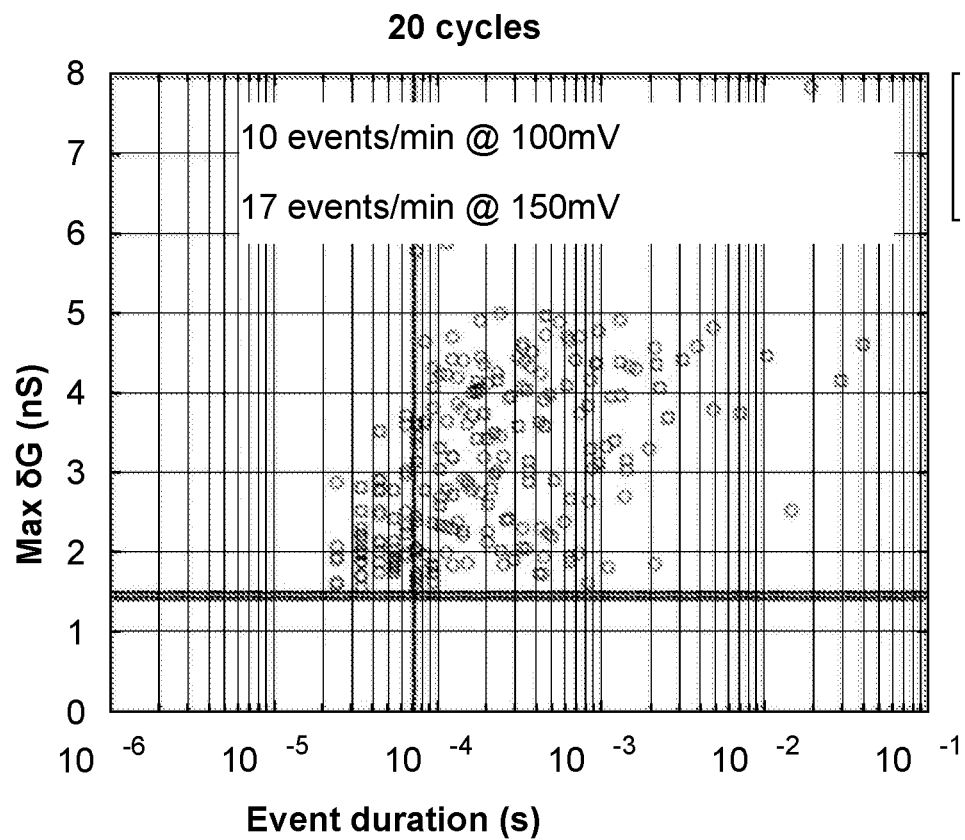

FIG. 13 shows a plot of events detected in a 3M/1.5M CsCl gradient sensing solution with a 32 nm nanopore for a 109 bp DNA amplicon collected after 20, 25, 30, 35, or 40 amplification cycles.

Figure 14:
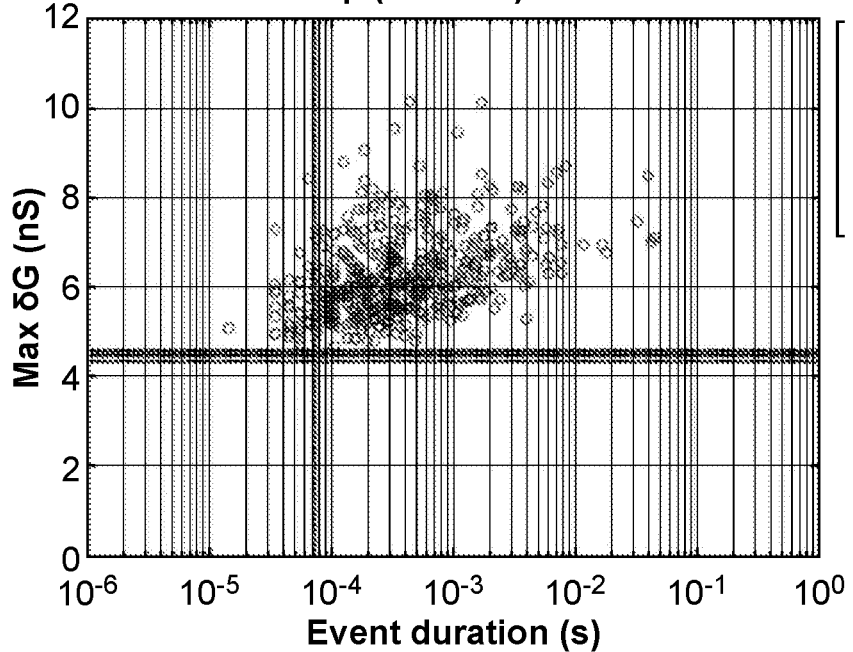
Figure 14:
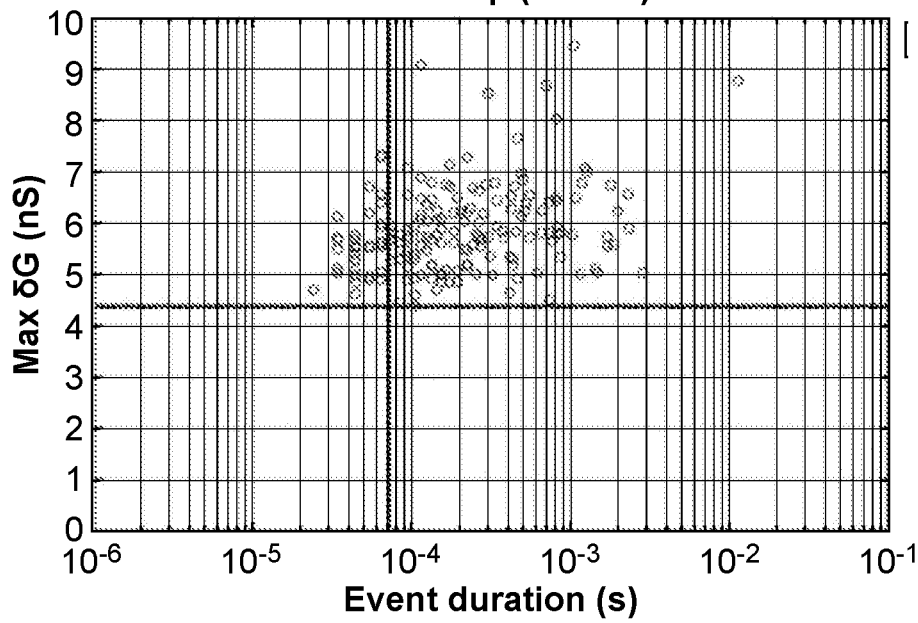

FIG. 14 shows a plot of events detected in a 3M/1.5M CsCl gradient sensing solution with a 90 nm nanopore for a 109 bp dsDNA sample with a concentration of 13 nM or a 74 bp dsDNA sample with a concentration of 20 nM.

Figure 15:
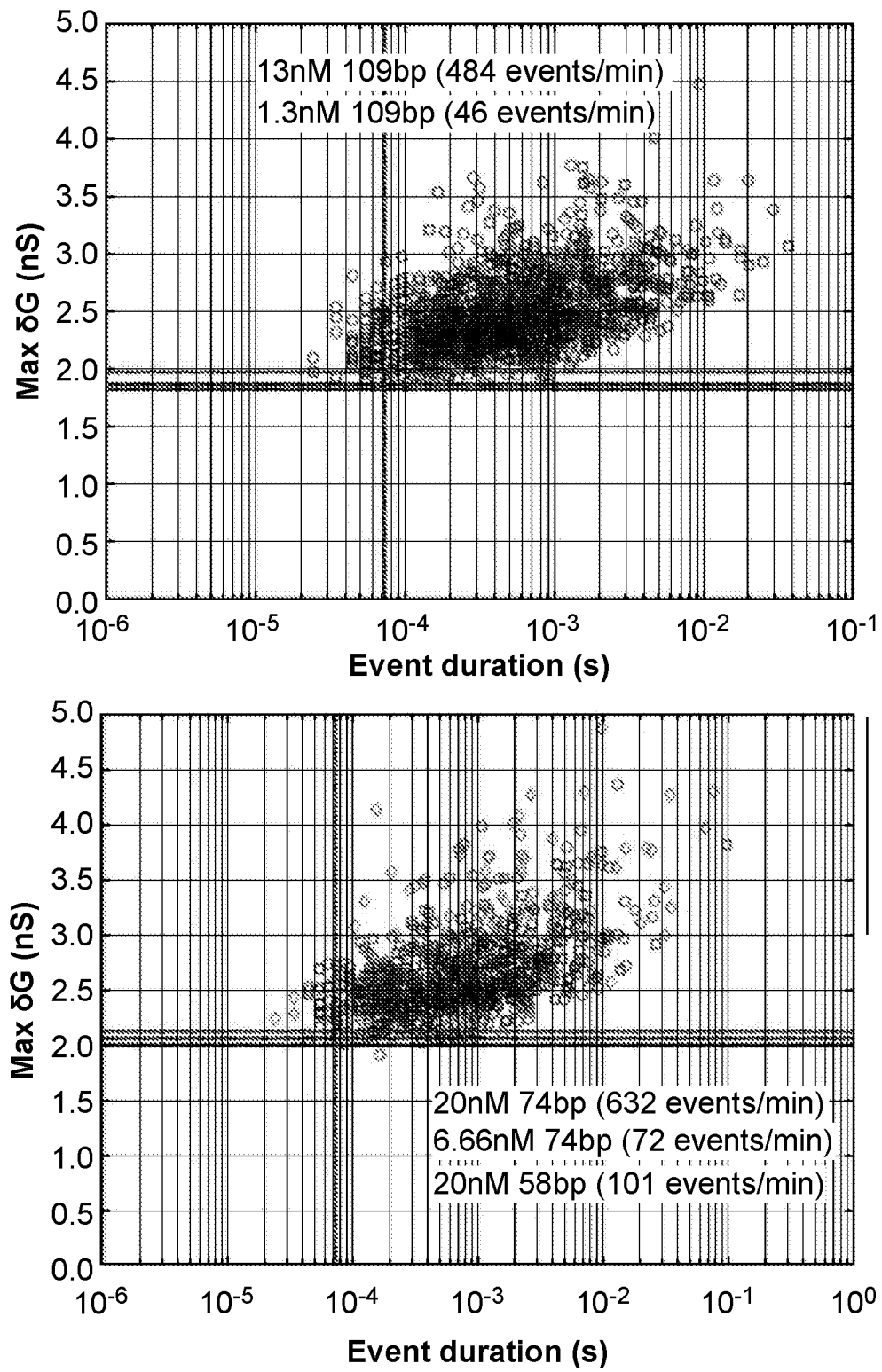

FIG. 15 shows a plot of events detected in a 3M/1.5M CsCl gradient sensing solution with a 102 nm nanopore. The upper panel shows a 109 bp dsDNA sample with a concentration of 13 nM (circles), 109 bp dsDNA sample with a concentration of 1.3 nM (squares). The lower panel shows a 74 bp dsDNA sample with a concentration of 20 nM (circles), a 74 bp dsDNA sample with a concentration of 6.66 nM (squares), or a 58 bp DNA with a concentration of 20 nM (diamond).

Figure 16A:
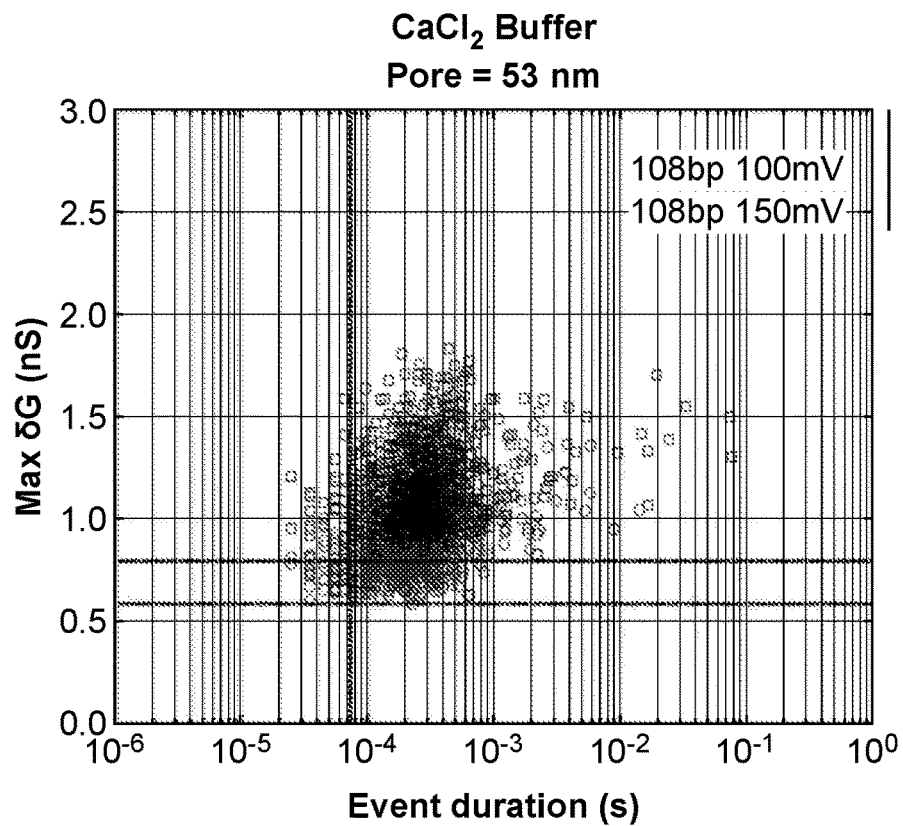
Figure 16B:
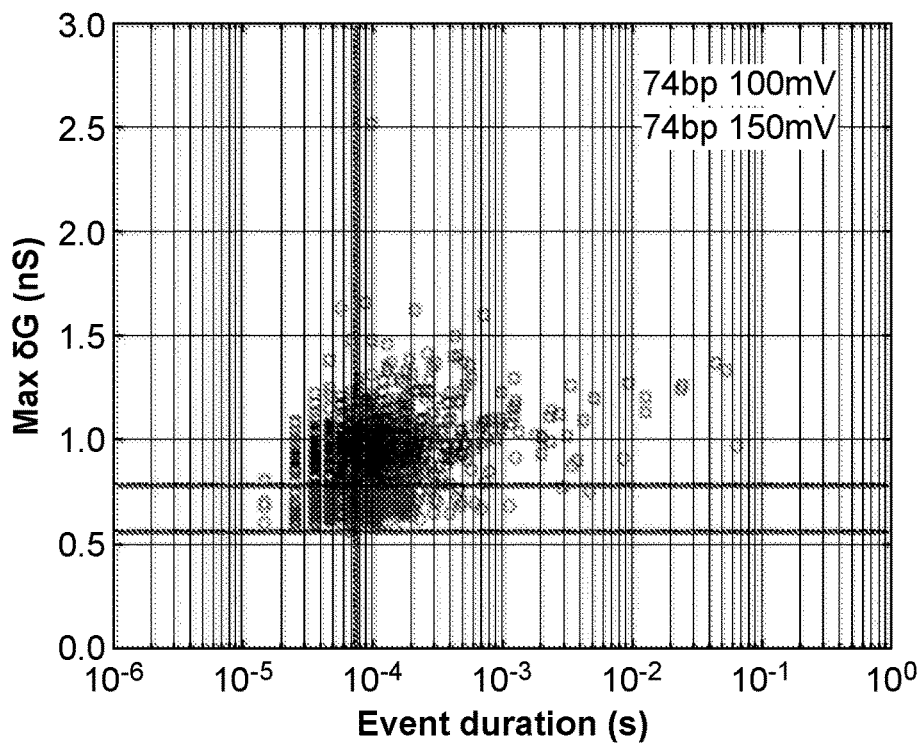

FIGS. 16A-16B show a plot of events detected in a 1M $CaCl_2$ sensing solution with a 53 nm nanopore for run at either 100 mV (square) or 150 mV (circle). FIG. 16A shows a plot of events for a 108 bp dsDNA sample. FIG. 16B shows a plot of events for a 74 bp dsDNA sample.

Figure 17:
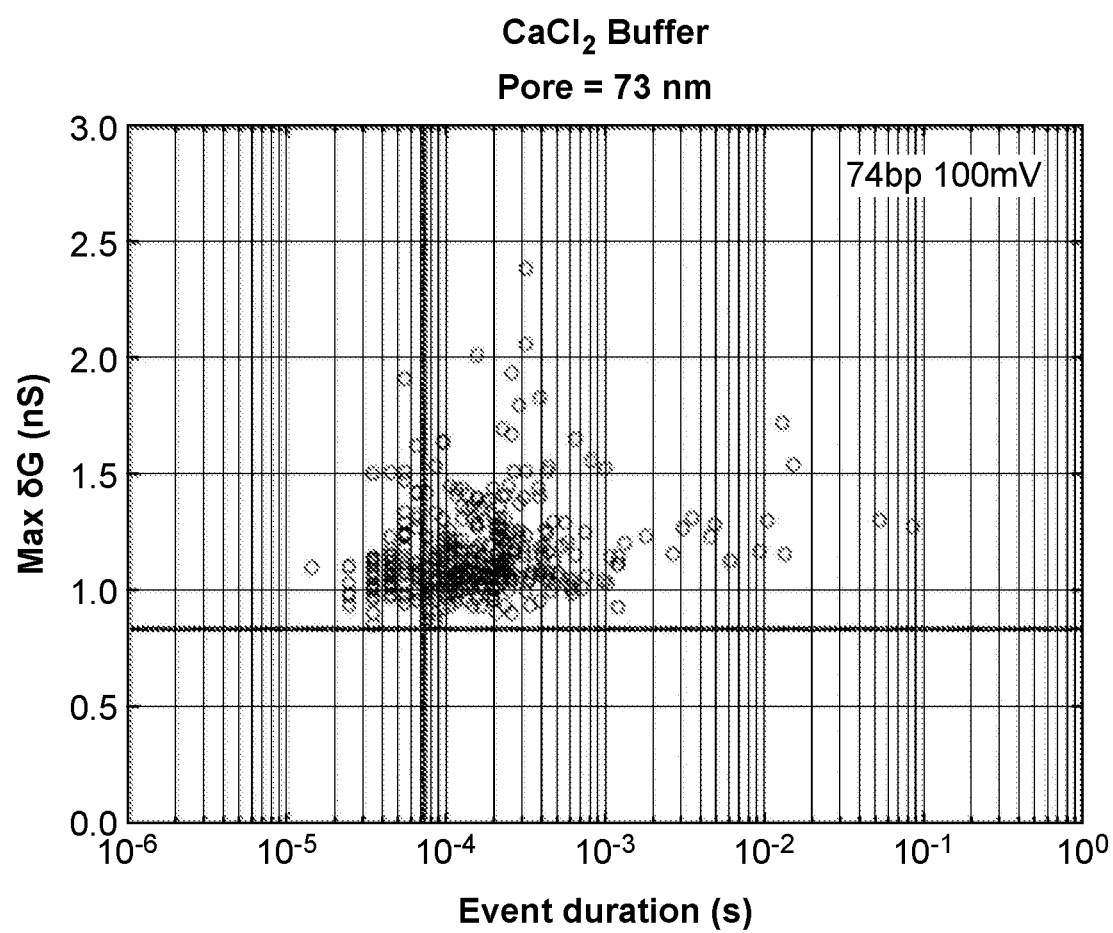

FIG. 17 shows a plot of events detected in a 1M $CaCl_2$ sensing solution with a 73 nm nanopore for a 74 bp dsDNA sample.

Figure 18A:
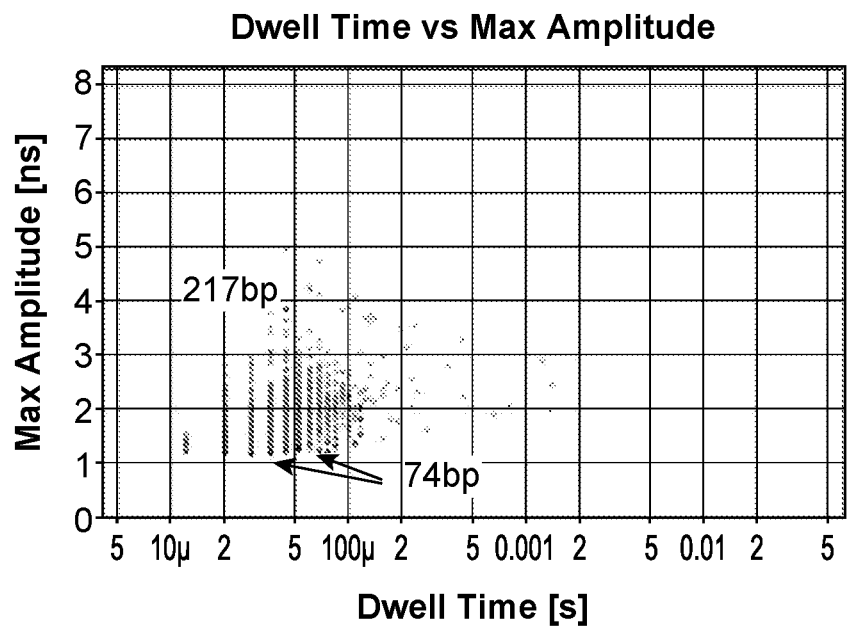
Figure 18B:
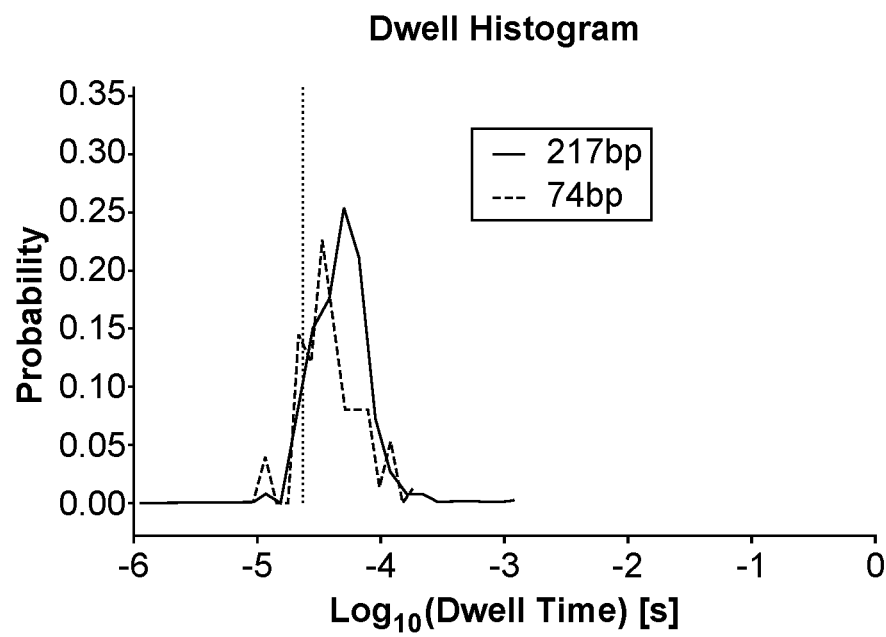

FIGS. 18A-18B show representative data from 4M LiCL buffer collected for a 74 bp dsDNA and a 217 dsDNA ran in isolation in a 30 nm nanopore. 18A shows a plot of detected events. 18B shows a histogram of the log of detected event dwell times.

Figure 19A:
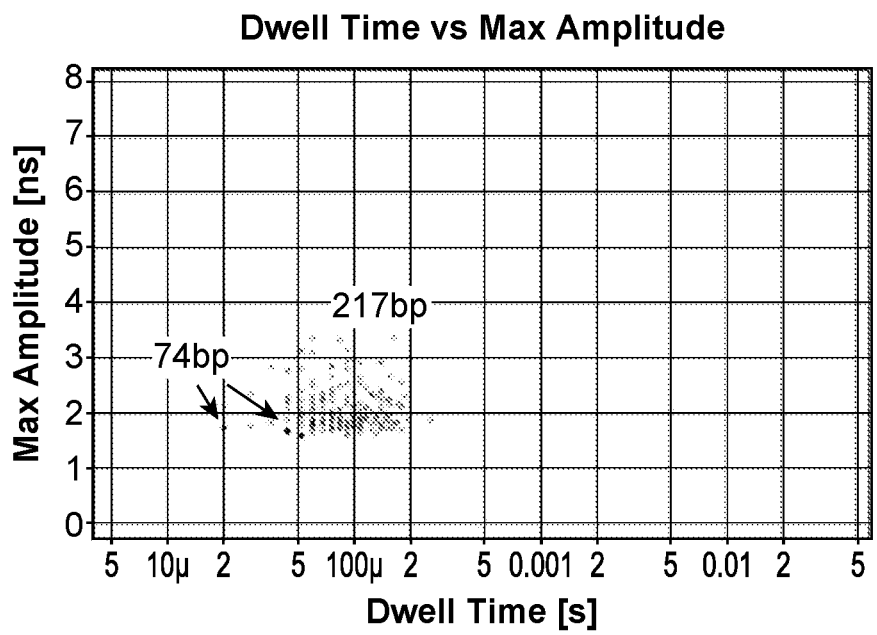
Figure 19B:
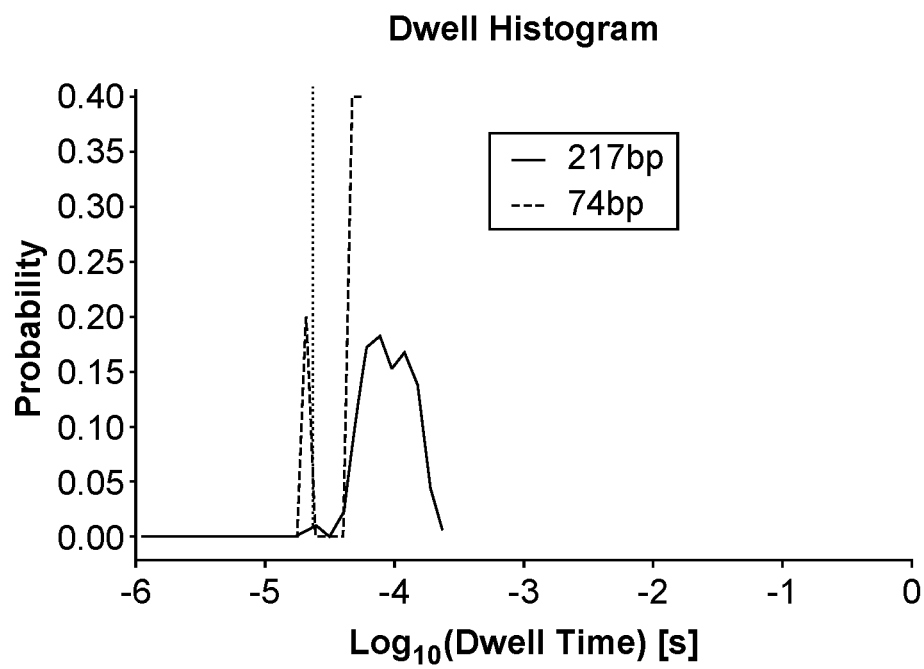

FIGS. 19A-19B show data from a 20% Maltose sensing solution with a 26 nm nanopore for a 74 bp dsDNA and 217 dsDNA ran in isolation. 19A shows a plot of detected events. 19B shows a histogram of the log of detected event dwell times.

Figure 20A:
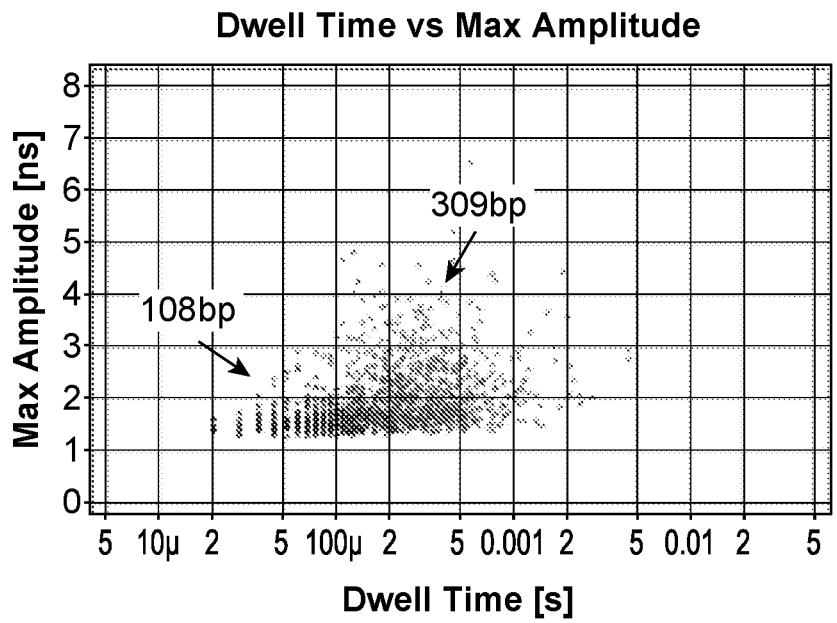
Figure 20B:
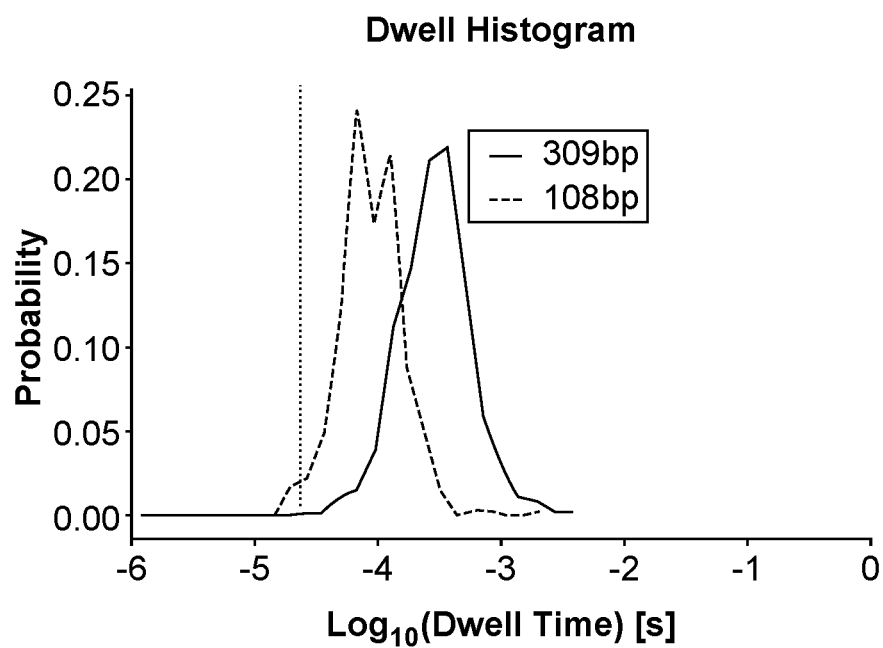

FIGS. 20A-20B show data from a 30% Ethylene glycol sensing solution with a 37 nm nanopore for a 108 bp and a 309 bp dsDNA ran in isolation. 20A shows a plot of detected events. 20B shows a histogram of the log of detected event dwell times.

Figure 21A:
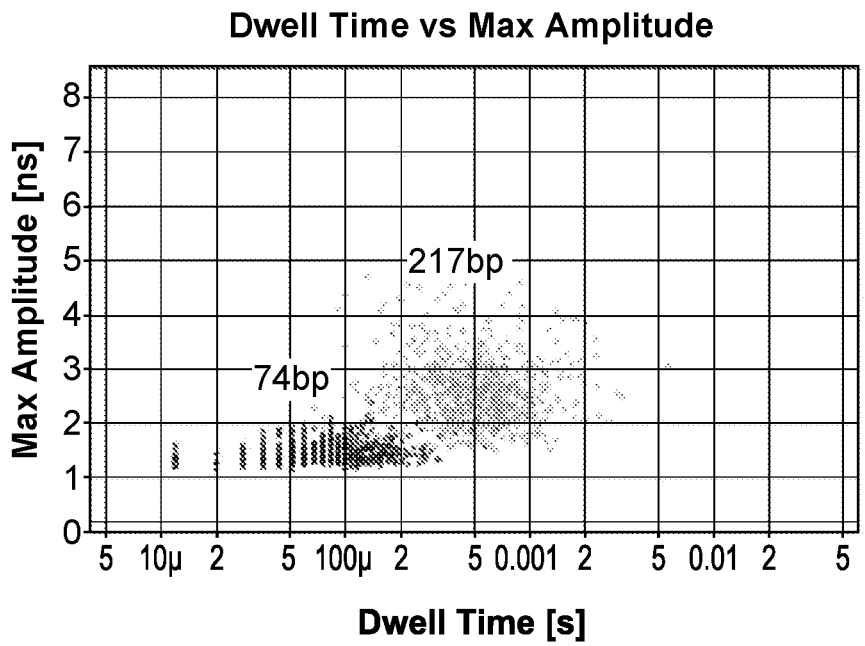
Figure 21B:
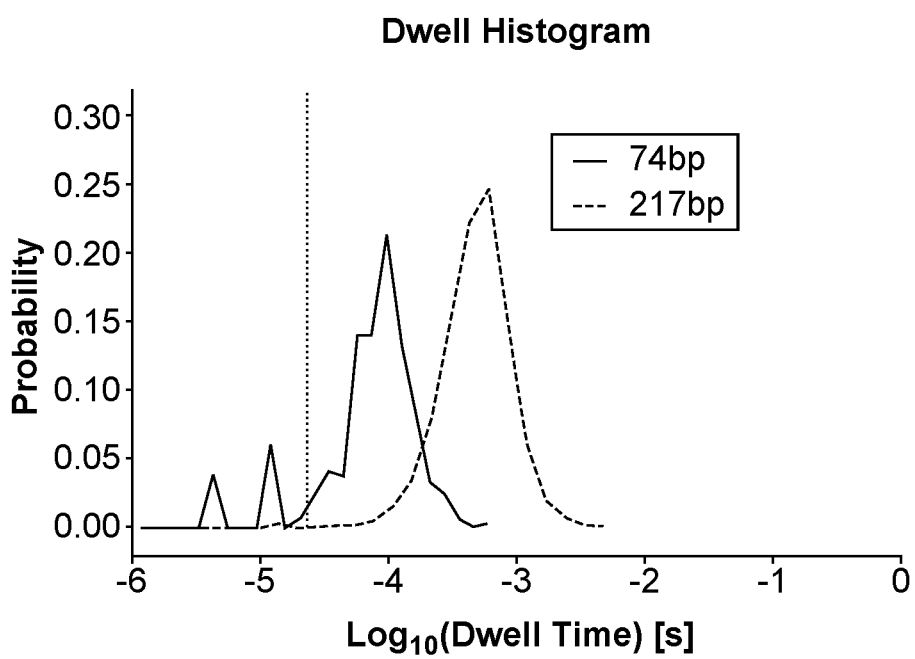

FIGS. 21A-21B show data from a 15% Triethylene glycol (TEG) sensing solution with a 30 nm nanopore for a 74 bp and a 217 bp dsDNA ran in isolation. 21A shows a plot of detected events. 21B shows a histogram of the log of detected event dwell times.

Figure 22A:
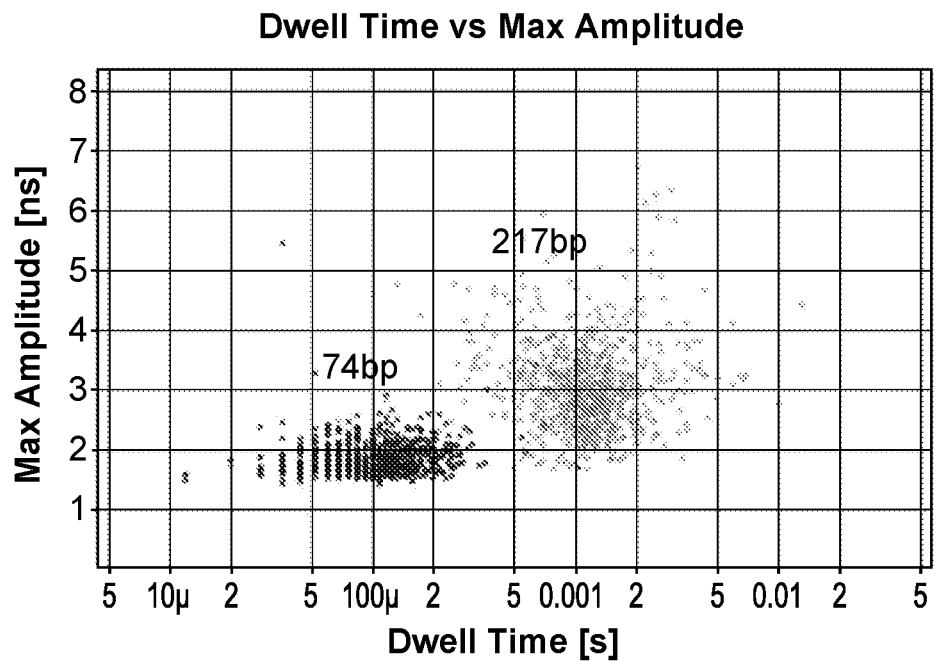
Figure 22B:
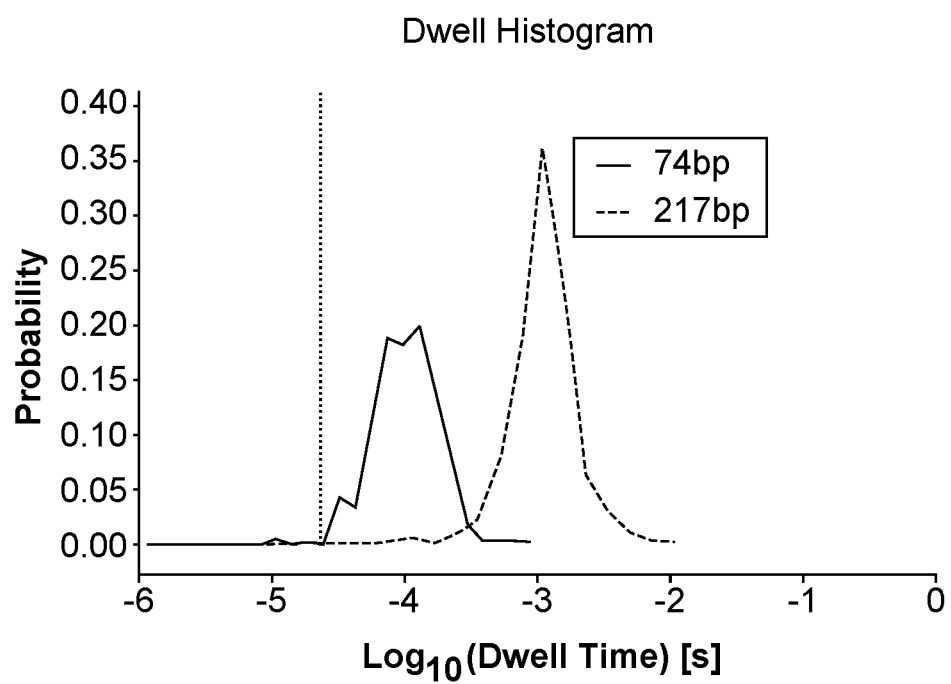

FIGS. 22A-22B show data from a 10% Tripropylene glycol (TPG) sensing solution with a 30 nm nanopore for a 74 bp and a 217 bp dsDNA ran in isolation. 22A shows a plot of detected events. 22B shows a histogram of the log of detected event dwell times.

Figure 23A:
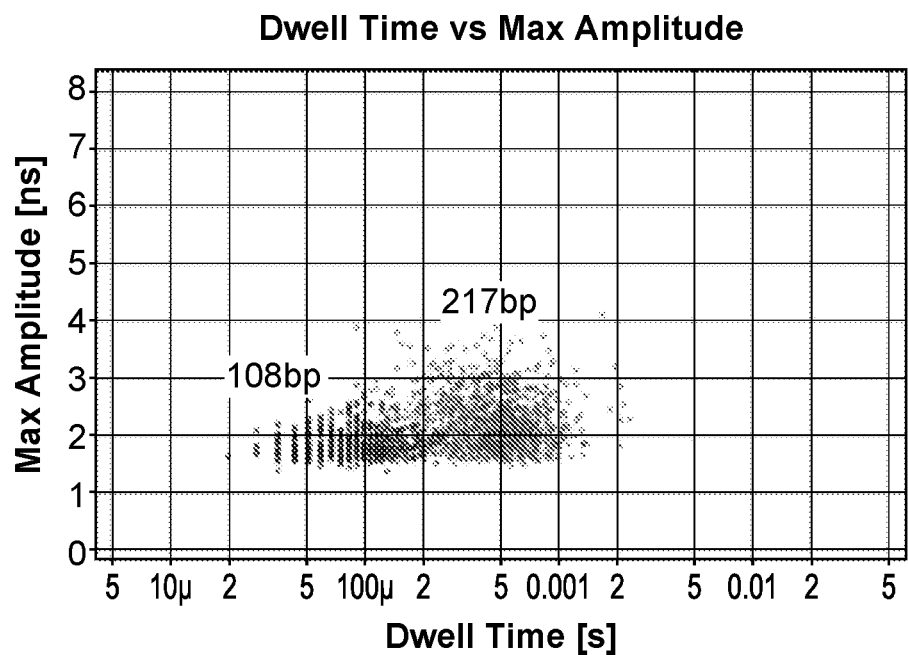
Figure 23B:
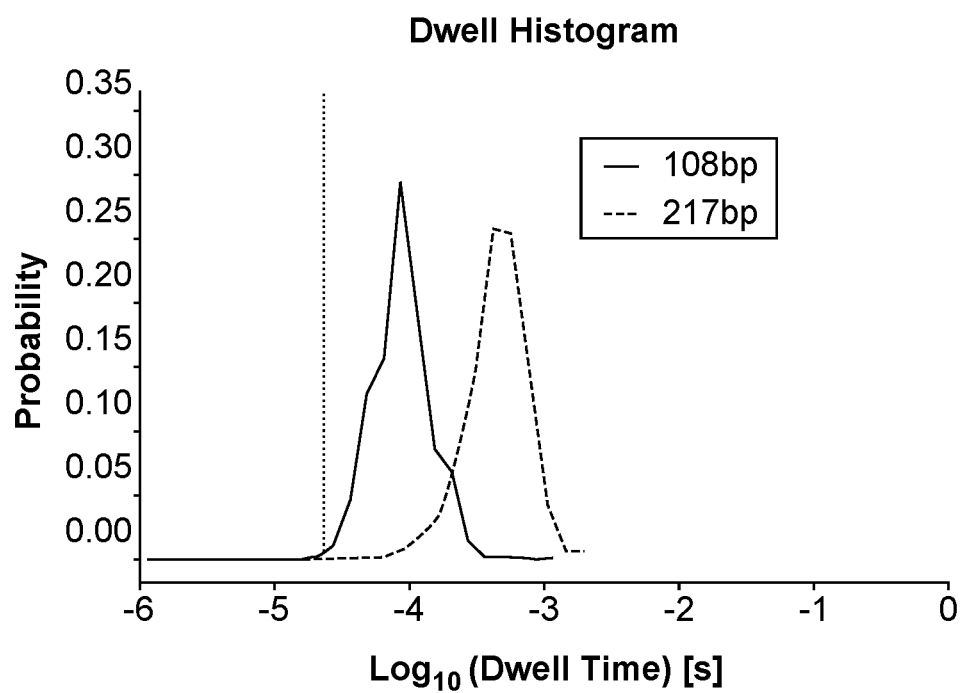

FIGS. 23A-23B show data from a 10% Tetraethylene glycol dimethyl ether (TTEG-DME) sensing solution with a 31 nm nanopore for a 108 bp and a 217 bp dsDNA ran in isolation. 23A shows a plot of detected events. 23B shows a histogram of the log of detected event dwell times.

Figure 24A:
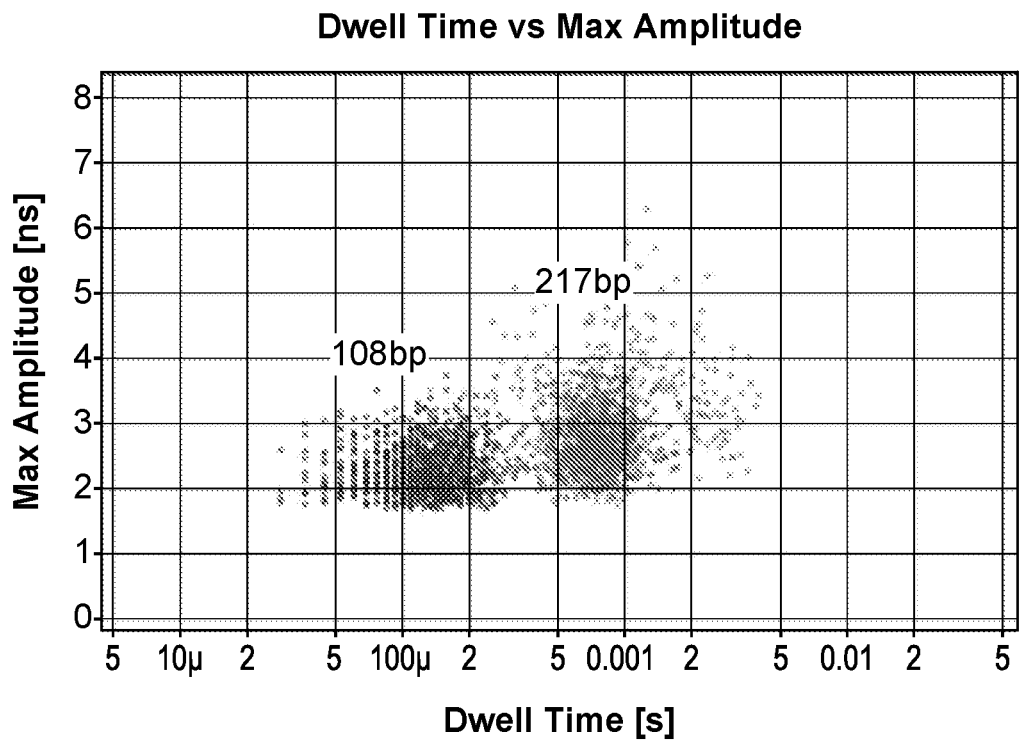
Figure 24B:
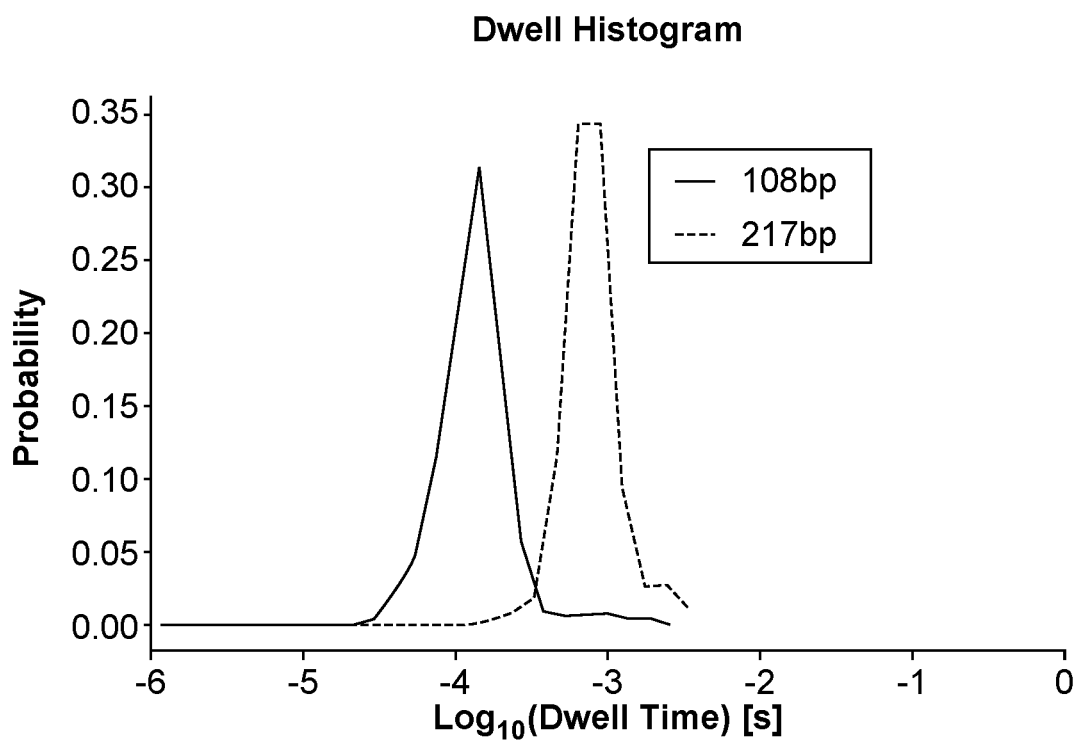

FIGS. 24A-24B show data from a 10% Tripropylene glycol monomethyl ether (TPG-MME) sensing solution in a 34 nm nanopore for 108 bp and 217 bp dsDNA ran in isolation. 24A shows a plot of detected events. 24B shows a histogram of the log of detected events.

Figure 25A:
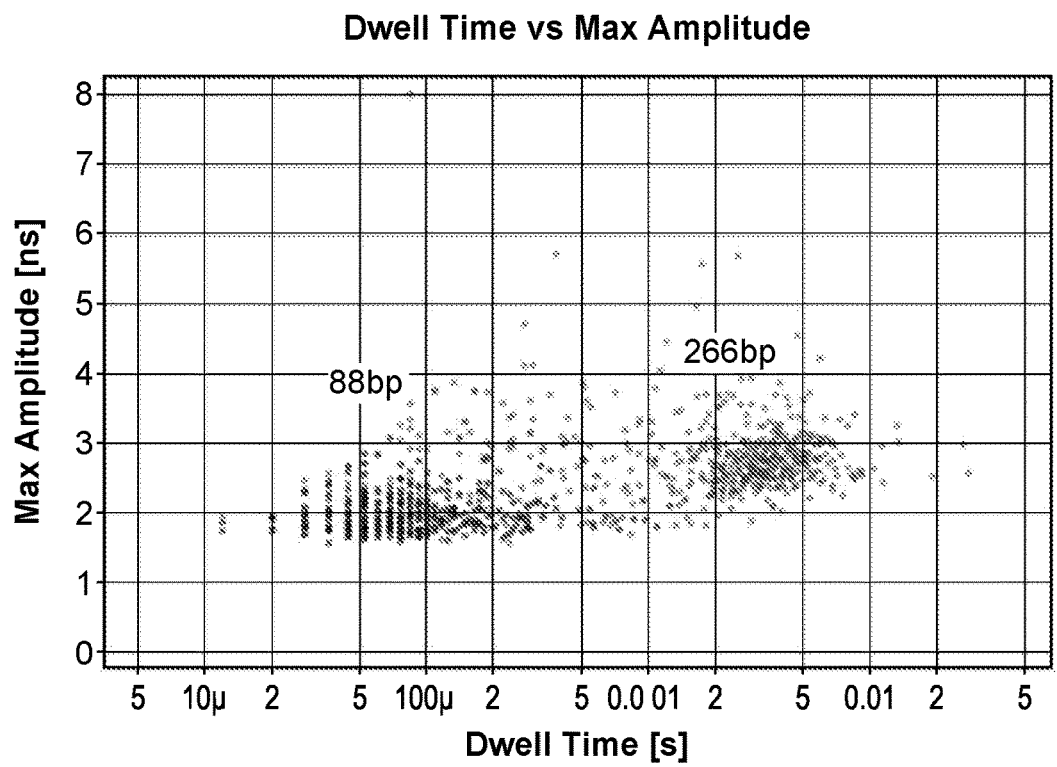
Figure 25B:
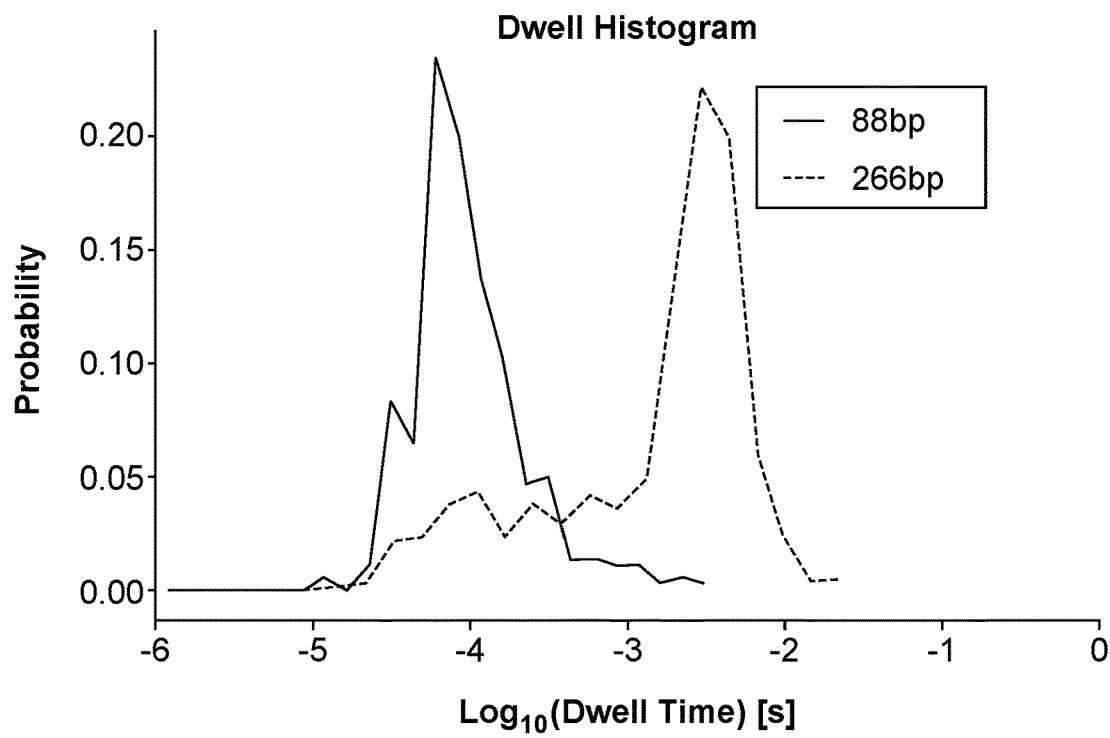

FIGS. 25A-25B show data from an asymmetric 10% PEG 200 (cis)/10% Maltose (trans) sensing solutions with a 35 nm nanopore for a 88 bp and a 266 bp dsDNA ran in isolation. 25A shows a plot of detected events. 25B shows a histogram of the log of detected event dwell times.

Figure 26A:
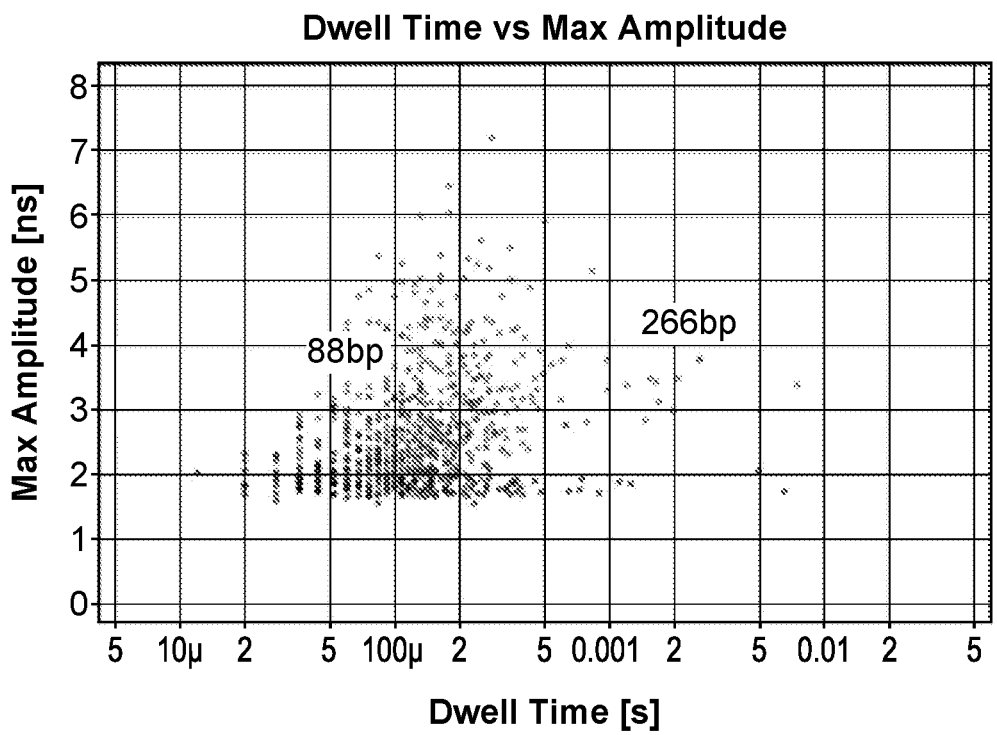
Figure 26B:
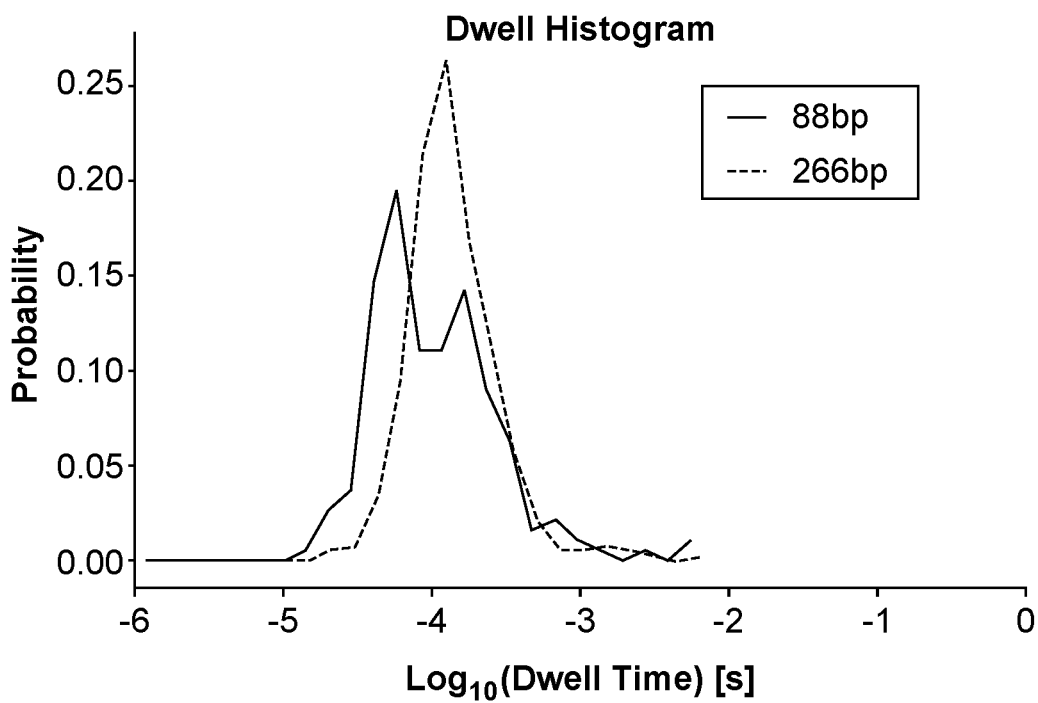

FIGS. 26A-26B show data from an asymmetric 10% Maltose (cis)/10% PEG 200 (trans) sensing solutions in a 35 nm nanopore for a 88 bp and a 266 bp dsDNA ran in isolation. 26A shows detection of events. 26B shows a histogram of the log of detected event dwell times.

Figure 27A:
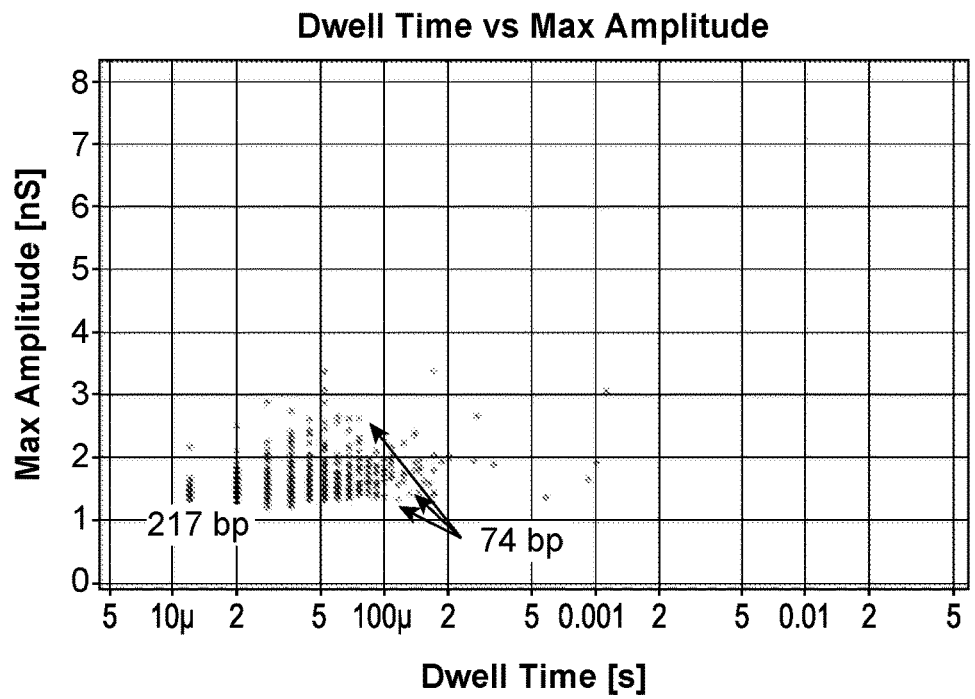
Figure 27B:
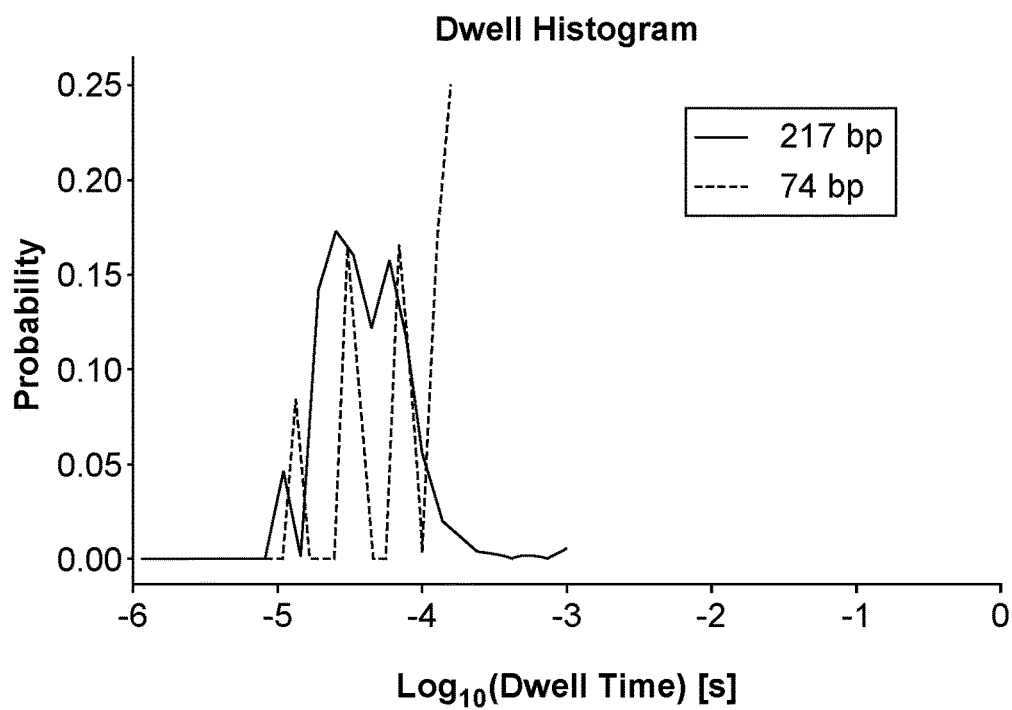

FIGS. 27A-27B show representative from a PEG 8000 sensing solution in a 32 nm nanopore for a 74 bp and 217 bp dsDNA ran in isolation. 26A shows detection of events. 27B shows a histogram of the log of detected event dwell times.

Figure 28A:
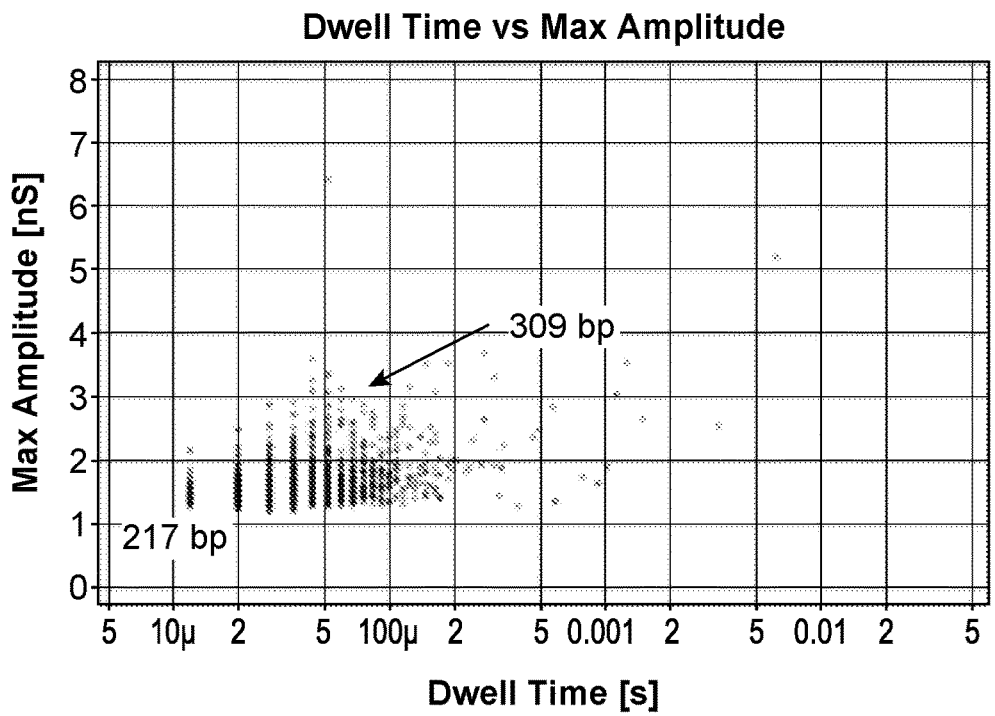
Figure 28B:
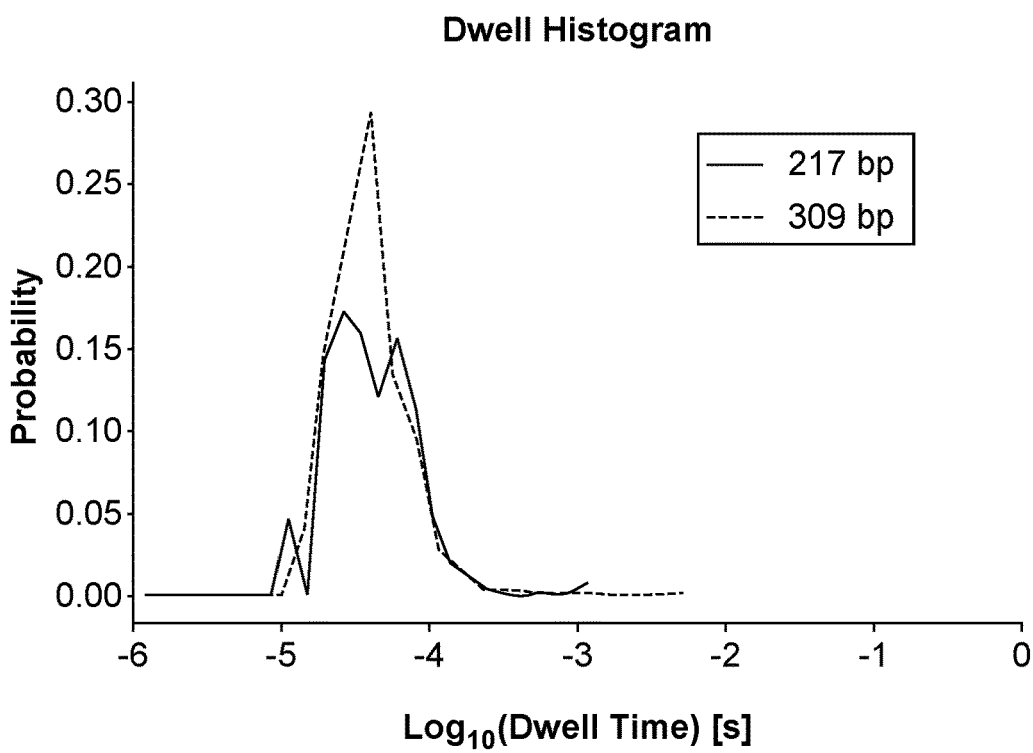

FIGS. 28A-28B show data from a PEG 8000 sensing solution with a 32 nm nanopore for a 217 bp and a 309 bp dsDNA ran in isolation. 28A shows a plot of detected events. 28B shows a histogram of the log of detected event dwell times.

Figure 29A:
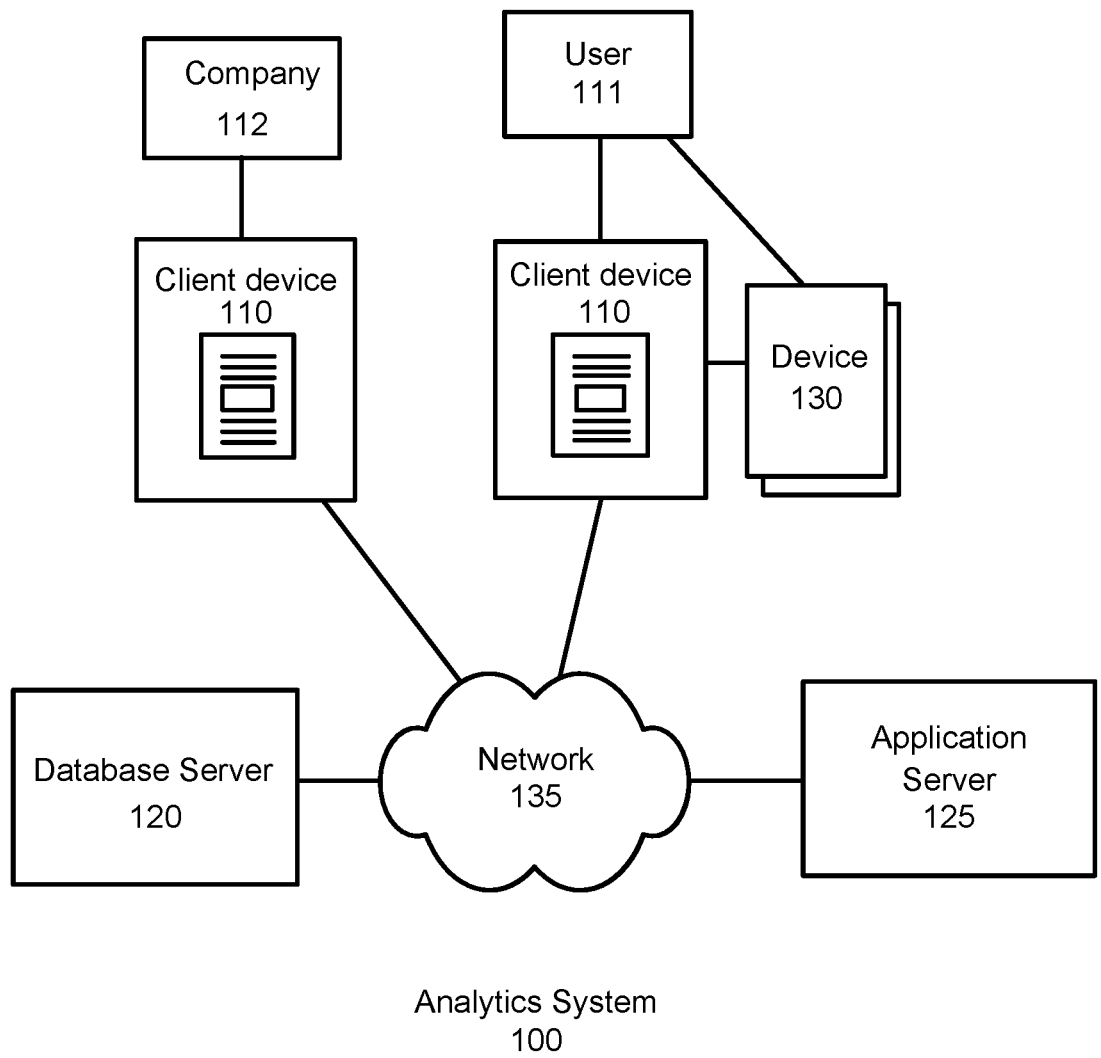
Figure 29B:
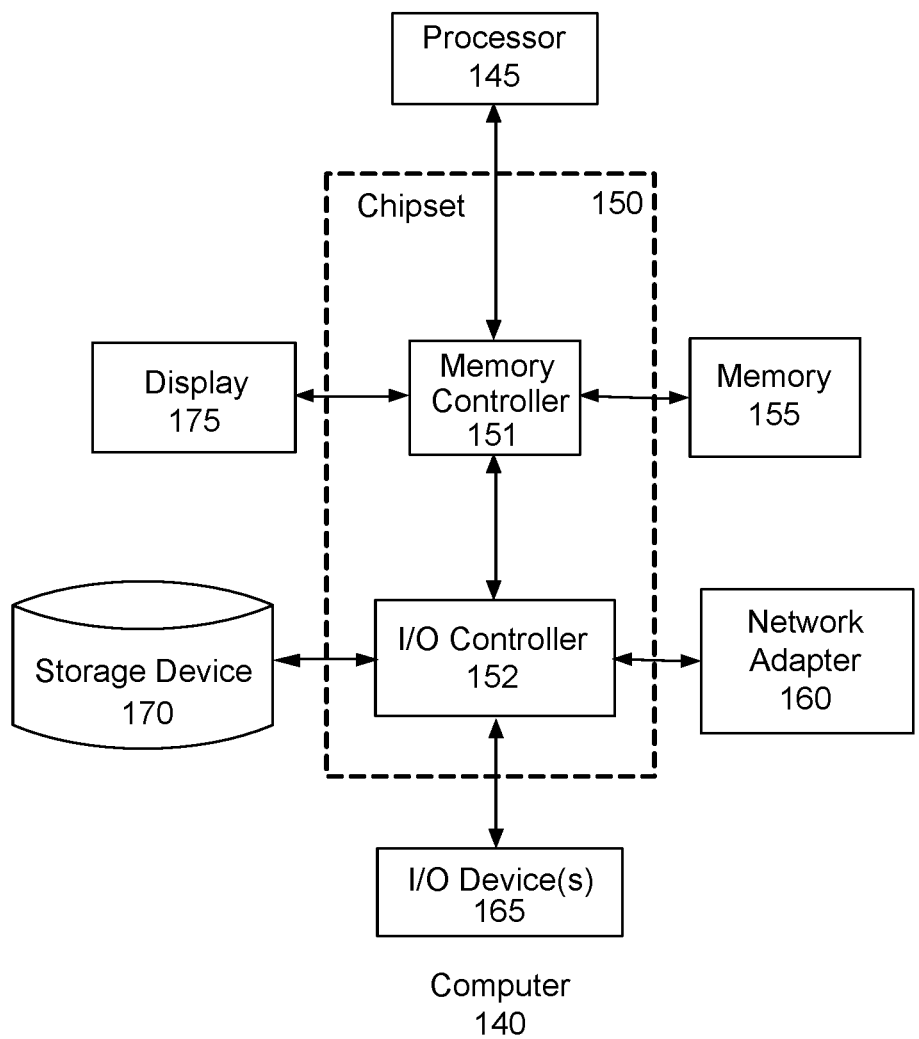

FIGS. 29A-29B: show diagrams illustrating a computer system used with a nanopore device to carry out analytics on raw current data and provide summary analytics to a user or a company that provides data to the user.

5. DETAILED DESCRIPTION

5.1. Definitions

Unless defined otherwise, all technical and scientific terms used herein have the meaning commonly understood by a person skilled in the art to which this invention belongs. As used herein, the following terms have the meanings ascribed to them below.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary, and that equivalents of such are known in the art.

The term "a pore" or "nanoporous" refers to a single opening or an array of openings in a membrane of any material type. A pore can have any size that allows for the translocation of a molecule or analyte through the membrane. A pore can have any shape.

The term "biomolecules" refer to nucleic acids (e.g., polynucleotide such as DNA, RNA or LNA), proteins, peptides, antibodies, small molecules, aptamers, analytes, or any drug agents. The biomolecules can be from a natural source. The biomolecules can be synthetically made. The biomolecule can be linked or conjugate to a means for detection.

The term "amplification" or "amplification reaction" refers to a reaction that generates a plurality of clonal amplicons comprising a target polynucleotide sequence from the target polynucleotide sequence. Amplification reaction reagents include any molecules that are necessary to perform amplification of the target polynucleotide sequence. Amplification reaction reagents can include, but are not limited to, free primers, dNTPs (deoxynucleotide triphosphates, dATP, dGTP, dCTP, dTTP), polymerase enzymes (e.g., Taq or Pfu), salts (Magnesium chloride, Magnesium Sulfate, Ammonium sulfate, sodium chloride, potassium chloride), BSA (bovine serum albumin) stabilizer, and detergents (e.g., triton X-100). Amplification reactions can include, but are not limited to, e.g., PCR, ligase chain reaction (LCR), transcription mediated amplification (TMA), reverse transcriptase initiated PCR, DNA or RNA hybridization techniques, sequencing, isothermal amplification, and loop-mediated isothermal amplification (LAMP). Techniques of amplification to generate an amplicon from a target polynucleotide sequence are well known to one of skill in the art.

The term "current measurement" refers to a series of measurements of current flow at an applied voltage through the nanopore over time. The current is expressed as a measurement to quantitate events, and the current normalized by voltage (conductance) is also used to quantitate events.

The term "open channel" refers to the baseline level of current through a nanopore channel within a noise range where the current does not deviate from a threshold of value defined by the analysis software.

The term "event" refers to a set of current impedance measurements that begins when the current measurement deviates from the open channel value by a defined threshold, and ends when the current returns to within a threshold of the open channel value.

The term "current impedance signature" refers to a collection of current measurements and/or patterns identified within a detected event from a target molecule or a target molecule that has been modified to enhance detection (e.g., probe, label, dye or voltage-sensitive moiety). "Current impedance signature" is used interchangeably with "current signature." Multiple signatures may also exist within an event to enhance discrimination between molecule types. Examples of a signature includes, but is not limited to, calculated event dwell time, mean event amplitude, maximum event amplitude, median event amplitude, event area or others known in the art. One skilled in the art would appreciate that a signature could also include any combination calculated event dwell time, mean event amplitude, maximum event amplitude, median event amplitude, or event area.

The term "capture rate" refers to the number of events detected over time in a nanopore device. In some embodiments, the capture rate can refer specifically to the rate of capture and/or translocation of events associated with a specific target molecule, e.g., translocation of a DNA amplicon. As described herein, the capture rate can be used to infer concentration as compared to a control with a similar mass/charge ratio under similar nanopore conditions.

As used herein, we denote "cis" as the chamber or volume (used interchangeably) in the nanopore device in which molecules are loaded and captured into the nanopore, and "trans" as the opposing chamber or volume into which molecules enter after passing through the nanopore.

As used herein, the singular forms "a," "an," and "the" include the plural referents unless the context clearly indicates otherwise. The terms "include," "such as," and the like are intended to convey inclusion without limitation, unless otherwise specifically indicated.

Ranges provided herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

5.2. Overview

While the researching nanopore detection methods we discovered that polyether and cation-salt agents enable or facilitate the detection and characterization of target molecules passing through pores of a nanopore device that could not be previously be detected or resolved using conventional nanopore buffers. The present disclosure provides various sensing solution composition, methods, devices, systems, and kits that address some of the challenging issues in nanopore detection for numerous types of biomolecules.

The methods, devices, systems, and kits of the disclosure comprises a sensing solution that enable or facilitate the detection and discrimination of current signals upon translocation of target molecules through a nanopore of the nanoporous membrane, thereby providing increase accuracy. In certain embodiments, probes. voltage-sensitive moieties or other labels can be used with the methods, devices, systems, and kits of the disclosure to further enhance detection of a biomolecule.

The various inventive aspects provided by the disclosure are particularly useful for detecting and resolving molecules in a sample that have similar physical characteristics, such as length, charge, and/or structure, and would otherwise not be easily detected, resolved from one another, or capable of characterization using standard (e.g., conventional) nanopore buffers.

Any applications that require accurate detection and characterization of biomolecules (e.g., analytes, nucleic acids, and proteins) can make use of the compositions, methods, systems, and kits of the disclosure. Consequently, the compositions, methods, systems, and kits of the disclosure can be applied to applications such as diagnostics, infectious disease testing, genetic screening, and drug or chemical agent screening.

5.3. Sensing Solution Compositions

The disclosure provides various sensing solution compositions for the detection and characterization of a biomolecule using a nanopore device. The compositions provided by the disclosure are particularly useful for detecting and resolving biomolecules in a sample that have similar physical characteristics such as length, charge, structure, or combination thereof and that would otherwise not be detected, resolved from one another, or characterized in standard buffer using a nanopore device.

It is contemplated that the compositions of the disclosure can be used in an effective amount with the methods, devices, systems, and kits of the disclosure. It is also contemplated that the compositions of the disclosure can be used in an effective amount with the methods, devices, systems, and kits known in the art.

5.3.1. Polyether Agents

The disclosure provides various polyether-based sensing solutions for detection or characterization of a biomolecule in a sample using a nanopore device. We discovered that polyether agents of a generally smaller size or molecular weight, when utilized in sensing solutions to detect analytes in a nanopore device, facilitated detection of target analyte molecules passing through nanopores of a nanopore device.

The polyether agents can be linear polymers of 50 monomeric units or less (e.g., 40 monomeric units or less, 30 monomeric units or less, 20 monomeric units or less). The monomeric units of the polyether agent can be alkoxy or substituted alkoxy units containing an oxygen atom and a $C_{(2-4)}$ alkyl or substituted $C_{(2-4)}$ alkyl. In some cases, the substituted $C_{(2-4)}$ alkyl of the monomeric unit is an alkyl-substituted $C_{(2-4)}$ alkyl. Two monomeric units can be linked together via an ether bond. When multiple monomeric units are linked together they form a saturated polyalkylene glycol chain. In some cases, the polyalkylene glycol chain has a polyether backbone with an attached $C_{(1-6)}$ alkyl substituent in each monomeric unit. It is understood that a polyether agent can include different isomeric forms of the monomeric units, or a mixture of isomeric forms of the agent. It is understood that polymeric compounds can be present as molecules of a single discrete length, or can be polydisperse (e.g., and described by an average MW). The polyether agent can be terminated with hydroxy, alkoxy or substituted alkoxy. In some cases, the alkoxy or substituted alkoxy terminal groups are $C_{(1-6)}$ alkoxy or substituted $C_{(1-6)}$ alkoxy. In some embodiments, the polyether agent is monomeric or dimeric. In certain embodiments, the polyether agent is monomeric and is terminated by hydroxy or alkoxy terminal groups. It is understood that, in certain special cases when the polyether agent is monomeric and includes terminal hydroxy groups (e.g., ethylene glycol) that the polyether agent does not literally include ether functional groups.

It is understood that terminal modifications can be incorporated into any of the polyether agents described herein to provide for a desirable property. Such terminal modifications can be achieved, e.g., by derivatizing a terminal hydroxy group (e.g., to form an ether, ester, or carbamate terminal modification), or by incorporating a terminal group, e.g., containing a functional group such as an amino group, carboxylic acid group, or acrylate group, that can be optionally further derivatized (e.g., as an amide, carbamate, ester, or hydroxylamine). In some cases, the terminal group includes a chemoselective functional group that is suitable for conjugating to a molecule of interest. Accordingly, terminal groups of interest include, but are not limited to, acrylate (—COCH=CH$_2$), acetate (—COCH$_3$), —OCH$_2$COOH, —NHCH$_2$CH$_2$COOH, —NHCH$_2$COOH, —OCH$_2$CH$_2$COOH, —COCH$_2$CH$_2$COOH, —COCH$_2$NH$_2$, and the like.

In some embodiments, the polyether agent is of Formula (I):

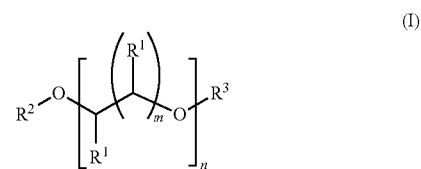

wherein:
  m is 1-3;
  n is 1-30;
  each $R^1$ is independently H or methyl; and
  $R^2$ and $R^3$ are each independently H, alkyl or a terminal group. In some embodiments of Formula (I), each monomeric unit of the polyether agent includes a single $R^1$ group that is methyl, where the other $R^1$ groups are H. Accordingly, in some cases, the polyether agent of formula (I), can include different isomers or isomeric forms. An isomer or isomeric form refers to an alternative for of a polyether agent having monomeric units with the same number of carbon and oxygen atoms, but a different configuration as compared to the parent form of the polyether agent. In some embodiments, the polyether agents (e.g., as described herein) include a mixture of individual molecules, e.g., polyether agents of different lengths and/or having different isomeric forms. For example, polypropylene glycols such as dipropylene glycol can include a mixture of isomers (e.g., as described herein).

In some embodiments, the polyether agent is of Formula (Ia):

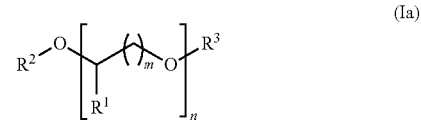

wherein:
  m is 1-3;
  n is 1-30;
  $R^1$ is H or methyl; and
  $R^2$ and $R^3$ are each independently H, alkyl, or a terminal group.

In certain embodiments of Formula (I)-(Ia), $R^2$ and $R^3$ are each H. In certain embodiments of Formula (I)-(Ia), $R^2$ and $R^3$ are each alkyl, such as $C_{(1-6)}$ alkyl. In some cases, $R^2$ and $R^3$ are each methyl.

In certain embodiments of Formula (I)-(Ia), $R^1$ is H. In certain embodiments of Formula (I)-(Ia), $R^1$ is methyl.

5.3.2. (Poly)ethylene Glycol Agents

The disclosure provides various (poly)ethylene glycol (PEG)-based sensing solutions that can be used for detection or characterization of a biomolecule in a sample using a nanopore device. In some embodiments of Formula (I)-(Ia), where m is 1 and $R^1$ is H, the polyether agent can be referred to as ethylene glycol (n=1) or (poly)ethylene glycol.

In some embodiments of Formula (I)-(Ia), the polyether agent is of Formula (II):

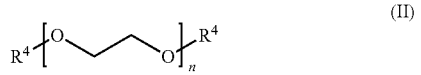

(II)

where n is 1-30; and each $R^4$ is independently H, alkyl or a terminal group.

In some embodiments of Formula (II), each $R^4$ is H. In some embodiments of Formula (II), each $R^4$ is alkyl, such as C(1-6) alkyl. In some cases, each $R^4$ is methyl. In some embodiments of Formula (II), n is 2-30, such as 3-30, 4-30, 5-30, 6-30, 7-30, 8-30, 10-30, or 10-20. In some embodiments of Formula (II), n is 1. In some embodiments of Formula (II), n is 2-25, such as 2-20, 2-18, 2-16, 2-15, 2-14, 2-13, 2-12, 2-10, 2-8 or 2-6.

In some embodiments of Formula (II), n is 1 and each $R^4$ is H (e.g., ethylene glycol). In some embodiments of Formula (II), n is 2 and each $R^4$ is H (e.g., diethylene glycol). In some embodiments of Formula (II), n is 3 and each $R^4$ is H (e.g., triethylene glycol). In some embodiments of Formula (II), n is 1 and each $R^4$ is methyl. In some embodiments of Formula (II), n is 2 and each $R^4$ is methyl. In some embodiments of Formula (II), n is 3 and each $R^4$ is methyl. In some embodiments of Formula (II), n is 4 and each $R^4$ is H (e.g., tetraethylene glycol). In some embodiments, of Formula (II), n is 4 and each $R^4$ is methyl (e.g., tetraethylene glycol dimethyl ether).

In some embodiments of Formula (II), the polyether agent is a (poly)ethylene glycol or (poly)ethylene glycol ether having a molecular weight in the range of about 120 to 3000. In some embodiments of Formula (II), the polyether has a molecular weight of 3000 or less, such as, 2500 or less, 2000 or less, 1500 or less, or 1000 or less. It is understood that any of the molecular weights described herein can refer to an average molecular weight due to polydispersity of polyether agents, i.e., such polymers can include molecules with a distribution of molecular weights that can depends on their method of preparation. In some embodiments of Formula (II), the polyether agent has a molecular weight in the range of 100-120, 120-140, 140-160, 160-180, 180-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2200, 2200-2400, 2400-2600, 2600-2800, 2800-3000, 3000-4000, 4000-5000, 5000-6000, 6000-7000, or 7000-8000. It is understood that the size or molecular weight of the particular polyether agent selected for use in the sensing solution can be tailored to provide a desirable sensitivity or accuracy of detection and depends on a variety of conditions, such as the target analyte (e.g., biomolecule), the analyte probe (if utilized) and probe's physical characteristics or chemistry.

In some embodiments of Formula (II) the polyether agent is PEG 120-160 molecular weight. In some embodiments of Formula (II), the polyether agent is PEG 160-200 molecular weight. In some embodiments of Formula (II), the polyether agent is PEG 200-400 molecular weight. In some embodiments of Formula (II), the polyether agent is PEG 200-600 molecular weight. In some embodiments of Formula (II), the polyether is PEG 3000 molecular weight or less.

5.3.3. (Poly)Propylene Glycol Agents

The disclosure provides various sensing solutions comprising (poly)propylene glycol (PPG) for the detection and characterization of a biomolecule in a sample using a nanopore device. In some embodiments of Formula (I)-(Ia), where m is 1 and one $R^1$ is methyl, the polyether agent can be referred to as propylene glycol (n=1) or (poly)propylene glycol.

In some embodiments of Formula (I), the polyether agent is of Formula (III):

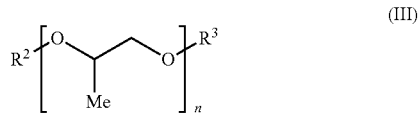

(III)

where n is 1-30; and $R^2$ and $R^3$ are each independently H, alkyl or a terminal group.

In some embodiments of Formula (III), $R^2$ and $R^3$ are each H. In some embodiments of Formula (III), each $R^2$ and $R^3$ are each alkyl, such as C(1-6) alkyl. In some cases, $R^2$ and $R^3$ are each methyl. In some embodiments of Formula (III), n is 2-30, such as 3-30, 4-30, 5-30, 6-30, 7-30, 8-30, 10-30, or 10-20. In some embodiments of Formula (III), n is 1. In some embodiments of Formula (III), n is 2-25, such as 2-20, 2-18, 2-16, 2-15, 2-14, 2-13, 2-12, 2-10, 2-8, or 2-6.

In some embodiments of Formula (III), n is 2, and $R^2$ and $R^3$ are each H (e.g., dipropylene glycol). In some embodiments of Formula (III), n is 3, and $R^2$ and $R^3$ are each H (e.g., tripropylene glycol). In some embodiments of Formula (III), n is 3, one of $R^2$ and $R^3$ is H, and the other of $R^2$ and $R^3$ is methyl. In some embodiments of Formula (III), n is 3, and $R^2$ and $R^3$ are each methyl (e.g., tripropylene glycol dimethyl ether). In certain embodiments, the polyether agent is dipropylene glycol. It is understood that polypropylene glycols (e.g., dipropylene glycol) can include different isomeric forms. Dipropylene glycol can be present in one or more isomers, 4-oxa-2,6-heptandiol, 4-oxa-1,6-heptandiol, 2-(2-hydroxy-propoxy)-propan-1-ol, and/or 2-(2-hydroxy-1-methyl-ethoxy)-propan-1-ol. In some cases, the dipropylene glycol utilized is a mixture of 4-oxa-2,6-hexandiol and 4-oxa-1,6-hexandiol.

In some embodiments of Formula (I), the polyether agent is of Formula (IIIa) and/or (IIIb):

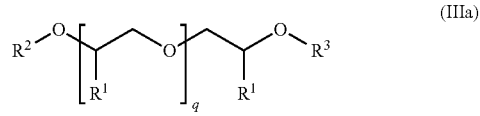

(IIIa)

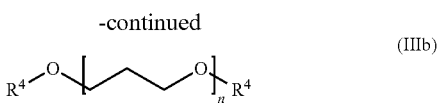

(IIIb)

where n is 1-30, q is 1-29; each $R^1$ is methyl; and $R^2$ and $R^3$ and each $R^4$ are each independently H, alkyl or a terminal group.

In some embodiments of Formula (IIIa), $R^2$ and $R^3$ are each H. In some embodiments of Formula (IIIa), each $R^2$ and $R^3$ are each alkyl, such as C(1-6) alkyl. In some cases, $R^2$ and $R^3$ are each methyl. In some embodiments of Formula (IIIa), q is 2-29, such as 3-29, 4-29, 5-29, 6-29, 7-29, 8-29, 10-29, or 10-20. In some embodiments of Formula (IIIa), q is 1. In some embodiments of Formula (IIIa), q is 2-25, such as 2-20, 2-18, 2-16, 2-15, 2-14, 2-13, 2-12, 2-10, 2-8, or 2-6. In some embodiments of Formula (IIIb), each $R^4$ is H. In some embodiments of Formula (IIIb), each $R^4$ is alkyl, such as C(1-6) alkyl. In some cases, each $R^4$ is methyl. In some embodiments of Formula (IIIb), n is 2-30, such as 3-30, 4-30, 5-30, 6-30, 7-30, 8-30, 10-30, or 10-20. In some embodiments of Formula (IIIb), n is 2. In some embodiments of Formula (IIIb), n is 2-25, such as 2-20, 2-18, 2-16, 2-15, 2-14, 2-13, 2-12, 2-10, 2-8, or 2-6.

In some embodiments of Formula (IIIa), q is 1, and $R^2$ and $R^3$ are each H (e.g., dipropylene glycol). In some embodiments of Formula (IIIa), q is 2, and $R^2$ and $R^3$ are each H (e.g., tripropylene glycol). In some embodiments of Formula (IIIa), q is 2, one of $R^2$ and $R^3$ is H, and the other of $R^2$ and $R^3$ is methyl. In some embodiments of Formula (IIIa), q is 2, and $R^2$ and $R^3$ are each methyl (e.g., tripropylene glycol dimethyl ether). In some embodiments of Formula (IIIb), n is 2, and each $R^4$ are each H (e.g., dipropylene glycol). In some embodiments of Formula (IIIb), n is 3, and each $R^4$ is H (e.g., tripropylene glycol). In some embodiments of Formula (IIIb), n is 3, one $R^4$ is H, and the other $R^4$ is methyl. In some embodiments of Formula (IIIb), n is 3, each $R^4$ is methyl (e.g., tripropylene glycol dimethyl ether).

In certain embodiments, the polyether agent is dipropylene glycol. In certain embodiments, the polyether agent is tripropylene glycol. It is understood that polypropylene glycols (e.g., di- or tri-propylene glycol) can include different isomeric forms. Dipropylene glycol can be present in one or more isomers, 4-oxa-2,6-heptandiol, 4-oxa-1,6-heptandiol, 2-(2-hydroxy-propoxy)-propan-1-ol, and/or 2-(2-hydroxy-1-methyl-ethoxy)-propan-1-ol. In some cases, the dipropylene glycol utilized is a mixture of 4-oxa-2,6-hexandiol and 4-oxa-1,6-hexandiol.

In some embodiments of Formula (III)-(IIIb), the polyether agent is a (poly)propylene glycol or (poly)propylene glycol ether having a molecular weight in the range of about 120 to 3000. In some embodiments of Formula (III)-(IIIb), the polyether has a molecular weight of 3000 or less, such as, 2500 or less, 2000 or less, 1500 or less, or 1000 or less. In some embodiments of Formula (III)-(IIIb), the polyether agent has a molecular weight in the range of 100-120, 120-140, 140-160, 160-180, 180-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2200, 2200-2400, 2400-2600, 2600-2800, 2800-3000, 3000-4000, 4000-5000, 5000-6000, 6000-7000, or 7000-8000.

In some embodiments of Formula (III)-(IIIb), the polyether agent is PPG 120-160 molecular weight. In some embodiments of Formula (III)-(IIIb), the polyether agent is PPG 160-200 molecular weight. In some embodiments of Formula (III)-(IIIb), the polyether agent is PPG 200-400 molecular weight. In some embodiments of Formula (III)-(IIIb), the polyether agent is PPG 200-600 molecular weight. In some embodiments of Formula (III), the polyether is PPG 3000 molecular weight or less.

5.3.4. (Poly)butylene Glycol Agents

In some embodiments of Formula (I), where m is 2-3 and $R^1$ is methyl or H, the polyether agent can be referred to as butylene glycol (n is 1) or (poly)butylene glycol. The polyether agent can be a (poly)-1,4-butylene glycol ($R^1$ is H) or a (poly)-1,3-butylene glycol ($R^1$ is methyl). The disclosure provides various sensing solutions including such (poly)butylene glycols for the detection and characterization of a biomolecule in a sample using a nanopore device.

In some embodiments of Formula (I), the polyether agent is of Formula (IV):

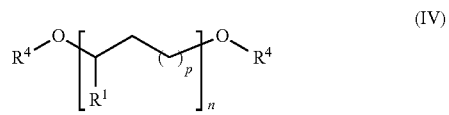

(IV)

where: p is 1 or 2; n is 1-30; $R^1$ is H or methyl; and each $R^4$ is independently H, alkyl or a terminal group.

In some embodiments of Formula (IV), each $R^4$ is H. In some embodiments of Formula (IV), each $R^4$ is alkyl, such as $C_{(1-6)}$ alkyl. In some cases, each $R^4$ is methyl. In some embodiments of Formula (IV), n is 2-30, such as 3-30, 4-30, 5-30, 6-30, 7-30, 8-30, 10-30, or 10-20. In some embodiments of Formula (IV), n is 1. In some embodiments of Formula (IV), n is 2-25, such as 2-20, 2-18, 2-16, 2-15, 2-14, 2-13, 2-12, 2-10, 2-8 or 2-6.

In some embodiments of Formula (IV), when p is 1, $R^1$ is methyl. In some embodiments of Formula (IV), when p is 2, $R^1$ is H. In some embodiments of Formula (IV), n is 1. In some embodiments of Formula (IV), the polyether agent is 1,3-butylene glycol or 1,4-butylene glycol.

In some embodiments of Formula (IV), the polyether agent is a (poly)butylene glycol or (poly)butylene glycol ether having a molecular weight in the range of about 120 to 3000. In some embodiments of Formula (IV), the polyether has a molecular weight of 3000 or less, such as, 2500 or less, 2000 or less, 1500 or less, or 1000 or less. In some embodiments of Formula (IV), the polyether agent has a molecular weight in the range of 100-120, 120-140, 140-160, 160-180, 180-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2200, 2200-2400, 2400-2600, 2600-2800, 2800-3000, 3000-4000, 4000-5000, 5000-6000, 6000-7000, or 7000-8000.

5.3.5. (Poly)Alkylene Glycol Ether Agents

As described above, aspects of the polyether agents of formulae (I)-(IV) include linear polymers terminated with alkoxy groups, i.e., where in Formula (I)-(Ia), $R^2$ and $R^3$ are each alkyl, such as $C_{(1-6)}$ alkyl. When the polyether agent of formula (I)-(Ia) is a linear polymer, it can be referred to as a (poly)alkylene glycol or (poly)alkylene glycol ether. In some embodiments of formula (I)-(IV), the polyether is a (poly)alkylene glycol ether, i.e., where the terminal groups of the polymer are alkyl ether groups. In some embodiments of formula (I)-(IV), the polyether is a (poly)alkylene glycol dimethyl ether. In some embodiments of formula (I)-(IV), the polyether is a (poly)alkylene glycol diethyl ether. In some embodiments of formula (II), the polyether is a (poly)ethylene glycol dimethyl ether. In some embodiments of formula (III)-(IIIb), the polyether is a (poly)propylene glycol dimethyl ether. In some embodiments of formula (IV), the polyether is a (poly)1,4-butylene glycol dimethyl ether. In some embodiments of formula (IV), the polyether is a (poly)1,3-butylene glycol dimethyl ether.

In certain embodiments, the disclosure provides sensing solution with an effective amount of an acetate, an acrylate, such as poly(ethylene glycol) methyl ether acrylate (CAS 32171-39-4) or the like.

5.3.6. Cation-Salt Agents

The disclosure provides cation-salt agents for the detection and characterization of a biomolecule using a nanopore device. The cation-salt agents of the disclosure are used in sensing solutions at an effective amount to provide enhanced detection and resolution of a biomolecule using a nanopore device. A person skilled in the art would understand that the term "salt agents" can be used interchangeably with the term "electrolytes".

The disclosure provides various sensing solutions comprising an effective of at least one monovalent cation or monovalent cation salt. In some embodiments, the monovalent cation can be Li, Na. K, or Cs. In some embodiments, the monovalent cation salt is CsCl, LiCl, NaCl, or KCl. A monovalent cation or a monovalent cation salt can be used in a sensing solution at various molar concentration depending on the biomolecule to be detected. In some embodiments, the monovalent cation or monovalent cation salt can have a total concentration in a sensing solution of about 0.5M, about 1M, about 1.5M, about 2M, about 2.5M, about 3M, about 3.5 M, about 4 M, about 5M, or about 6 M.

The disclosure also provides various sensing solutions comprising an effective of at least one divalent cation or a or divalent cation salt. In some embodiments, the divalent cation can be $Ca^{2+}$ or $Mg^{2+}$. In some embodiments, the divalent cation salt is $MgCl_2$ or $CaCl_2$. In some embodiments, the divalent cation or the divalent cation salt can have a total concentration in a sensing solution of about 0.5M, about 1M, about 1.5M, about 2M, about 2.5M, about 3M, about 3.5 M, about 4 M, about 5M, or about 6M CsCl Agents The disclosure provides various sensing solutions compositions comprising a CsCl agent for the detection and characterization of a biomolecule using a nanopore device. The CsCl agent can comprise an effective amount in a sensing solution.

The effective amount of a CsCl agent will depend on the biomolecule, method or application used. In some embodiments, an effective amount of CsCl agent is about 0.5, about 1M, about 1.5M, about 2M, about 2.5M, about 3M, about 3.5 M or about 4 M.

The CsCl agents provided by the disclosure can be applied at various concentration in order to form a gradient sensing solution across a membrane in a nanopore device. For example, a higher concentration of CsCl can be applied to the cis chamber and a lower concentration of CsCl can be applied to a trans chamber. Some non-limiting examples include 1M/0.5M CsCl, 2M/1M CsCl, or 3M/1.5M CsCl. In another embodiment, a lower concentration of CsCl can be applied to the cis chamber and a higher concentration of CsCl can be applied to a trans chamber.

$CaCl_2$ Agents

The disclosure provides various sensing solutions compositions comprising a $CaCl_2$ agent for the detection and characterization of a biomolecule using a nanopore device. The $CaCl_2$ agent can comprise an effective amount in a sensing solution.

The effective amount of a $CaCl_2$ agent will depend on the biomolecule, method or application used. In some embodiments, an effective amount of $CaCl_2$ agent is about 0.5, about 1M, about 1.5M, about 2M, about 2.5M, about 3M, about 3.5 M or about 4 M.

The $CaCl_2$ agents provide by the disclosure can be applied as a gradient sensing solution across a membrane of a nanopore device. In some embodiments, a higher concentration of $CaCl_2$ can be applied to the cis chamber and a lower concentration of $CaCl_2$ can be applied to a trans chamber. Non-limiting examples of gradient concentrations include 1M/0.5M $CaCl_2$, 2M/1M $CaCl_2$, or 3M/1.5M $CaCl_2$. In other embodiments, a lower concentration of $CaCl_2$ can be applied to the cis chamber and a higher concentration of $CaCl_2$ can be applied to a trans chamber.

5.3.7. Effective Amount

The effective amount of the polyether agent in a sensing solution will depend on the application, biomolecule, or method used.

Often the effective amount allows for increase accuracy in the detection or characterization of a biomolecule in a nanopore device. See non-limiting ways to achieve increased accuracy using the sensing solutions of the disclosure described in Section 5.3.9.

In some embodiments, the effective amount of a polyether agent (e.g., as described herein) in a sensing solution is: about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% v/v. In some embodiments, the effective amount of a polyether agent in a sensing solution is 30% v/v.

In some embodiments, the effective amount of a polyether agent (e.g., as described herein) in a sensing solution is: about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight. In some embodiments, the effective amount of a polyether agent in a sensing solution is 30% or less by weight of a polyether agent (e.g., as described herein).

Like the polyether agent, the effective amount of a $CaCl_2$ or CsCl agent will also depend on the biomolecule, method, or application used.

In some embodiments, the effective amount of a $CaCl_2$ or CsCl agent is about 0.5, about 1M, about 1.5M, about 2M, about 2.5M, about 3M, about 3.5 M or about 4 M. In some embodiments, a combination of any one of these molar concentrations can be used to apply a gradient in an effective amount for the characterization or detection of a biomolecule in a nanopore device.

5.3.8. Additional Agents

A sensing solution can comprise any other agent or chemical known to be in a buffer. As it will be appreciated by one skilled in the art, non-limiting example that can be included in a sensing solution of the disclosure include, buffering solutions, salts, and chelating agents, a carbohydrate, or sugar. It is contemplated that any one of the additional agents can be optimized (e.g., for a concentration) with the sensing solutions using standard screening methods for nanopore detection.

It is contemplated that a divalent or a monovalent cation or a salt can be added to a sensing solution of the disclosure. Non-limited examples of cations or salts that can be added as an additional agent to a sensing solution are: LiCl, NaCl, KCl, $MgCl_2$, CsCl, $CaCl_2$), Li, Na, K, Mg, Cs, Ca, or a combination thereof. These salts can be added as various concentrations. For example, an additional salt agent can be used at a molar concentration of greater than 0.01M, 0.02M, 0.05M, 0.1M, 0.2M, 0.5M, 1M, 1.5M, 2M, 2.5M, 3M, 3.5M, 4M, 4.5M, or 5M, or any concentration that works with the sensing solution to increase accuracy.

In some embodiments, the sensing solution of the disclosure can comprise a chelating agent. Chelating agents that can be added to a sensing solution as described herein, include but are not limited to, EDTA, EGTA, or any other chelating agent known in the art. A cheating agent can be added to a sensing solution at different concentrations. For example, the chelating agent can be used at a molar concentration of greater than 0.01M, 0.02M, 0.05M, 0.1M, 0.2M, 0.5M, 1M, 1.5M, 2M, or any concentration that works with the sensing solution to increase accuracy.

A buffer solution can also can be added to a sensing solution of the disclosure. Non-limiting examples of buffer solutions that can be added to a sensing solution are a TRIS-HCl, a Borate, a CHES, a Bis-tris propane, a CAPS, a potassium phosphate, a TRIS, or a HEPES. The buffer solution can be added at various concentrations. For example, the buffer solution can be added to the sensing solution at a molar concentration of greater than 0.01M, 0.02M, 0.05M, 0.1M, 0.2M, 0.5M, 1M, 1.5M, 2M, 2.5M, 3M, 3.5M, 4M, 4.5M, 5M, 6M, 7M, 9M, 10M, 11 M, or any concentration that works with the sensing solution to increase accuracy.

Also, depending on the application, biomolecule, or method used a sensing solution of the disclosure can also omit certain agents.

In some applications, a sensing solution will not comprise glycerol.

In some applications, a sensing solution will not comprise a PEG greater than 7000. In some applications, a sensing solution provided of the disclosure will not comprise a PEG 8000.

5.3.9. Increased Accuracy

The sensing solutions of the disclosure provide increased accuracy in the detection and characterization of a biomolecule using a nanopore device as compared to a standard buffer. Increased accuracy using the sensing solutions of the disclosure will depend on the type of biomolecule, method, application or characteristic to be determined.

In some embodiments, increased accuracy can be the detection of a biomolecule or a modification thereof that would otherwise not be detected in a standard buffer.

In some applications, increased accuracy can be detection of a substantial number of events of the molecule passing through a pore in a standard buffer. A substantial number of events can be 100, 200, 300, 400, 500, 600, 700, 800, 900, 1000, 1100, 1200, 1300, 1400, 1500, 1600, 1700, 1800, 1900, or 2000 after a reasonable amount of time.

A reasonable amount of time will depend on the level of background molecules (e.g., non-target molecules) in a sample. For example, if the nucleic acid or protein is known to be rare in a sample, such as a biomarker from a stem cell, then a reasonable amount of will be longer in comparison to sample that was substantially purified for a stem cell population. In some embodiments, a reasonable amount of time will be about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mins. In some embodiments, a reasonable amount of time will be about 1, 2, 3, 4, 5, 6, 7, 8, 9, or 10 mins.

In some applications, increased accuracy can be determining one or more characteristic of a biomolecule (e.g., length, size, structure, concentration, modification, etc.) that would otherwise not be detected in a standard buffer.

In some applications, increased accuracy can be resolving the difference in length of two or more biomolecules in a sample that have a similar length. In some embodiments, increased accuracy can be discrimination of different length or sizes of the biomolecule in the sample. In some embodiments, the discrimination is between length differences of less than 50 bp, 100 bp, 150 bp, 200 bp, 250 bp, 300 bp, 350 bp, 400 bp, 450 bp, or 500 bp.

In some embodiments, increased accuracy can be the discrimination of different sizes of the biomolecule in the sample. In some embodiments, the discrimination between different sizes of biomolecules can be a difference of less than 10, 20, 30, 40, 50, 60, 70, 80, 90, or 100 kDa in size. In some embodiments, the discrimination is between different sizes of biomolecules can be more than 10, 20, 30, 40, 50, 60, 70, 80, 90, or 100 kDa.

In some applications, increased accuracy can be resolving the difference in structure of two or more biomolecules in a sample that have a similar structure. In some applications, increased accuracy can be resolving the difference in structure of two or more proteins in a sample that have a similar structure. In some applications, increased accuracy can be resolving the difference in structure of two or more nucleic acids in a sample that have a similar structure.

In some applications, increased accuracy can be resolving the difference in chemical modification of two or more biomolecules in a sample that have a similar modification (e.g., in charge, length, and/or size).

In some applications, increased accuracy can be resolving the number of modifications on a protein or a nucleic acid.

In some applications, increased accuracy can be resolving the presence or absence of a modification on a protein or a nucleic acid. Non-limiting examples of modifications that can be detected or characterize on a biomolecule include but are not limited to: methylation, phosphorylation, acetylation, and the like.

5.3.10. Standard Buffers

A standard buffer used to determine increased accuracy in comparison to a sensing solution provided herein can be any nanopore buffer, running buffer, or sensing buffer known in the art. Depending on the type of biomolecule, method, application or characteristic to be determined the standard buffer composition will differ.

In some embodiments, a standard nanopore buffer can comprises an effective amount of LiCl, KCl, or NaCl or a monovalent buffer thereof. An "effective amount" of a standard buffer is one that allows the biomolecule to translocate through a pore at a reasonable rate, but does not result in increased detection, resolution, or characterization of a biomolecule to two or more biomolecules with similar physical properties.

In some embodiments, the standard buffer comprises LiCl, KCl, NaCl or a monovalent ion thereof is can have a molar concentration of less than 0.5M, 1M, 2M, 3M, 4M, or 5M. In some embodiments, a standard buffer is 4.0M LiCl, 10 mM Tris HCl pH 8.8, 1 mM EDTA.

In some embodiments, the standard buffer does not comprise a polyether agent of the disclosure. In some embodiments, the standard buffer does not comprise an effective amount of a polyether of Formula (II)-(IV).

In some embodiments, the standard buffer can further comprise one or more buffering chemicals or agents. Buffering chemicals or agents used in a standard buffer can include, but are not limited to, Tris, Tris-HCL, Borate, CHES, Bis-tris propane, CAPS or others known in the art.

In some embodiments, the standard buffer can further comprise a chelating agent. Chelating agents that can be included in a standard buffer include, but are not limited to, EDTA, EGTA, or others known in the art. In some applications, the standard buffer can comprise a chelating agent at concentration less than 0.5 mM, 1 mM, 2 mM, 3 mM, or 4 mM. In some applications, the standard buffer can comprise a chelating agent at concentration greater than 0.5 mM, 1 mM, 2 mM, 3 mM, or 4 mM.

In some embodiments, a standard buffer will comprise a PEG greater than 3000, 4000, 5000, 6000, or 7000 in molecular weight. In some embodiments, a standard buffer will comprise a PEG 8000 molecular weight. In some, embodiments the standard buffer comprises an effective amount of glycerol.

Often the standard buffer does not comprise an effective amount of a polyether agent in an effective amount. In some embodiments, the standard buffer does not comprise an effective amount of Formula (I) or its embodiments; Formula (II) or its embodiments; Formula (III) or its embodiments, Formula (IV) or its embodiments, or a combination thereof.

5.4. Methods

The disclosure provides various methods for the detection and characterization of a biomolecule in a sample using a nanopore device.

The methods of the disclosure are particularly useful for detecting and resolving biomolecules in a sample that have similar physical characteristics such as length, charge, structure, concentration, or combination thereof and that would otherwise not be detected, resolved from one another, or be able to be characterized using a standard buffer in a nanopore device. Standard buffer can include any nanopore buffer known in the art as well as the buffers described in Section 5.3.10.

The methods provided by the disclosure also provide increased accuracy in detection or characterization as compared to the same method performed in a standard buffer. Standard buffer can include any nanopore buffer known in the art as well as the buffers provided in Section 5.3.10.

Often, the methods of the disclosure will use a current signature from a target molecule or a target molecule that has been modified to enhance detection (e.g., probe, label, dye or voltage-sensitive moiety). A current signature can include one feature or more than one feature. Non-limiting examples of current signature features, include but are not limited to, calculated event dwell time, mean event amplitude, maximum event amplitude, median event amplitude, event area or others known in the art. One skilled in the art would appreciate that a signature could also include any combination calculated event dwell time, mean event amplitude, maximum event amplitude, median event amplitude, or event area. In some embodiments, multiple signatures may also exist within an event to enhance discrimination between molecule types. In some embodiments, a current signature is a collection of current measurements. In some embodiments, a current signature is a pattern identified within a detected event.

In some embodiments, the method for detecting or characterizing a biomolecule in a sample comprises the following steps: (a) contacting a sample suspected of comprising a biomolecule with any one of the sensing solutions of the disclosure, wherein the sensing solution is contacting a nanoporous membrane, and wherein the nanoporous membrane separates the space of a device into a cis volume and a trans volume; (b) applying a voltage across a nanopore of the nanoporous membrane, thereby inducing translocation of the biomolecule through the nanoporous membrane; and (c) detecting a current during the translocation of the biomolecule, if present; and if present detecting or characterizing the biomolecule, wherein the cis volume and the trans volume comprise the same sensing solution.

In some embodiments, the method for detecting or characterizing a biomolecule in a sample comprises the following steps: (a) contacting a sample suspected of comprising a biomolecule with any one of the sensing solutions of the disclosure, wherein the sensing solution is contacting a nanoporous membrane, and wherein the nanoporous membrane separates the space into a cis volume and a trans volume; (b) applying a voltage across a nanopore of the nanoporous membrane thereby inducing translocation of the biomolecule through the nanoporous membrane; and (c) detecting a current during the translocation of the biomolecule, if present; and if present detecting or characterizing the biomolecule, wherein the cis volume and the trans volume comprise a sensing solution that are different from one another.

In some embodiments, the method for detecting or characterizing a biomolecule in a sample comprises the following steps: (a) contacting a sample suspected of comprising a biomolecule with any one of the sensing solutions of the disclosure, wherein the sensing solution is contacting a nanoporous membrane, and wherein the nanoporous membrane separates the space into a cis volume and a trans volume; (b) applying a voltage across a nanopore of the nanoporous membrane thereby inducing translocation of the biomolecule through the nanoporous membrane; and (c) detecting a current during the translocation of the biomolecule, if present; and if present detecting or characterizing the biomolecule, wherein the cis volume and the trans volume comprise a gradient sensing solution that are different from one another by molar concentration.

Depending on the application, the type of current applied can be tailored for the application. For example, if sequencing by base detection is desired, a tunneling current can be used with the methods provided herein. In certain embodiments, a sequencing method can use an ionic current can be used.

The disclosure provides methods for determining the presence or absence of a protein or nucleic acid in a sample. That is, the methods are applied to determine is a particular target protein or target nucleic acid is present in a sample. Such a method can be applied to a diagnostic application where one is looked for a unique biomarker or mutation. This method can also be applied to infectious disease screening where a sample is being tested for the presence of a protein or gene that is indicative of a particular microbe, virus, or microorganism or a host infection marker.

The disclosure provides methods for determining the quantity of a protein or a nucleic acid. In some embodiments, the quantity can be the number of molecules or the copy number of a genetic locus, such as a transgene insertion (e.g., genetically modified organisms), a translocation, an insertion, or a deletion. This method can be applied to various screening applications such as, screening for a particular genomic mutation in a human, copy number of a certain chromosome or genetic locus known to be linked to a disease state, a somatic mutation in a cancer biopsy, or screening for a transgene insertion in a plant or agricultural sample.

In some embodiments, the methods provided herein can be used to determine the identity of a protein or a nucleic acid. The identity can be determined by sequencing or by detection of a probe or an any other molecular modification known in the art that alters a physical characteristic that is known to change current (e.g., a voltage-sensitive moiety). This method can be effective for various screening applications such as, screening for small genetic mutations such as single nucleotide polymorphism, small insertional or deletion mutations, precision mutations by CRISPR, or expression of a particular protein binding domain.

The disclosure provides methods for the detection and characterization a modification of a protein or a nucleic acid. Examples of modifications that can be used with the methods of the disclosure, include but are not limited to, methylation, acetylation, phosphorylation and the like. The method can be applied to determine is a particular protein is activated in a sample by its phosphorylation status at a certain residue of interest, the state of the chromatin at a certain locus, the methylation acetylation, phosphorylation status of a tumor suppressor or oncogene.

The disclosure provides methods to determine a structure of a protein or a nucleic acid. Examples of structures that can be used with the disclosure, include but are not limited to, a hairpin, a beta sheet, an alpha helix, or structure made from DNA origami techniques (e.g. DNA knot and the like), The disclosure provides methods for determining a sequence of a protein or a nucleic acid. In some embodiments, the method can determine the sequence determining a nucleic acid base or amino acid reside in a polynucleotide or a polypeptide. In some embodiments, the method can determine the sequence by a base-pair (e.g., C-G, A-T, etc). In some embodiments, the method can determine the sequence by the identification of a segment using method which include the use of a probe as provided herein.

The disclosure provides methods for determining two or more of the following characteristics: a presence or absence, quantity, identity, modification, structure, concentration, or a sequence of a biomolecule.

The methods provided by the disclosure may also be automated in whole or in part.

5.4.1. Samples

The disclosure provides methods for detecting or characterizing a biomolecule from a sample. As skilled artisan will appreciate, a sample can substantially comprise one biomolecule depending on the source of the sample or the processing or treatment of the sample. However, in certain applications a sample will comprise several different biomolecules types.

The biomolecule itself or aspect of the biomolecule being characterized may be highly sensitive to nanopore detection and may not require extensive sample processing or treatment, such as amplification, isolation, and derivatization and the like. However, for some biomolecules sample processing or treatment will be needed, such as amplification (e.g., PCR amplification or by plasmid replication), isolation, and derivatization, or detection probes and labeling can be used in concert with the methods, systems, and kits of the disclosure.

Examples of samples that can be used with the methods of the disclosure include, but are not limited to a biological sample, a clinical sample, an environmental sample (e.g., air, water, agricultural, or soil) or an agricultural sample (e.g., plant, algae, or fungus).

The sample used with the methods provided herein can be from a subject. The subject can be an animal, a plant, or a human.

The animal can be a bird, e.g., a chicken. The animal can be a mammal. The mammal can be, e.g., a dog, cat, horse, cow, mouse, rat, or pig. The mammal can be a primate, e.g., a human, chimpanzee, orangutan, or gorilla.

The human can be a male or female. In some embodiments, the sample can be from a human embryo or human fetus. In some embodiments, the sample can be from a specific organ type of a human or animal, such as, for example: heart, skin, liver, lung, breast, stomach, pancreas, bladder, colon, intestine, gall bladder, or brain.

The sample can be from a subject who has a specific disease, disorder, or condition, or is suspected of having (or at risk of having) a specific disease, disorder or condition. Examples of disease, disorder, or condition include, but are not limited to, a genetic disease, a proliferative disease, such as cancer, an aging condition, or an infectious disease.

The sample can be obtained from various sources that comprise nucleic acids or protein or peptide or fragments thereof (such as cell-free DNA). Examples of sample sources that can be used with the disclosure include but are not limited to: aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, perspiration, tears, vaginal secretion, vomit, feces, or urine.

The sample can also be obtained from a cell line (e.g., primary or cultured), genomic DNA, cell-free plasma, formalin fixed paraffin embedded (FFPE) sample, or flash frozen tissue or blood sample.

5.4.2. Biomolecules

The term "biomolecules" included but are not limited to nucleic acids (e.g., DNA or RNA), proteins, peptides, antibodies, small molecules, aptamers, analytes, or drug agents. The biomolecule can also comprise one or more modifications. The biomolecules can be from a natural source. The biomolecules can be synthetically made.

As with samples, depending on the abundance of the biomolecule in a sample the method may include treatment or processing of the biomolecule in order to increase the abundance of the biomolecule before detection. In some embodiments, the biomolecule is substantially purified. Substantial purification of a biomolecule can be performed by using a crude purification method known in the art or a commercially available purification kit.

The biomolecules can be directly detected (with no other molecules) or indirectly detected by the use of a molecule probe, label (e.g., optical label, unique identifier or barcode), dye, or any other detection molecule know in the art.

The disclosure also provides methods for detection or characterization of a nucleic acid. The nucleic acid can be mitochondrial DNA, genomic DNA, mRNA, siRNA, miRNA, shRNA, cRNA, single-stranded DNA, double-stranded DNA, single-stranded RNA, double-stranded RNA, tRNA, rRNA, or cDNA. The nucleic acid can be fragmented. In some embodiments, the sample can comprise a hybrid polynucleotide is such a RNA/DNA hybrid, a PNA/DNA hybrid, or a RNA/PNA hybrid. In some embodiments, the polynucleotide is bound to a protein (e.g., an antibody or protein binding molecule).

The methods can be used to detect or characterize protein with various sizes. The nucleic acid can have a length of no more than 4 kb, 3 kb, 2 kb, 1 kb, 500 bp, 400 bp, 300 bp, 200 bp, or 100 bp. In some embodiments, the nucleic acids have a difference in length of less than about 1 kb, 500 bp, 400 bp, 300 bp, 200 bp, 100 bp, 50 bp, 30 bp, 20 bp, or 10 bp.

The disclosure also provides methods for detection a protein. A protein detected by the methods of the disclosure can be a full protein, peptide, small molecule or drug such an antibody, protein mimic or the like.

The methods can be used to detect or characterize a protein with various sizes from a range from about 10 kDa to up to 500 kDa. In some embodiments, the protein is at least 100-200 kDa, 200-300 kDa, 300-400 kDa, or 500-600 kDa.

Depending on the sensitivity of detection a biomolecule by a nanopore device the method can comprise modified of the biomolecule in order to enhance detection. Non-limiting examples of modifications that can be used with the methods of the disclosure include, linking the biomolecule to a voltage-sensitive moiety. A voltage-sensitive moiety can be a molecular modification known to alters a physical characteristic that is known to change current. Non-limiting examples of a molecular modification can include a dye, a molecular probe (linked through the conjugation of amino acid residue or nucleic acid complementary base-pairing or the like (e.g. PNA)), a bead, a molecular handle, a barcode, a unique identifier, or an optical label.

5.4.3. Sensing Solutions

It is contemplated that any of the sensing solution compositions provided by the disclosure, in Section 5.3, can be used in an effective amount with the methods provide by the disclosure. As discussed herein, a person skilled in the art would readily realize that additional agents can be added to a sensing buffer.

In some embodiments, the methods comprise the sensing solution compositions of Section 5.3 applied symmetrical, that is, comprising the same sensing solution is the cis and trans volumes of a nanopore device. In some embodiments, the methods comprise the sensing solution compositions of Section 5.3 applied asymmetrical, that is, comprising for example, either: a different sensing solutions in the cis volume and trans volume of a nanopore device; a sensing solution in the cis volume and a standard buffer in the trans volume; a sensing solution in the cis volume and an a carbohydrate solution in the trans volume, or the other way around.

It is contemplated that the compositions of the disclosure can be used in an effective amount with the methods, devices, systems, and kits provided herein. In some embodiments, the effective amount of a polyether agent as provided in Section 5.3.7.

Any of the polyether agents described herein can be utilized in a sensing solution. In some embodiments, the method can use a sensing solution comprising an effective amount of a polyether of Formula (I):

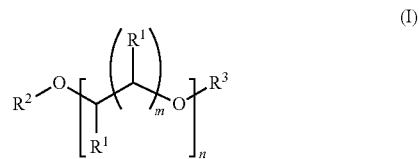

where: m is 1-3; n is 1-30; each $R^1$ is independently H or alkyl (e.g., methyl); and $R^2$ and $R^3$ are each independently H or alkyl (e.g., methyl) or a terminal group, wherein the sensing solution is capable of detecting or characterizing the biomolecule using a nanopore device.

In some embodiments, a method can comprise a sensing solution comprising an effective amount of a polyether of Formula (Ia)-(IV).

5.4.4. Asymmetric & Gradient Sensing Solutions

For some applications, it will be advantageous to use asymmetric sensing solutions for detection or characterization of a target molecule. In this method, a nanopore device comprises a nanoporous membrane that separates the interior space into a cis volume (e.g., a first volume) and a trans volume (e.g., a second volume) so that different sensing solutions can be applied to the device, e.g., to opposite sides of a nanoporous membrane. In some embodiments, an analyte (e.g., biomolecule) translocates through the nanoporous membrane from a first sensing solution in the cis volume to a second sensing solution in the trans volume. The analyte can be detected during translocation.

In an asymmetric sensing solution method, the device comprises a cis volume and a trans volume each which comprise a different composition in the cis volume and trans volume. For example, asymmetric sensing solution can have a sensing solution, a carbohydrate solution, or a standard buffer in a cis volume and a sensing solution, a carbohydrate solution, or a standard buffer in a trans volume so long as they are not the same.

In some embodiments, the device comprises a cis volume comprises a sensing solution described herein and trans volume comprises any standard buffer known in the art. In some embodiments, the device comprises a cis volume comprises a sensing solution described herein and trans volume comprises a standard buffer as described herein. In some embodiments, the device comprises a cis volume comprises a sensing solution described herein and trans volume comprises LiCl, KCl, in an effective amount. In some embodiments, the device comprises a cis volume comprises a sensing solution described herein and trans volume comprises 4.0M LiCl, 10 mM Tris HCl pH 8.8, 1 mM EDTA.

In some embodiments, the device comprises a cis volume comprising any one of the sensing solutions described herein and a trans volume comprising a carbohydrate solution. In some embodiments, the device comprises a cis volume comprising a carbohydrate solution and a trans volume comprising any one of the sensing solutions described herein.

Carbohydrate Solution

It is contemplated that a carbohydrate solution used asymmetrically in a nanopore device can increase accuracy of detection or characterization of some biomolecules. In some embodiments, the device comprises a cis volume comprising any one of the sensing solutions and the trans volume comprising carbohydrate solution.

A carbohydrate solution comprise can comprise Maltose, Glycerol, Sorbitol, Glucose, or Maltodextran. In some embodiments, the carbohydrate solution comprises at least 1%, 2%, 3%, 4%, 5%, 6%, 7%, 8%, 9%, 10, 1%, 12%, 13%, 14%, 15%, 16%, 17%, 18%, 19%, 20%, 21%. 22%, 23%. 24%, 25%, 26%, 27%, 28%, 29%, or 30% v/v. In a preferred embodiment, the trans volume comprises Maltose at least 1%, 2%, 3%, 4%, 5%, 6%, 7%, 8%, 9%, 10%, 11%, 12%, 13%, 14%, 15%, 16%, 17%, 18%, 19%, 20%, 21%. 22%, 23%, 24%, 25%, 26%. 27%, 28%, 29%, or 30% v/v.

In some embodiments, the device comprises a cis volume comprising a PEG 200 sensing solution and the trans volume comprising carbohydrate solution. In some embodiments, the device comprises a cis volume comprising a PEG 200 sensing solution and the trans volume comprising a Maltose carbohydrate solution.

Polyether Gradient Sensing Solutions

In some embodiments, a method of characterizing a sample with respect to a target biomolecule, comprising: providing a sample suspected of comprising a target biomolecule; loading said sample into a first volume of a nanopore device, wherein said nanopore device comprises a layer that separates an interior space of the device into the first volume and a second volume, wherein said layer comprises a nanopore; wherein said first and second volume are in fluidic communication through said nanopore, and wherein said first volume or said second volume comprises a sensing solution comprising ethylene glycol; applying a voltage potential across said nanopore to induce translocation of the charged molecules through said nanopore from the first volume to the second volume; detecting a signal comprising an electrical current through said pore during translocation of said charged molecules through said nanopore; and determining from said signal a characteristic of said sample with respect to said target biomolecule.

In some embodiments, the sensing solution comprising ethylene glycol is present in both the first volume and the second volume. In some embodiments, the ethylene glycol sensing solution is present in said first volume or said second volume at a concentration of 0.01% v/v or greater, 0.02% v/v or greater, 0.05% v/v or greater, 0.1% v/v or greater, 0.2% v/v or greater, 0.5% v/v or greater, 1% v/v or greater, 2% v/v or greater, 5% v/v or greater, 10% v/v or greater, 15% v/v or greater, 20% v/v or greater or 25% v/v or greater. In some embodiments, the ethylene glycol sensing solution is present in said first volume or said second volume at a concentration of at least 0.01M, 0.05M, 0.1M, 0.2M, 0.5M or 1M.

CsCl and $CaCl_2$ Gradient Sensing Solutions

In some embodiments, the buffer (e.g., a sensing solution) comprising CsCl or $CaCl_2$ is present in both the first volume and the second volume. In some embodiments, the CsCl or the $CaCl_2$ is present in both the first chamber and the second chamber at equimolar concentrations. In some embodiments, the CsCl or the $CaCl_2$ sensing solution has a different concentration in the first volume than the second volume to generate a cation-salt agent concentration gradient across a membrane.

In some embodiments, the salt agent sensing solution is in a gradient, having a concentration of CsCl or the $CaCl_2$ is in the first volume of at least 10%, 20%, 30%, 40%, 50%, 60%, 70%, 80%, 90%, 95%, or 99% less than in the second volume. In some embodiments, the salt agent sensing solution is in a gradient, having a concentration of the CsCl or the $CaCl_2$ sensing solution is in the second volume has a concentration of at least 10%, 20%, 30%, 40%, 50%, 60%, 70%, 80%, 90%, 95%, or 99% less than in the first volume.

In some embodiments, the CsCl or the $CaCl_2$ sensing solution is present in the first volume or the second volume at a concentration of 0.1M or greater. In some embodiments, the CsCl or the $CaCl_2$ sensing solution is present in the first volume or the second at a concentration of 0.5M or greater. In some embodiments, the CsCl or the $CaCl_2$ sensing solution is present in the first volume or the second at a concentration of 1M or greater. In some embodiments, the CsCl or the $CaCl_2$ sensing solution is present in the first volume or the second volume at a concentration of at least 0.01M, 0.05M, 0.1M, 0.2M, 0.5M or 1M.

In some embodiments, provided herein is a method of characterizing a sample with respect to a target dsDNA, the method comprising: providing a sample suspected of comprising a target dsDNA having a length of from 74 bp to 108 bp; loading the sample into a first volume of a nanopore device, wherein the nanopore device comprises a layer that separates an interior space of the device into the first volume and a second volume, wherein the layer comprises a nanopore comprising a minimum diameter from 27 nm to 73 nm; wherein the first and second volume are in fluidic communication through the nanopore, and wherein the first volume or the second volume comprises a sensing solution comprising 1M $CaCl_2$; applying a voltage potential across the nanopore to induce translocation of the target dsDNA, if present, through the nanopore from the first volume to the second volume; detecting a signal comprising an electrical current through the pore during translocation of the target dsDNA through the nanopore; and determining from the signal a characteristic of the sample with respect to the target dsDNA.

In some embodiments, provided herein is a method of characterizing a sample with respect to a target dsDNA, the method comprising: providing a sample suspected of comprising a target dsDNA having a length of from 58 bp to 108 bp; loading the sample into a first volume of a nanopore device, wherein the nanopore device comprises a layer that separates an interior space of the device into the first volume and a second volume, wherein the layer comprises a nanopore comprising a minimum diameter from 27 nm to 102 nm; wherein the first and second volume are in fluidic communication through the nanopore, and wherein the first volume or the second volume comprises a sensing solution comprising from 1M to 3M CsCl; applying a voltage potential across the nanopore to induce translocation of the target dsDNA, if present, through the nanopore from the first volume to the second volume; detecting a signal comprising an electrical current through the pore during translocation of the target dsDNA through the nanopore; and determining from the signal a characteristic of the sample with respect to the target dsDNA.

5.4.5. Methods Using Ethylene Glycol Sensing Solutions

The disclosure provides various additional methods using Ethylene glycol sensing solutions outlined below in the following embodiments. A person skilled in the art will appreciate the term "buffer" can be used interchangeably with the word "sensing solution."

Embodiment 1. Method of characterizing a sample with respect to a target biomolecule, comprising: providing a sample suspected of comprising a target biomolecule; loading said sample into a first volume of a nanopore device, wherein said nanopore device comprises a layer that separates an interior space of the device into the first volume and a second volume, wherein said layer comprises a nanopore; wherein said first and second volume are in fluidic communication through said nanopore, and wherein said first volume or said second volume comprises a sensing solution comprising ethylene glycol; applying a voltage potential across said nanopore to induce translocation of the charged molecules through said nanopore from the first volume to the second volume; detecting a signal comprising an electrical current through said pore during translocation of said charged molecules through said nanopore; and determining from said signal a characteristic of said sample with respect to said target biomolecule.

Embodiment 2. The method of embodiment 1, wherein said ethylene glycol is a polyethylene glycol.

Embodiment 3. The method of embodiment 2, wherein said polyethylene glycol is triethylene glycol, polyethylene glycol 200, or polyethylene glycol 400.

Embodiment 4. The method of embodiment 1, wherein said ethylene glycol comprises the structure:

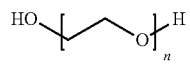

wherein n is from 1 to 10.

Embodiment 5. The method of embodiment 1, wherein said nanopore sensing solution comprises a salt.

Embodiment 6. The method of embodiment 5, wherein said salt is NaCl, KCl, or LiCl.

Embodiment 7. The method of embodiment 5, wherein said salt is present in said sensing solution at a concentration of greater than 0.01M, greater than 0.02M, greater than 0.05M, greater than 0.1M, greater than 0.2M, greater than 0.5M greater than 1M, greater than 2M, or greater than 3M.

Embodiment 8. The method of embodiment 1, wherein said target biomolecule is a polynucleotide.

Embodiment 9. The method of embodiment 8, wherein said polynucleotide is a dsDNA, ssDNA, RNA, or RNA/DNA hybrid.

Embodiment 10. The method of embodiment 8, wherein said polynucleotide has a length of no more than 2 kb, 1 kb, 500 bases, 400 bases, 300 bases, 200 bases, or 100 bases.

Embodiment 11. The method of embodiment 9, wherein said target dsDNA is less than 500 bp in length.

Embodiment 12. The method of embodiment 9, wherein said target dsDNA comprises a length of from 10 bp to 500 bp.

Embodiment 13. The method of embodiment 1, wherein said nanopore comprises a diameter from 10 nm to 150 nm.

Embodiment 14. The method of embodiment 1, wherein said nanopore is characterized by a minimum diameter of greater than 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm or 65 nm.

Embodiment 15. The method of claim 1, wherein said nanopore is characterized by a minimum diameter of less than 70 nm, 75 nm, 80 nm, 85 nm, 90 nm, 95 nm, 100 nm, 105 nm, or 110 nm.

Embodiment 16. The method embodiment 1, wherein said nanopore has a minimum diameter of less than 1000 nm, less than 500 nm, less than 200 nm, less than 100 nm, or less than 50 nm.

Embodiment 17. The method of embodiment 1, wherein the nanopore is characterized by a minimum diameter from 65 nm to 100 nm.

Embodiment 18. The method of embodiment 1, wherein the nanopore is characterized by a minimum diameter from 5 nm to 100 nm.

Embodiment 19. The method of embodiment 8, wherein said polynucleotide has a length of no more than 500 bases and said nanopore has a minimum diameter of 10 nm.

Embodiment 20. The method of embodiment 1, wherein said characterization comprises quantification of said target biomolecule.

Embodiment 21. The method of Embodiment 9, wherein said characterization comprises discrimination of lengths of dsDNA in said sample.

Embodiment 30. The method of embodiment 21, wherein said discrimination is between dsDNA length differences of less than 50 bp, less than 100 bp, less than 200 bp, less than 300 bp, less than 400 bp, or less than 500 bp.

Embodiment 31. The method of embodiment 1, wherein the accuracy of said characterization is improved as compared to characterization from the same method performed in the absence of said polyethylene glycol in said sensing solution.

Embodiment 32. The method of embodiment 1, wherein said characteristic is selected from the group consisting of: a presence or absence of, a quantity of, an identity of, a modification of, a structure of, a concentration of, or a sequence of.

Embodiment 33. The method of embodiment 24, wherein the presence or absence of said target biomolecule is determined by comparing the number of translocation signals per unit time to a threshold, above which said target biomolecule is determined to be present in said sample, and below which said target biomolecule is determined to absent in said sample.

Embodiment 34. The method of any of the above embodiments, wherein said sensing solution comprising ethylene glycol is present in both the first volume and the second volume.

Embodiment 35. The method of any of the above embodiments, wherein said ethylene glycol is present in said first volume or said second volume at a concentration of 0.01% v/v or greater, 0.02% v/v or greater, 0.05% v/v or greater, 0.1% v/v or greater, 0.2% v/v or greater, 0.5% v/v or greater, 1% v/v or greater, 2% v/v or greater, 5% v/v or greater, 10% v/v or greater, 15% v/v or greater, 20% v/v or greater or 25% v/v or greater.

Embodiment 36. The method of embodiment 1, wherein said ethylene glycol is present in said first volume or said second volume at a concentration of at least 0.01M, 0.05M, 0.1M, 0.2M, 0.5M or 1M.

Embodiment 37. The method of any of the above embodiments, wherein said method generates a detection rate of said target biomolecule in said nanopore of at least 1/min, at least 2/min, at least 3/min, at least 4/min, at least 5/min, at least 10/min, at least 15/min, at least 20/min, at least 25/min, at least 30/min, at least 40/min, at least 50/min, at least 60/min, at least 70/min, at least 80/min, at least 90/min, at least 100/min, at least 150/min, at least 200/min, at least 250/min, at least 350/min, at least 450/min, at least 550/min, at least 650/min, at least 750/min, at least 850/min, at least 950/min, at least 1150/min, at least 1250/min, at least 1350/min, at least 1450/min, at least 1550/min, at least 1650/min, or at least 1750/min Embodiment 38. The method of any one of the above embodiments, wherein said device comprises electrodes for applying a voltage across said nanopore and for monitoring an electrical current through said nanopore from one chamber to the other, wherein said electrodes are connected to a power supply.

Embodiment 39. The method of any of the above embodiments, wherein said sample comprises said polynucleotide, and wherein applying said voltage drives said polynucleotide through said nanopore from the first chamber to the second chamber upon application of said voltage potential, thereby generating an electrical signal that deviates from an open channel electrical signal.

Embodiment 40. The method of any of the above embodiments, wherein said first and second volume are in fluidic communication only through said nanopore.

5.4.6. Methods Using CsCl or $CaCl_2$ Sensing Solutions

The disclosure provides various methods using CsCl and $CaCl_2$ sensing solutions. A person skilled in the art will appreciate the term "buffer" can be used interchangeably with the word "sensing solution."

In some embodiments, provided herein is a method of characterizing a sample with respect to a target biomolecule in a sample, the method comprising: providing a sample suspected of comprising the target biomolecule; loading the sample into a first volume of a nanopore device, wherein the nanopore device comprises a layer that separates an interior space of the device into the first volume and a second volume, wherein the layer comprises a nanopore comprising a minimum diameter of greater than 4 nm; wherein the first and second volume are in fluidic communication through the nanopore, and wherein the first volume or the second volume comprises a buffer (e.g., a sensing solution) comprising CsCl or $CaCl_2$; applying a voltage potential across the nanopore to induce translocation of charged molecules in the sample through the nanopore; detecting a signal comprising an electrical current through the pore during translocation of the charged molecules through the nanopore; determining from the signal the presence or absence of a target biomolecule in the sample.

In some embodiments, the sensing solution comprises 1M CsCl, and wherein the nanopore has a minimum diameter of 102 nm or less, and wherein the polynucleotide is 58 bp or more. In some embodiments, the sensing solution comprises 1M CsCl, and wherein the nanopore has a minimum diameter of 27 nm or more, wherein the polynucleotide is 108 bp or less. In some embodiments, the sensing solution comprises 1M $CaCl_2$, and wherein the nanopore has a minimum diameter of 73 nm or less, and wherein the polynucleotide is 74 bp or more. In some embodiments, the sensing solution comprises 1M $CaCl_2$, and wherein the nanopore has a minimum diameter of 27 nm or more, wherein the polynucleotide is 108 bp or less. In some embodiments, the sensing solution comprises 1M CsCl, and wherein the nanopore has a minimum diameter of from 27 nm to 102 nm, and wherein the polynucleotide is 108 bp to 58 bp. In some embodiments, the sensing solution comprises 1M $CaCl_2$, and wherein the nanopore has a minimum diameter of from 27 nm to 73 nm, and wherein the polynucleotide has a length of from 58 bp to 74 bp. In some embodiments, the polynucleotide has a length of no more than 500 bases and the nanopore has a minimum diameter of 65 nm.

The disclosure provides various additional methods using CaCl or $CaCl_2$ sensing solutions outlined below in the following embodiments.

Embodiment 1. A method of characterizing a sample with respect to a target dsDNA, comprising: providing a sample suspected of comprising a target dsDNA having a length of from 58 bp to 108 bp; loading said sample into a first volume of a nanopore device, wherein said nanopore device comprises a layer that separates an interior space of the device into the first volume and a second volume, wherein said layer comprises a nanopore comprising a minimum diameter from 27 nm to 102 nm; wherein said first and second volume are in fluidic communication through said nanopore, and wherein said first volume or said second volume comprises a sensing solution comprising from 1M to 3M CsCl; applying a voltage potential across said nanopore to induce translocation of the target dsDNA, if present, through said nanopore from the first volume to the second volume; detecting a signal comprising an electrical current through said pore during translocation of said target dsDNA through said nanopore; and determining from said signal a characteristic of said sample with respect to said target dsDNA.

Embodiment 2. A method of characterizing a sample with respect to a target dsDNA, comprising: providing a sample suspected of comprising a target dsDNA having a length of from 74 bp to 108 bp; loading said sample into a first volume of a nanopore device, wherein said nanopore device comprises a layer that separates an interior space of the device into the first volume and a second volume, wherein said layer comprises a nanopore comprising a minimum diameter from 27 nm to 73 nm; wherein said first and second volume are in fluidic communication through said nanopore, and wherein said first volume or said second volume comprises a sensing solution comprising 1M $CaCl_2$; applying a voltage potential across said nanopore to induce translocation of the target dsDNA, if present, through said nanopore from the first volume to the second volume; detecting a signal comprising an electrical current through said pore during translocation of said target dsDNA through said nanopore; and determining from said signal a characteristic of said sample with respect to said target dsDNA.

Embodiment 3. The method of embodiment 1 or embodiment 2, wherein said characteristic is selected from the group consisting of: a presence or absence of, a quantity of, an identity of, a concentration of, a modification of, a structure of, or a sequence of.

Embodiment 4. The method of embodiment 3, wherein the presence or absence of said target dsDNA is determined by comparing the number of translocation signals per unit time to a threshold, above which said target dsDNA is determined to be present in said sample, and below which said target dsDNA is determined to absent in said sample.

Embodiment 5. A method of characterizing a sample with respect to a target biomolecule in a sample, comprising: providing a sample suspected of comprising said target biomolecule; loading said sample into a first volume of a nanopore device, wherein said nanopore device comprises a layer that separates an interior space of the device into said first volume and a second volume, wherein said layer comprises a nanopore comprising a minimum diameter of greater than 4 nm; wherein said first and second volume are in fluidic communication through said nanopore, and wherein said first volume or said second volume comprises a sensing solution comprising CsCl or $CaCl_2$; applying a voltage potential across said nanopore to induce translocation of charged molecules in said sample through said nanopore; detecting a signal comprising an electrical current through said pore during translocation of said charged molecules through said nanopore; and determining from said signal the presence or absence of a target biomolecule in said sample.

Embodiment 6. The method of embodiment 5, wherein said target biomolecule is a polynucleotide.

Embodiment 7. The method of embodiment 6, wherein said polynucleotide is a dsDNA, ssDNA, RNA, or RNA/DNA hybrid.

Embodiment 8. The method of embodiment 6 or embodiment 7, wherein said polynucleotide has a length of no more than 2 kb, 1 kb, 500 bases, 400 bases, 300 bases, 200 bases, or 100 bases.

Embodiment 9. The method of any of the above embodiments, wherein said nanopore is characterized by a minimum diameter of greater than 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm or 65 nm.

Embodiment 10. The method of any of the above embodiments, wherein said nanopore is characterized by a minimum diameter of less than 70 nm, 75 nm, 80 nm, 85 nm, 90 nm, 95 nm, 100 nm, 105 nm, or 110 nm.

Embodiment 11. The method of any of the above embodiments, wherein said nanopore has a minimum diameter of less than 1000 nm, less than 500 nm, less than 200 nm, less than 100 nm, or less than 50 nm.

Embodiment 12. The method of any of the above embodiments, wherein the nanopore is characterized by a minimum diameter from 65 nm to 100 nm.

Embodiment 13. The method of any of the above embodiments, wherein the nanopore is characterized by a minimum diameter from 5 nm to 100 nm.

Embodiment 14. The method of any of the above embodiments, wherein said polynucleotide has a length of no more than 500 bases and said nanopore has a minimum diameter of 65 nm.

Embodiment 15. The method of any of the above embodiment, wherein said sensing solution comprising CsCl or CaCl2 is present in both the first volume and the second volume.

Embodiment 16. The method of embodiment 15, wherein said CsCl or said CaCl2 is present in both said first chamber and said second chamber at equimolar concentrations.

Embodiment 17. The method of embodiment 15, wherein said CsCl or said CaCl2 has a different concentration in the first volume than the second volume so as to generate a salt gradient across said nanopore.

Embodiment 18. The method of embodiment 17, wherein said salt gradient is a concentration of said CsCl or said $CaCl_2$ is in said first volume is at least 10%, 20%, 30%, 40%, 50%, 60%, 70%, 80%, 90%, 95%, or 99% less than in the second volume.

Embodiment 19. The method of embodiment 17, wherein said salt gradient is a concentration of said CsCl or said $CaCl_2$ is in said second volume is at least 10%, 20%, 30%, 40%, 50%, 60%, 70%, 80%, 90%, 95%, or 99% less than in the first volume.

Embodiment 20. The method of any of the above embodiments, wherein said CsCl or said CaCl2 is present in said first volume or said second volume at a concentration of 0.1M or greater.

Embodiment 21. The method of any of the above embodiments, wherein said CsCl or said $CaCl_2$ is present in said first volume or said second at a concentration of 0.5M or greater.

Embodiment 22. The method of any of the above embodiments, wherein said CsCl or said $CaCl_2$ is present in said first volume or said second at a concentration of 1M or greater.

Embodiment 23. The method of any of the above embodiments, wherein said CsCl or said $CaCl_2$ is present in said first volume or said second volume at a concentration of at least 0.01M, 0.05M, 0.1M, 0.2M, 0.5M or 1M.

Embodiment 24. The method of any of the above embodiments, wherein said sensing solution comprises 1M CsCl, and wherein said nanopore has a minimum diameter of 102 nm or less, and wherein said polynucleotide is 58 bp or more.

Embodiment 25. The method of any of the above embodiments, wherein said sensing solution comprises 1M CsCl, and wherein said nanopore has a minimum diameter of 27 nm or more, wherein said polynucleotide is 108 bp or less.

Embodiment 26. The method of any of the above embodiments, wherein said sensing solution comprises 1M $CaCl_2$, and wherein said nanopore has a minimum diameter of 73 nm or less, and wherein said polynucleotide is 74 bp or more.

Embodiment 27. The method of any of the above embodiments, wherein said sensing solution comprises 1M $CaCl_2$, and wherein said nanopore has a minimum diameter of 27 nm or more, wherein said polynucleotide is 108 bp or less.

Embodiment 28. The method of any of the above embodiments, wherein said sensing solution comprises 1M CsCl, and wherein said nanopore has a minimum diameter of from 27 nm to 102 nm, and wherein said polynucleotide is 108 bp to 58 bp.

Embodiment 29. The method of any of the above embodiments, wherein said sensing solution comprises 1M $CaCl_2$, and wherein said nanopore has a minimum diameter of from 27 nm to 73 nm, and wherein said polynucleotide has a length of from 58 bp to 74 bp.

Embodiment 30. The method of any of the above embodiments, wherein said method generates a detection rate of said target biomolecule in said nanopore of at least 1/min, at least 2/min, at least 3/min, at least 4/min, at least 5/min, at least 10/min, at least 15/min, at least 20/min, at least 25/min, at least 30/min, at least 40/min, at least 50/min, at least 60/min, at least 70/min, at least 80/min, at least 90/min, or at least 100/min.

Embodiment 31. The method of any one of the above embodiments, wherein said device comprises electrodes for applying a voltage across said nanopore and for monitoring an electrical current through said nanopore from one chamber to the other, wherein said electrodes are connected to a power supply.

Embodiment 32. The method of any of the above embodiments, wherein said sample comprises said polynucleotide, and wherein applying said voltage drives said polynucleotide through said nanopore from the first chamber to the second chamber upon application of said voltage potential, thereby generating an electrical signal that deviates from an open channel electrical signal.

Embodiment 33. The method of any of the above embodiments, wherein said first and second volume are in fluidic communication only through said nanopore.

5.4.7. Devices

Any nanopore device can be used with the compositions, methods, systems, or kits provide by the disclosure. Examples of devices that can be used with the disclosure included but are not limited to a solid-state nanopore device, a biological nanopore device or a hybrid nanopore device.

The methods of the disclosure can use any of the devices or membranes known in the art. In some embodiments, methods of the disclosure can use a membrane described in Section 5.5.

Upon reading the disclosure a skilled artisan will choose an appropriate nanopore device and membrane. In some applications, the device can have a pore diameter size greater than about 20 nm, about 25 nm, or about 30 nm. In other applications, the device can have a pore diameter size greater than about 60 nm, about 70 nm, about 80 nm, about 90 nm, about 100 nm, about 110 nm, or about 120 nm.

5.4.8. Probes and Voltage-Sensitive Moieties

Depending on the application, the methods can include the use of a molecular probe. The use of probes to enhance detection using a nanopore device is described in U.S. application Ser. No. 15/513,472, which is herein incorporated by reference.

Depending of molecule and probe type it may be desirable to attach or link the probe prior to analysis. The attachment of the probe to the molecule prior to analysis can be externally (outside of the device) or in the nanopore device, but before analysis.

It will be understood by those skilled in the art that various methods well known in the art can be used to attach the probe to the molecule, including but not limited to, hybridization, conjugation, linkage chemistry, and by various chemical bonds (e.g., covalent, hydrogen and the like).

Probes

Probes are capable of specifically binding to a site on a molecule to be detected or characterized. Often binding site of the probe can be a sequence, a modification, or a structure to be detected or characterized.

Examples of probe molecules that can be used with the disclosure, include but are not limited to, a single-strand DNA, a PNA (protein nucleic acid), bis-PNA, gamma-PNA, a PNA-conjugate that increases size or charge of PNA. Other examples of probe molecules are from the group consisting of a natural or recombinant protein, protein fusion, DNA binding domain of a protein, peptide, a nucleic acid, oligo nucleotide, TALEN, CRISPR, a PNA (protein nucleic acid), bis-PNA, gamma-PNA, a PNA-conjugate that increases size, charge, fluorescence, or functionality (e.g. oligo labeled), or any other PNA derivatized polymer, and a chemical compound.

In some aspects, the probe comprises a γ-PNA. γ-PNA has a simple modification in a peptide-like backbone, specifically at the γ-position of the N-(2-aminoethyl)glycine backbone, thus generating a chiral center (Rapireddy S., et al., 2007. J. Am. Chem. Soc., 129:15596-600; He G, et al., 2009, J. Am. Chem. Soc., 131:12088-90; Chema V, et al., 2008, Chembiochem 9:2388-91; Dragulescu-Andrasi, A., et al., 2006, J. Am. Chem. Soc., 128:10258-10267). Unlike bis-PNA, γ-PNA can bind to dsDNA without sequence limitation, leaving one of the two DNA strands accessible for further hybridization.

In some aspects, the function of the probe is to hybridize to a polynucleotide with a target sequence by complement base pairing to form a stable complex. The PNA molecule may additionally be bound to additional molecules to form a complex has sufficiently large cross-section surface area to produce a detectable change or contrast in signal amplitude over that of the background, which is the mean or average signal amplitude corresponding to sections of non-probe-bound polynucleotide.

The stability of the binding of the polynucleotide target sequence to the PNA molecule is important in order for it to be detected by a nanopore device. The binding stability must be maintained throughout the period that the target-bearing polynucleotide is being translocated through the nanopore. If the stability is weak, or unstable, the probe can separate from the target polynucleotide and will not be detected as the target-bearing polynucleotide threads through the nanopores.

In a particular embodiment, an example of a probe is a PNA-conjugate in which the PNA portion specifically recognizes a nucleotide sequence and the conjugate portion increases the size/shape/charge differences between different PNA-conjugates.

Moieties

Different reactive moieties may be incorporated into the ligands to provide chemical handle to which labels maybe conjugated. Examples of reactive moieties include, but are not limited to, primary amines, carboxylic acids, ketones, amides, aldehydes, boronic acids, hydrazones, thiols, maleimides, alcohols, and hydroxyl groups, and biotin.

In some embodiments, a PNA ligand can be modified as to increase ligand charge, and therefore facilitate detection by a nanopore. Specifically, this ligand, which binds to the target DNA sequence by complementary base pairing and Hoogsteen base pairing between the bases on the PNA molecule and the bases in the target DNA, has cysteine residues incorporated into the backbone, which provide a free thiol chemical handle for labeling. Here, the cysteine is labeled to a peptide 2-aminoethylmethanethiosulfonate (MTSEA) through a maleimide linker, which provides a means to detect whether the ligand is bound to its target sequence since the label/peptide gives an increase to the ligand charge. This greater charge results in a greater change in current flow through the pore compared to an unlabeled PNA.

In some aspects, to increase the contrast in the change between the ligand bound polynucleotide and other background molecules present in the sample, modification can be made to the pseudo-peptide backbone to change the overall size of the ligand (e.g., PNA) to increase the contrast.

PEG Probes

In addition, small particle, molecules, protein, peptides, or polymers (e.g. PEG) can be conjugated to the pseudo-peptide backbone to enhance the bulk or cross-sectional surface area of the ligand and target-bearing polynucleotide complex. Enhanced bulk serves to improve the signal amplitude contrast so that any differential signal resulting from the increased bulk can be easily detected. Examples of small particle, molecules, protein, or peptides can be conjugated to the pseudo-peptide backbone include but are not limited to alpha-helical forming peptides, nanometer-sized gold particles or rods (e.g. 3 nm), quantum dots, polyethylene glycol (PEG). Method of conjugation of molecules are well known in the art, e.g. in U.S. Pat. Nos. 5,180,816, 6,423,685, 6,706,252, 6,884,780, and 7,022,673, which are hereby incorporated by reference in their entirety.

The embodiments above describe PEG labeling is through cysteine residues, however other residues can also be used. For example, Lysine residue are easily interchanged with cysteine residues to enable linkage chemistry using NHS-esters and free amines. Also, PEG can easily be interchanged with other bulk-adding constituents, like Dendrons, beads, or rods. between the bifunctional linker and the PNA, or to directly couple the Dendron. Someone skilled in the art would recognize the flexibility of this system in that the amino acid can be changed and linkage chemistry modified for that particular amino acid, e.g. Serine reactive isocyanates. Some examples of linkage chemistry that can be used for this reaction is listed in the table below.

TABLE 1

Linkage Chemistry

| Reactive Group | Target Functional Group |
|---|---|
| aryl azide | nonselective or primary amine |
| carbodiimide | amine/carboxyl |
| hydrazide | carbohydrate |
| hydroxymethyl phosphine | amine |
| imidoester | amine |
| isocyanate | hydroxyl |
| carbonyl | hydrazine |
| maleimide | sulfhydryl |
| NHS-ester | amine |
| PFP-ester | amine |
| psoralen | thymine |
| pyridyl disulfide | sulfhydryl |
| vinyl sulfone | sulfhydryl amine, hydroxyl |

In some embodiments, PNA probes that have been modified as to increase probe size, contain an epitope, contain ssDNA oligomers, contain fluorophores, additional charge, or additional size to facilitate detection or to detect that two probes are in close proximity.

Different reactive moieties can be incorporated into the probes to provide a chemical handle to which labels maybe conjugated. Examples of reactive moieties include, but are not limited to, primary amines, carboxylic acids, ketones, amides, aldehydes, boronic acids, hydrazones, thiols, maleimides, alcohols, and hydroxyl groups, and biotin.

A common method for incorporating the chemical handles are to include a specific amino acid into the backbone of the probe. Examples include, but are not limited to, cysteines (provide thiolates), lysines (provides free amines), threonine (provides hydroxyl), glutamate and aspartate (provides carboxylic acids).

Labels

As would be understood by the skilled artisan upon reading the disclosure, different types of labels can be added to a probe or moiety to further aid or enhance detection of a target biomolecule.

In some embodiments, that label is added to the probe. A label can be a molecular barcode, a reactive moiety, a unique identifier, a bead, or the like.

In some embodiments, the label is added to the probe is a reactive moiety. Reactive moieties includes labels that either: increase the size of the probe, e.g. biotin/streptavidin, peptide, nucleic acid, change the charge of the probe, e.g. a charged peptide (6xHIS), or protein (e.g., charybdotoxin), or small molecule or peptide (e.g. MTSET), change or add fluorescence to the probe (e.g., common fluorophores, FITC, Rhodamine, Cy3, Cy5, or the like), or provide an epitope or interaction site for binding a third molecule (e.g., peptides for binding antibody).

5.4.9. Increased Accuracy

Often the methods of the disclosure provide increased accuracy of detecting or characterizing a biomolecule in a sample. Depending on the application, increased accuracy can be accomplished by different ways as described in detail below.

In some embodiments, increased accuracy of detecting or characterizing can comprise detection of molecule that would otherwise not be detected in a standard (e.g., conventional) nanopore buffer.

In some applications, increased accuracy of detecting or characterizing a biomolecule can comprise detection of a substantial number of events of the molecule passing through a pore in a standard buffer. A substantial number of events, can be about 100, 200, 300, 400, 500, 600, 700, 800, 900, 1000, 1100, 1200, 1300, 1400, 1500, 1600, 1700, 1800, 1900, or 2000 events after a reasonable amount of time.

A reasonable amount of time will depend on the level of background molecules in a sample as well as the voltage applied. For example, if the nucleic acid, protein, or analyte is known to be rare in a sample, such as a biomarker from a stem cell in a blood sample, then a reasonable amount of will be longer in comparison to sample that was substantially purified for a stem cell. In some embodiments, a reasonable amount of time will be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mins. In some embodiments, a reasonable amount of time will be about 1, 2, 3, 4, 5, 6, 7, 8, 9, or 10 mins.

In some applications, increased accuracy can be determining one or more characteristic of a biomolecule (e.g., length, size, structure, a chemical modification, concentration etc) that would otherwise not be detected in a standard nanopore buffer.

In some applications, increased accuracy can be resolving the difference in length of two or more biomolecules in a sample that have a similar length (e.g., in base pairs (bp) or amino acids (AA)). In some embodiments, increased accuracy can be discrimination of different length or sizes of the biomolecule in the sample. In some embodiments, the discrimination is between length differences of less than 50 bp, 100 bp, 150 bp, 200 bp, 250 bp, 300 bp, 350 bp, 400 bp, 450 bp, or 500 bp. In some embodiments, the discrimination is between length differences of less than 10, 20, 30, 40, 50, 60, 70, 80, 90, 100, 150, or 200 amino acids.

In some embodiments, increased accuracy can be discrimination of different sizes of the biomolecule in the sample. In some embodiments, the discrimination is between different sizes can be less than 10, 20, 30, 40, 50, 60, 70, 80, 90, or 100 kDa. In some embodiments, the discrimination is between different sizes can be more than 10, 20, 30, 40, 50, 60, 70, 80, 90, or 100 kDa.

In some applications, increased accuracy can be resolving the difference in structure, conformation, or motif(s) of two or more biomolecules in a sample that have a similar structure, conformation or motif(s).

In some applications, increased accuracy can be resolving the difference in chemical modification of two or more biomolecules in a sample that have a similar modification (e.g., in charge and/or size).

In some applications, increased accuracy can be resolving the presence or absence of a modification on a protein or a nucleic acid. Examples of modifications on a biomolecule include but are not limited to: methylation, phosphorylation, acetylation, and all other modifications known in the art to be on a protein or nucleic acid.

A standard buffer used for comparison can be any nanopore running buffer or sensing buffer known in the art. Examples of standard nanopore buffers, include but are not limited to, a buffer comprising divalent LiCl, KCl, or NaCl or a monovalent buffer thereof.

In some embodiments, the buffer comprises an effective amount of LiCl, KCl, or NaCl or a monovalent buffer thereof. An "effective amount" of a standard buffer is one that allows the biomolecule to translocate through a pore at a reasonable rate, but does not result in increased detection, resolution, or characterization of a biomolecule to two or more biomolecules with similar physical properties.

In some embodiments, the standard buffer comprises LiCl, KCl, NaCl or a monovalent ion thereof has a molar concentration of less than 0.5M, 1M, 2M, 3M, 4M, or 5M. In some embodiments, a standard buffer is 1M KCL, 1M LiCl, or 4.0M LiCl, 10 mM Tris HCl pH 8.8, 1 mM EDTA.

In some embodiments, the standard buffer does not comprise a polyether agent (e.g., as described herein). In some embodiments, the buffer does not comprise an effective amount of a polyether of Formula (II)-(IV) or an embodiment thereof.

In some embodiments, the standard buffer can further comprise one or more buffering chemicals or agents. Buffering chemicals or agents used in a standard buffer can include, but are not limited to, Tris, Tris-HCL, Borate, CHES, Bis-tris propane, CAPS potassium phosphate buffer, HEPES, or others known in the art.

In some embodiments, the standard buffer can further comprise a chelating agent. Non-limiting examples of chelating agents that can be used in a standard buffer include but are not limited to EDTA, EGTA, or the like.

A standard buffer can further comprise any other agent known to be included in a standard nanopore buffer.

5.5. Nanopore Devices

The present disclosure as provides nanopore device, comprising an effective amount of a sensing solution as provide in Section 5.3, and a nonporous membrane.

Any nonporous membrane known in the art can be used with the devices of the disclosure. Non-limiting examples of a nonporous membrane include a solid-state membrane, a biological membrane, or a hybrid membrane. Other examples of membrane substrates that can be used with the devices of the disclosure are described in Section 5.5. The membrane used with the devices of the disclosure can comprise a pore size of any size, so long it is configured it allow for the translocation of a target molecule (e,g, the molecule to be detection or characterized, modified or unmodified) through the membrane.

5.5.1. Devices

A nanopore device can include at least a pore that forms an opening in a structure separating an interior space of the device into two volumes, and at least a sensor configured to identify objects (for example, by detecting changes in parameters indicative of objects) passing through the pore. A device used with the disclosure can have a pore of any architecture (e.g., round shape, funnel shape, ect.). A device used with the disclosure can have a single pore, a dual pore, or it can have several pores, such as, for example, an array of pores.

Nanopore devices used for the methods described herein are also disclosed in PCT Publication WO/2013/012881, incorporated by reference in entirety.

A nanopore device typically contains a membrane separating two volumes or chambers, where the membrane has a nanopore through the membrane that allows fluid communication between the two volumes. The nonporous membrane can be made from a biological substrate (e.g., lipid membrane) or a non-biological substrate (e.g., solid substrate) or any other substrate known in the art. In some embodiments, the nanopore device can be a solid-state nanopore device, biological nanopore device or a hybrid nanopore device.

When the two volumes contain an electrolyte, such as a salt, a current can flow through the pore by applying a voltage potential across the pore, e.g., via electrodes on either side of the pore. Using a low-noise transimpedance amplifier, nanopore devices monitor ionic current through a single pore that separates two chambers or volumes.

Voltage is applied across the membrane, creating a current (e.g., ionic current) through the nanopore that is filtered, sampled, and recorded for analysis. When the voltage captures a single molecule such as DNA, RNA or protein, it passes through the pore and temporarily shifts the current, creating a single molecule "event." Using a variety of techniques as described for example in US Patent Application Publication No. 2016/0266089, "Target Detection with Nanopore," incorporated herein by reference one can detect and quantitate the presence of a specific target molecule from among a population of background molecules by analyzing the distribution of recorded events.

Also provided herein, is a nanopore device comprising a layer that separates an interior space of the device into the first volume and a second volume, wherein said layer comprises a nanopore; wherein said first and second volume are in fluidic communication through said nanopore, and wherein said first volume or said second volume comprises a buffer comprising ethylene glycol. In some embodiments, the system further comprises a first electrode in said first volume and a second electrode in said second volume, wherein said first and second electrode are configured to apply a voltage potential across said nanopore. In some embodiments, the system further comprises a target biomolecule in said first volume or said second volume, wherein said voltage potential induces translocation of said target biomolecule through said nanopore.

5.5.2. Sensing Solutions

It is contemplated that any of the devices of disclosure can be used with any of the compositions provided in Section 5.3.

In some embodiments, the nanopore device of the disclosure, comprises an effective amount of a sensing solution as described in Section 5.3 and a nanoporous membrane. The sensing solutions with the device can be applied asymmetrically, where the cis volume and trans volume has different sensing solutions.

Depending on the biomolecule's characteristic detected one skilled in the art will be aware upon reading the disclosure which device and sensing solution would work the best for the application. An effective amount is one that enhances detection of one or more of the biomolecule's characteristics to be detected as compared to a standard buffer.

In some embodiments, the effective amount of a polyether agent (e.g., as described herein) in a sensing solution is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% v/v.

In some embodiments, the effective amount of a polyether agent (e.g., as described herein) in a sensing solution is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight.

In some embodiments, the effective amount of a polyether agent in a sensing solution is 30% or less by weight of a polyether agent (e.g., as described herein).

In some embodiments, a method can comprise a sensing solution comprising an effective amount of a polyether of Formula (I)-(IV). In some embodiments, the device comprises an asymmetric sensing solution described in Section 5.4.4.

5.5.3. Solid-State Membranes

The present disclosure can be used with a solid-state membrane. A solid-state membrane is one that is engineered by drilling or etching the opening in a solid substrate, using various solid materials known in the art such as, for example, polymer membranes, alumina, block copolymer membranes and the like.

Depending on the target or biomolecule to be detected using the methods provided herein, the skilled artisan will choose the appropriate solid substrate. Examples of solid substrates that can be used in solid-state nanopore device with the disclosure include but are not limited to silicon-based membranes, including silicon mononitride (SiN), disilicon nitride (Si2 N), silicon sesquinitride (Si3 N4), and silicon dioxide (SiO2).

In some embodiments, the solid substrate can be aluminum oxide ($Al_2O_3$). In some embodiments, aluminum oxide ($Al_2O_3$) is used to coat the surface of a nanopore thereby providing a nanopore wall contains positive surface charge that can aid the detection of negatively charged molecules.

In some embodiments the solid substrate, can be graphene. In some embodiments the graphene monlayers can be further modified by coating with $TiO_2$. In some embodiments, a nanopore is formed by alternating layers comprising of graphene and $AlO_2$.

In some embodiments, the solid substrate can be boron nitride (BN). In some embodiments, the solid substrate can be hafnium oxide ($HfO_2$). In some embodiments, the solid substrate can be and molybdenum disulfide ($MoS_2$).

In some embodiments, the surface properties of the nanopore walls can be altered or modified to enhance detection. In some embodiments, the nanopore walls are modified by covalent binding of organosilane molecules, atomic layer deposition (ALD) of alumina, or electrostatic adsorption of molecules that have a charge opposite to the nanopore wall surface that can enhance detection or decrease noise or a combination thereof.

5.5.4. Biological Membranes

The method or device of the disclosure can comprise a biological membrane. A biological nanopore is a biological substrate that provides a nano-scale opening that is formed by a proteinaceous pore in a lipid membrane. The biological substrate can be unmodified or engineered by standard techniques known in the art to further enhance the detection.

Because biological nanopores provide fixed and atomic-precision geometries they may be more advantageous for particular applications over the, solid-state nanopores can have a range of diameters depending on the fabrication technique used to form the nanopores.

Any biological and synthetic protein capable of forming a nanopore (e.g., a funnel shape, channel shaped, or bottleneck shape) can be used with the methods, systems, or kits of the disclosure. In some applications, synthetic DNA origami pores within a lipid bilayer can be used with the disclosure. The flexibility of DNA origami, provided by DNA-engineering techniques, allows a skilled artisan to design pore with new architectures and properties tailored for a specific application.

As the skilled artisan would appreciate, biological nanopores can be further engineered using approaches like site-directed mutagenesis or incorporation of specific adaptors to adapt the pores for particular sensing applications. Site-specific mutagenesis allows the production of mutants, through the use of specific oligonucleotide sequences which encode a DNA sequence comprising the desired mutation(s), as well as a sufficient number of adjacent nucleotides, to provide a primer sequence of sufficient size and in order to conduct further modification.

In some applications, mutations by site-specific mutagenesis may be used to improve, alter, decrease, modify, or otherwise change the properties of the polynucleotide itself, and/or alter the properties, activity, composition, stability, or primary sequence of the encoded polypeptide.

In some applications, mutagenesis of a polynucleotide may alter one or more physical properties of the polypeptide. For example, site mutagenesis can be used to remove negatively charged amino acids or add positively charged residues to the pore to better facilitate analyte translocations. In other applications, site mutagenesis can be used replace amino acids with unnatural amino acids.

Depending on the target molecule to be detected, a skilled artisan will choose the appropriate membrane for the application desired.

In some embodiments, a biological membrane comprises a *Mycobacterium smegmatis* porin A (MspA) nanopore. In some embodiments, a biological membrane comprises a *Mycobacterium smegmatis* porin A (MspA) nanopore. In some embodiments, the *Mycobacterium smegmatis* porin A (MspA) comprise one or more mutations. In some embodiments, the *Mycobacterium smegmatis* porin A (MspA) comprise one or more mutations and a further modification increase detection, such as probe or the like.

In some embodiments, a biological membrane comprises Staphylococcal α-hemolysin nanopore. In some embodiments, α-hemolysin comprise one or more mutations. In some embodiments, the α-hemolysin nanopore comprise one or more mutations and a further modification for to increase detection, such as probe or the like.

In some embodiments, a biological membrane comprises a Aerolysin (AeL) is a heptameric nanopore with a narrow bottleneck-shaped structure at the extracellular entrance and a small extracellular mouth approximately 1 nm in diameter.

In some embodiments, a biological membrane comprises a bacteriophage phi29 motor based nanopore. Because of the larger size of the phi29 motor nanopores are particularly useful for protein detection applications. In some embodiments, the phi29 motor nanopore comprises one or more mutations. In some embodiments, the phi29 motor nanopore comprises one or more mutations and a further modification for to increase detection, such as probe or the like.

In some embodiments, a biological membrane comprises a cytolysin A (ClyA) from *Salmonella typhi* nanopore. In some embodiments, the ClyA nanopore comprises one or more mutations. In some embodiments, the ClyA nanopore comprises one or more mutations and a further modification for to increase detection, such as probe or the like.

In some embodiments, a biological membrane comprises an outer membrane protein G (OmpG) nanopore. In some embodiments, the OmpG nanopore comprises one or more mutations. In some embodiments, the OmpG nanopore comprises one or more mutations and a further modification for to increase detection.

5.5.5. Hybrid Membranes

The method or device of the disclosure can comprise a hybrid membrane. The disclosure also provides compositions, methods, systems, kits with a hybrid nanopore device comprising a pore made from a biological substrate and a solid-state substrate, thereby forming a hybrid pore.

In some embodiments, the hybrid nanopore device can be nanopores of a solid substrate as provided herein and known in the art, that are coated with a lipid bilayer. In some embodiments, hybrid nanopore can comprise biomimetic nuclear pore complexes. In some embodiments, the hybrid nanopore device can comprise glass pipettes with ion channels trapped at the tip opening.

In some embodiments, the hybrid nanopore comprises a carbon nanotubes (CNTs) embedded within a lipid bilayer or live cell membrane. In some embodiments, the hybrid nanopore comprises a α-HL pore within a SiNx pore. In some embodiments, the hybrid nanopore comprises a 3D DNA origami structures within a SiNx pores.

5.5.6. Fabrication of a Pore

It is contemplated that solid-state pores, biological pores, or hybrid pores can be used the compositions, methods, systems, and kits of the disclosure. Depending on the biomolecule to be detected upon reading the disclosure the skilled artisan will choose the appropriate pore to be used.
Solid-State Pores The term "solid state" is here meant to refer to non-biological materials generally. Pores may be fabricated through a membrane in several ways known to one of skill in the art. For example, the pore may be a protein channel inserted in a lipid bilayer membrane or it may be engineered by drilling, etching, or otherwise forming the pore through a solid-state substrate such as silicon dioxide, silicon nitride, grapheme, or layers formed of combinations of these or other materials, in order to form a pore-bearing membrane. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. In some aspects, for example, a single sheet of graphene membrane of about 0.3 nm thick can be used as the pore-bearing membrane.

Solid-state nanopores can be made in a variety of sizes, with size being characterized by the effective diameter and length of the pore. The length of the pore is implicitly defined by the membrane thickness, which is fabricated as a freestanding membrane in a silicon-based substrate prior to nanopore formation. The thickness can be made 1-100 nm, or larger than 100 nm, by a variety of fabrication steps, including deposition and etching. The pore formation process governs the pore geometry, shape, and effective diameter.

Specialized instrumentation using focused beams ($Ga^+$, $He^+$, electron, etc.) can form pores in membranes in arbitrary thicknesses, with diameters 20 nm and greater. Smaller than 20 nm pores can also be accomplished with $He^+$ beam or TEM, or by using advanced techniques such as atomic layer deposition to shrink the size after initial formation of a larger diameter pore. All of these methods are expensive to operate and work serially (i.e., forming one pore at a time), thus being limited in the volumes of nanopore devices that can be generated per unit time. Such specialized tools are also not widely available in commercial foundries. Controlled dielectric breakdown (CDB) does not require specialized instrumentation (Kwok, H, K Briggs, and V Tabard-Cossa. "Nanopore Fabrication by Controlled Dielectric Breakdown." PloS One 9, no. 3 (2014): e92880, and patent EP2847367), but it can only form pores if the membrane thickness is below a threshold (15 nm nominally), placing greater demands (tighter tolerances) on the membrane formation process.

More specifically, the pore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of Chamber B between the membranes. A holder is seated in an aqueous bath that is comprised of the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

5.5.7. Pore Size

As a skilled artisan will appreciate, the size of the pore in a membrane must be large enough to accommodate the translocation of the target molecule (modified with a detection means, such as a probe or other voltage-sensitive moiety or unmodified) through the membrane. As such, the pore(s) in the nanopore device can be of a nano-scale or micro-scale.

In one aspect, each membrane pore has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the membrane pore is no more than about 200 nm in diameter. Alternatively, the pore is no more than about 195 nm, 190 nm, 185 nm, 180 nm, 175 nm, 170 nm, 165 nm, 160 nm, 155 nm, 150 nm, 145 nm, 140 nm, 135 nm, 130 nm, 125 nm, 120 nm, 115 nm, 110 nm, 105 nm, 100 nm, 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm or 10 nm in diameter.

In one aspect, the membrane pore has a diameter that is between about 10 nm and about 200 nm, or alternatively between about 10 nm and about 180 nm, or between about 10 nm and about 170 nm, or between about 10 nm and about 160 nm, or between about 10 nm and about 150 nm, or between about 10 nm and about 140 nm, or between about 15 nm and about 50 nm.

In some aspects, the length or depth of the pore is sufficiently large so as to form a channel connecting two otherwise separate volumes. In some such aspects, the depth of each pore is greater than 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, or 900 nm. In some aspects, the depth of each pore is no more than 2000 nm or 1000 nm. In some embodiments, the depth of the pore is about 30 nm. In some embodiments, the depth of the pore is in the range of 10-100 nm.

In some applications, the device can have a membrane with pore diameter size greater than about 20 nm, about 25 nm, or about 30 nm. In other applications, the device can have a pore diameter size greater than about 60 nm, about 70 nm, about 80 nm, about 90 nm, about 100 nm, about 110 nm, or about 120 nm.

In some aspects, the membrane pore has a substantially round shape. "Substantially round," as used here, refers to a shape that is at least about 80% or 90% in the form of a cylinder. In some embodiments, the pore is square, rectangular, triangular, oval, or hexangular in shape.

In one aspect, the membrane pore has a depth that is between about 1 nm and about 10,000 nm, or alternatively, between about 2 nm and about 9,000 nm, or between about 3 nm and about 8,000 nm, etc.

Much larger pores (e.g., 65 nm diameters and larger) can be made at high volume more inexpensively by using simpler process technologies with less expensive patterning equipment that are more widely available in semiconductor foundries. Critically, such tools and process technology can form the pores in high throughput wafer-scale steps. For example, one fabrication technology that can be use is a patterning technology is combining argon fluoride (ArF) optical lithography (193 nm wavelength light source) with plasma etch or deposition techniques. Such process technology can make 65 and 90 nm feature sizes, by definition, including nanopore holes in freestanding membrane structures. Therefore, solid-state nanopore chips can be made significantly less expensively, and at high volumes, if larger nanopore diameters (e.g., 65 nm, 90 nm, and larger) can be employed in nanopore sensing applications of interest.

5.5.8. Sensors

In some embodiments, the nanopore device of the disclosure can include one or more sensors to carry out the detection of the target biomolecule.

The sensors used in the device can are primarily directed to sensors configured to identify a target biomolecule by measuring a change in current or a change in voltage associated with the translocation of a target biomolecule through a nanopore. However, a sensor can include any sensor suitable for identifying a target polynucleotide. For instance, a sensor can be configured to identify the target polynucleotide by measuring a current, a voltage, a pH value, an optical feature, or residence time associated with the polymer. In other aspects, the sensor may be configured to identify one or more individual components of the target polynucleotide or one or more components bound or attached to the target polynucleotide. The sensor may be formed of any component configured to detect a change in a measurable parameter where the change is indicative of the target biomolecule, a component of the target biomolecule, or a component bound or attached to the target biomolecule.

In a preferred embodiment, the sensor includes a pair of electrodes placed at two sides of a pore to measure an ionic current across the pore when a biomolecule or other entity, in particular a target polynucleotide, moves through the pore. This is referred to herein as a type of electrical detection. In certain aspects, the ionic current across the pore changes measurably when a target polynucleotide segment passing through the pore is bound to a payload molecule. Such changes in current may vary in predictable, measurable ways corresponding with, for example, the presence, absence, and/or size of the target polynucleotide molecule present.

In a preferred embodiment, the sensor comprises electrodes that apply voltage and are used to measure current across the nanopore. Translocations of molecules through the nanopore provides electrical impedance (Z) which affects current through the nanopore according to Ohm's Law, $V=IZ$, where V is voltage applied, I is current through the nanopore, and Z is impedance. Inversely, the conductance $G=1/Z$ are monitored to signal and quantitate nanopore events. The result when a molecule translocates through a nanopore in an electrical field (e.g., under an applied voltage) is a current signature that may be correlated to the molecule passing through the nanopore upon further analysis of the current signal.

When residence time measurements from the current signature are used, the size of the component can be correlated to the specific component based on the length of time it takes to pass through the sensing device.

When the small biomolecule passes through the nanopore, it causes a reduction of current. The current through the nanopore can be measured by a sensing entity by using either alternating current (AC) or direct current (DC) measurements.

The current through the nanopore can be measured by using AC or DC measurement between two Ag/AgCl electrodes located on the appropriate side of the membrane separating two volumes that are in fluidic communication via a nanopore through the membrane. Aqueous solutions containing an electrolyte to carry the current (e.g., KCl) are used throughout. Provided herein are methods that use specific electrolytes to facilitate detection of smaller molecules (e.g., polynucleotides less than 500 bp in length) in larger nanopores (e.g., 25 nm or more).

A sensor can be configured to identify the charged polymer by measuring a current, a voltage, pH, an optical feature or residence time associated with the charged polymer or one or more individual components of the charged polymer. In some embodiments, the sensor includes a pair of electrodes placed at opposing sides of a pore to measure an ionic current through the pore when a molecule or particle, in particular a charged polymer (e.g., a polynucleotide), moves through the pore.

In certain embodiments, the sensor measures an optical feature of the polymer or a component (or unit) of the polymer. One example of such measurement includes identification by infrared (or ultraviolet) spectroscopy of an absorption band unique to a particular unit.

When residence time measurements are used, they will correlate the size of the unit to the specific unit based on the length of time it takes to pass through the sensing device.

In some embodiments, the sensor is functionalized with reagents that form distinct non-covalent bonds with each of the probes. In this respect, the gap can be larger and still allow effective measuring. For instance, a 5 nm gap can be used to detect a probe/target complex measuring roughly 5 nm. Tunnel sensing with a functionalized sensor is termed "recognition tunneling." Using a Scanning Tunneling Microscope (STM) with recognition tunneling, a probe bound to a target motif is easily identified.

Therefore, the methods of the present technology can provide charged polynucleotide (e.g., DNA) delivery rate control for one or more recognition tunneling sites, each positioned in one or both of the nanopore channels or between the pores, and voltage control can ensure that each probe/target complex resides in each site for a sufficient duration for robust identification.

Sensors in the devices and methods of the present disclosure can comprise gold, platinum, graphene, or carbon, or other suitable materials. In a particular aspect, the sensor includes parts made of graphene. Graphene can act as a conductor and an insulator, thus tunneling currents through the graphene and across the nanopore can sequence the translocating DNA.

In some embodiments, the tunnel gap has a width that is from about 1 nm to about 20 nm. In one aspect, the width of the gap is at least about 1 nm, or alternatively at least about 1.5, 2, 2.5, 3, 3.5, 4, 4.5, 5, 6, 7, 8, 9, 10, 12 or 15 nm. In another aspect, the width of the gap is not greater than about 20 nm, or alternatively not greater than about 19, 18, 17, 16, 15, 14, 13, 12, 11, 10, 9, 8, 7, 6, 5, 4, 3, or 2 nm. In some aspects, the width is between about 1 nm and about 15 nm, between about 1 nm and about 10 nm, between about 2 nm and about 10 nm, between about 2.5 nm and about 10 nm, or between about 2.5 nm and about 5 nm.

In some embodiments, the sensor is an electric sensor. In some embodiments, the sensor detects a fluorescent detection means when the probe has is label to create unique fluorescent signature. A radiation source at the outlet can be used to detect that signature.

In some embodiments, when detection occurs via a sensor that measures a change in current or a change in voltage, the depth of the event should have a signal-to-noise ratio (SNR) of at least six, and the event duration must be at least two times the low-pass filter rise time to achieve full depth. Published data and models using standard instrumentation suggest that the pore diameter must be well below 50 nm to achieve DNA detection. For example, by increasing the filter cutoff frequency, for example to 30 kHz, DNA as short as 330 bp can hit full depth, but the increase in noise to ~25 pA RMS means that the pore diameter must be 16 nm or smaller. In general, when using standard nanopore instrumentation, buffers and devices, DNA 500 bp or shorter are not detectable in nanopores 65 nm are larger in diameter. Therefore, in some embodiments, the ethylene glycol sensing solution provides the most significant enhancement of detection in nanopore devices of small molecules such as 500 bp or shorter polynucleotides in nanopores from 10 nm to 150 nm in diameter.

5.5.9. Electrodes & Translocation

In one aspect, the device has electrodes in the chambers connected to one or more power supplies. In some aspects, the power supply can be a voltage-clamp or a patch-clamp, which can supply a voltage across a pore and measure the current through the pore.

By virtue of the voltage present at the pore, charged molecules in one volume can be captured by the electric field above the pore and pulled through the pore to exit into the other volume. The size and strength of the electric field, speed of translocation, and direction of the movement can be controlled by the magnitude and polarity of the voltage.

One example concerns a target polynucleotide. In a first step, the polynucleotide is loaded into the cis chamber. By virtue of its negative charge under a physiological condition at a pH of about 7.4, the polynucleotide can be pulled into and moved through a pore on which a voltage is applied.

In some embodiments, the device comprises electrodes for applying a voltage across said nanopore and for monitoring an electrical current through said nanopore from one chamber to the other, wherein said electrodes are connected to a power supply. In some embodiments, the sample comprises said polynucleotide, and wherein applying said voltage drives said polynucleotide through said nanopore from the first chamber to the second chamber upon application of said voltage potential, thereby generating an electrical signal that deviates from an open channel electrical signal. In some embodiments, the first and second volume are in fluidic communication only through said nanopore.

In some embodiments, the device comprises electrodes for applying a voltage across said nanopore and for monitoring an electrical current through said nanopore from one chamber to the other, wherein said electrodes are connected to a power supply. In some embodiments, the first and second volume are in fluidic communication only through said nanopore. In some embodiments, the first and second electrodes are further configured to detect a differential electrical signal generated from said passage of said target biomolecule through said nanopore. In some embodiments, the differential signal is a change in current through said nanopore.

In some embodiments, the device comprises electrodes for applying a voltage across the nanopore and for monitoring an electrical current through the nanopore from one chamber to the other, wherein the electrodes are connected to a power supply. In some embodiments, the sample comprises the polynucleotide, and applying the voltage drives the polynucleotide through the nanopore from the first chamber to the second chamber upon application of the voltage potential, thereby generating an electrical signal that deviates from an open channel electrical signal. In some embodiments, the first and second volume are in fluidic communication only through the nanopore.

5.5.10. Detection Rate

Depending the application, the detection rate of the methods, devices, systems, and kits, maybe increased.

In some embodiments, the method generates a detection rate of said target biomolecule in said nanopore of at least 1/min, at least 2/min, at least 3/min, at least 4/min, at least 5/min, at least 10/min, at least 15/min, at least 20/min, at least 25/min, at least 30/min, at least 40/min, at least 50/min, at least 60/min, at least 70/min, at least 80/min, at least 90/min, at least 100/min, at least 150/min, at least 200/min, or at least 250/min.

In some applications, the capture of a method provided herein can be normalized, in order to compare capture rates of two molecules that are not the same in size or weight. Rates can be normalized using standard methods known in the art. As used herein, normalization capture rates are indicated by an asterisk "*".

In some embodiments, the method generates a normalized detection rate of at least 1/nM*min, at least 2/nM*min, at least 3/nM*min, at least 4/nM*min, at least 5/nM*min, at least 10/nM*min, at least 15/nM*min, at least 20/nM*min, at least 25/nM*min, at least 30/nM*min, at least 40/nM*min, at least 50/nM*min, at least 60/nM*min, at least 70/nM*min, at least 80/nM*min, at least 90/nM*min, or at least 100/nM*min,

5.6. Applications

The compositions, devices, methods, systems, and kits provided herein can be applied for the detection or characterization of biomolecules. Characterization of the biomolecule can include determining any property of the molecule (modified by a probe or voltage-sensitive moiety or unmodified) that causes a variance in a measurable electrical signature. Characterization can include determining the concentration of a molecule in a sample. Examples of such applications, include but are not limited to, diagnostics biomarker testing, infectious disease detection, genetic screening (e.g., genetic locus/mutation or GMO in a plant), and drug or chemical agent screening.

In some embodiments, a computer readable medium stores code that detects translocations through the nanopore device used for the detection or characterization for a particular application. In some embodiments, computer readable medium stores code that detects translocations through the nanopore device transient drops in current and uses an algorithm that identifies events with significant standard deviation as compared to a determined baseline current. Depending on the application significant standard deviation can include 1, 2, 3, 4, 5, 6, 7, 8, 9, 10, 11, 12, 13, 14, or 15 standard deviations as compared to a determined baseline.

5.6.1. Polynucleotides

The disclosure provides for the detection or characterization of polynucleotides. The compositions, methods, systems, and kits can be applied to various applications requiring the detection and analysis of biomolecules in a sample. In such an application, the presence or absence of a biomolecule can be determined by comparing the number of translocation signals per unit time to a threshold, above which said target biomolecule is determined to be present in said sample, and below which said target biomolecule is determined to absent in said sample.

The inventive aspects of the disclosure can be applied to any genetic diagnostic. Examples of genetic diagnostic elements that can used with the disclosure include but are not limited to a gene, a SNP, a miRNA, a shRNA, or a CRISPR induced modification.

The methods of the disclosure can be applied to an infectious disease detection where the polynucleotide detected or characterized is from a microbe, microorganism, pathogen, virus, prion, or bacteria is determined using the disclosure.

The inventive aspects of the disclosure can be applied to genetic screening. Genetic screening can be applied to either a biopsy sample or a research sample. Examples of various types of genetic screening elements that can be used with the disclosure include: a SNP, an insertion, a deletion, a copy number (e.g, copy number variation), translocation, GMO content, or a CRISPR induced modification screening. As a skilled artisan would appreciate the detection of small genetic modification (e.g., such as a SNP) could further use a probe molecule or the like to enhance or aid detection. For research samples, various types of genetic screening elements that can be used with the disclosure include: modifications of a sequence, location in a genome, on plasmid, or ect., or number of the polynucleotide can be characterized The inventive aspects of the disclosure can be applied to cancer screening. Examples of type of cancer screening that can be used with the disclosure include: methylation status, oncogene activation status, mutational status of an oncogene, or mutational status of a tumor suppressor gene.

5.6.2. Proteins

The disclosure provides for the detection or characterization of proteins, peptides, antibodies, or proteins bound to other molecules such as polynucleotides, probes, beads or dyes.

The compositions, devices, methods, systems, and kit provided by the disclosure can be applied to protein for diagnostics biomarker testing, infectious disease detection, genetic screening, and drug or chemical agent screening.

The inventive aspects of the disclosure can be applied to protein diagnostics. Protein biomarker screening that can be used with the disclosure include: detection and characterization of a target protein (presence or absence, copy number, expression level) or a modification of a target protein to determine its activation status in a particular signaling pathway (such a phosphorylation at a certain residue required or activation).

The inventive aspects of the disclosure can be applied to infectious disease detection wherein a protein detected or characterized is from a microbe, microorganism, pathogen, virus, prion, or bacteria.

The inventive aspects of the disclosure can be applied to genetic screening of gene product wherein a protein is detected and characterized for a consequence coding mutation from a genetic modification in the template caused by a SNP, an insertion, a deletion, a copy number (e.g, copy number variation), translocation, an inserted transgene (e.g., GMO content), a CRISPR induced modification, or a V(D)J recombination used in the generation of antibodies and T-cell receptors.

The inventive aspects of the disclosure can be applied to drug or chemical agent screening. A drug or chemical agents, include but are not limited to, a small molecule, a peptide, a binding molecule, or an antibody. For such an application, the detection of characterization of the protein can be used to monitor chemical and biochemical reactions of specific analytes by determining structural changes (conformational changes or motif changes) that occur on the protein during such reactions.

5.7. Systems

The disclosure also provides systems for detecting or characterizing a biomolecule in a sample. The disclosure also provides systems for carrying out the methods of the disclosure.

A system can comprise, a nanopore device, a sensing solution of the disclosure, a sensor for detecting a current; a processor; and a computer readable medium for storing code that when executed by the processor causes the processor to detect or characterize the biomolecule.

Depending on the user's needs, the computer system (e.g., processor and computer readable medium) of the system can be tailored to their needs. In some embodiments, the computer system is a system described in part or in whole in FIG. 29A or FIG. 29B.

Often the system of the disclosure will comprise a computer readable medium stores code that detects translocations through the nanopore device.

In some embodiments, the computer readable medium stores code that detects translocations as transient drops in current by identifying one or more events with a significant standard deviation as compared to a determined baseline current (e.g., the mean value). Depending on the application, a significant standard deviation can include about 1, 2, 3, 4, 5, 6, 7, 8, 9, 10, 11, 12, 13, 14, or 15 standard deviation as compared to a determined baseline.

The determined baseline current can be established by a mean amplitude and RMS noise for a given time period that precedes or follows a presumed event (e.g., to background molecules in a sample). The determined baseline current can also be established by a mean amplitude and RMS noise for a given time period that precedes or follows a presumed event (e.g., to background molecules in a running buffer).

In some further embodiments, the computer readable medium stores an algorithm that identifies one or more current signature that have been predetermined or already known for a particular biomolecule type, modification, structure, a molecular detection means, which can include but is not limited to, a probe, a voltage-sensitive moiety, a bead, a dye, or the like.

5.7.1. Nanopore Devices

The systems provide by the disclosure can be used with any nanopore device or membrane known in the art. Examples of devices that can be used with the disclosure, included but are not limited to, a solid-state nanopore device, a biological nanopore device or a hybrid nanopore device.

The systems of the disclosure comprise any of the devices or membranes described in Section 5.5. As a skilled artisan will appreciate, the size of the pore in a membrane must be large enough to accommodate the translocation of the target molecule (modified with a detection means, such as a probe or other voltage-sensitive moiety or unmodified) through the membrane. As such, the pore(s) in the nanopore device can be of a nano-scale or micro-scale.

In some applications, the device can have a pore diameter size greater than about 20 nm, about 25 nm, or about 30 nm. In other applications, the device can have a pore diameter size greater than about 60 nm, about 70 nm, about 80 nm, about 90 nm, about 100 nm, about 110 nm, or about 120 nm.

Upon reading the disclosure the skilled artisan will choose an appropriate nanopore device and membrane.

5.7.2. Sensing Solutions

It is contemplated that any of the sensing solution compositions provided by the disclosure in Section 5.3 can be used in an effective amount with the systems of the disclosure. As discussed herein, a person skilled in the art would readily realize that additional agents can be added to a sensing solution.

Any of the polyether agents described herein can be utilized in a sensing solution. In some embodiments, the system can comprise a sensing solution comprising an effective amount of a polyether of Formula (I)-(IV). In some embodiments, the system comprises an asymmetric or gradient sensing solution as described in Section 5.4.4

5.7.3. Systems with a CsCl or a CaCl$_2$ Sensing Solution

The disclosure provides additional embodiments for a system comprising a CsCl or CaCl$_2$ sensing solution as outlined below. A person skilled in the art will appreciate the term "buffer" can be used interchangeably with the word "sensing solution."

Embodiment 34. A system comprising a nanopore device, wherein said nanopore device comprises a layer that separates an interior space of the device into the first volume and a second volume, wherein said layer comprises a nanopore; wherein said first and second volume are in fluidic communication through said nanopore, and wherein said first volume or said second volume comprises a sensing solution comprising CsCl or CaCl$_2$.

Embodiment 35. The system of embodiment 34, further comprising a first electrode in said first volume and a second electrode in said second volume, wherein said first and second electrode are configured to apply a voltage potential across said nanopore.

Embodiment 36. The system of embodiment 35, further comprising a target biomolecule in said first volume or said second volume, wherein said voltage potential induces translocation of said target biomolecule through said nanopore.

Embodiment 37. The system of embodiment 36, wherein said first and second electrodes are further configured to detect a differential electrical signal generated from said passage of said target biomolecule through said nanopore.

Embodiment 38. The system of embodiment 37, wherein said differential signal is a change in current through said nanopore.

5.7.4. Systems with an Ethylene Glycol Sensing Solution

The disclosure provides additional embodiments for a system comprising ethylene glycol sensing solution as outlined below. A person skilled in the art will appreciate the term "buffer" can be used interchangeably with the word "sensing solution."

Embodiment 33. A system comprising a nanopore device, wherein said nanopore device comprises a layer that separates an interior space of the device into the first volume and a second volume, wherein said layer comprises a nanopore; wherein said first and second volume are in fluidic communication through said nanopore, and wherein said first volume or said second volume comprises a sensing solution comprising ethylene glycol.

Embodiment 34. The system of embodiment 33, further comprising a first electrode in said first volume and a second electrode in said second volume, wherein said first and second electrode are configured to apply a voltage potential across said nanopore.

Embodiment 35. The system of embodiment 34, further comprising a target biomolecule in said first volume or said second volume, wherein said voltage potential induces translocation of said target biomolecule through said nanopore.

Embodiment 36. The system of embodiment 35, wherein said first and second electrodes are further configured to detect a differential electrical signal generated from said passage of said target biomolecule through said nanopore.

Embodiment 37. The system of embodiment 36, wherein said differential signal is a change in current through said nanopore.

Embodiment 38. The system of any one of embodiments 33-37, wherein said ethylene glycol is a polyethylene glycol.

Embodiment 39. The system of embodiment 38, wherein said polyethylene glycol is triethylene glycol, polyethylene glycol 200, or polyethylene glycol 400.

Embodiment 40. The system of any one of embodiments 33-37, wherein said ethylene glycol comprises the structure:

$$\text{HO} \diagup \diagdown \left( \text{O} \diagup \diagdown \right)_n \text{H}$$

wherein n is from 1 to 10.

Embodiment 41. The system of any one of embodiments 33-37, wherein said nanopore sensing solution comprises a salt.

Embodiment 42. The system of embodiment 41, wherein said salt is NaCl, KCl, or LiCl.

Embodiment 43. The system of embodiment 41, wherein said salt is present in said sensing solution at a concentration of greater than 0.01M, greater than 0.02M, greater than 0.05M, greater than 0.1M, greater than 0.2M, greater than 0.5M greater than 1M, greater than 2M, or greater than 3M.

Embodiment 44. The system of any one of embodiments, wherein said target biomolecule is a polynucleotide.

Embodiment 45. The system of embodiment 44, wherein said polynucleotide is a dsDNA, ssDNA, RNA, or RNA/DNA hybrid.

Embodiment 46 The system of embodiment 44, wherein said polynucleotide has a length of no more than 2 kb, 1 kb, 500 bases, 400 bases, 300 bases, 200 bases, or 100 bases.

Embodiment 47. The system of embodiment 45, wherein said target dsDNA is less than 500 bp in length.

Embodiment 48. The system of embodiment 45, wherein said target dsDNA comprises a length of from 10 bp to 500 bp.

Embodiment 49. The system of any one of embodiments 33-37, wherein said nanopore comprises a diameter from 10 nm to 150 nm.

Embodiment 50. The system of any one of embodiments 33-37, wherein said nanopore is characterized by a minimum diameter of greater than 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm or 65 nm.

Embodiment 51. The system of any one of embodiments 33-37, wherein said nanopore is characterized by a minimum diameter of less than 70 nm, 75 nm, 80 nm, 85 nm, 90 nm, 95 nm, 100 nm, 105 nm, or 110 nm.

Embodiment 52. The system of any one of embodiments 33-37, wherein said nanopore has a minimum diameter of less than 1000 nm, less than 500 nm, less than 200 nm, less than 100 nm, or less than 50 nm.

Embodiment 53. The system of any one of embodiments 33-37, wherein the nanopore is characterized by a minimum diameter from 65 nm to 100 nm.

Embodiment 54. The system of any one of embodiments 33-37, wherein the nanopore is characterized by a minimum diameter from 5 nm to 100 nm.

Embodiment 55. The system of embodiment 44, wherein said polynucleotide has a length of no more than 500 bases and said nanopore has a minimum diameter of 10 nm.

Embodiment 56. The system of any one of embodiments 33-37, wherein said sensing solution comprising ethylene glycol is present in both the first volume and the second volume.

The system of any one of embodiments 33-37, wherein said ethylene glycol is present in said first volume or said second volume at a concentration of 0.1% v/v or greater, 0.2% v/v or greater, 0.5% v/v or greater, 1% v/v or greater, 2% v/v or greater, 5% v/v or greater, 10% v/v or greater, 15% v/v or greater, 20% v/v or greater or 25% v/v or greater.

Embodiment 57. The system of any one of embodiments 33-37, wherein said ethylene glycol is present in said first volume or said second volume at a concentration of at least 0.01M, 0.05M, 0.1M, 0.2M, 0.5M or 1M.

Embodiment 58. The system of any one of embodiments 33-37, wherein said device comprises electrodes for applying a voltage across said nanopore and for monitoring an electrical current through said nanopore from one chamber to the other, wherein said electrodes are connected to a power supply.

Embodiment 59. The system of any one of embodiments 33-37, wherein said first and second volume are in fluidic communication only through said nanopore.

5.7.5. Sensors

The systems of the disclosure often include a sensor. A sensor is a device, module, machine, or subsystem whose purpose is to detect events or changes in its environment and send the information to other electronics, frequently a computer processor.

In some applications the sensor can be any sensor known in the art. In certain embodiments, the sensor can be one described in Section 5.5.8.

5.7.6. Computer System

Often the systems of the disclosure can be used in with a computer system, a processor and a computer readable medium, that stores code for processing and analyzing current data from a nanopore device. Variations of the described computer systems are possible so long as they provide for the systems and methods as provided by the disclosure.

FIG. 29A shows an analytics system 100 for monitoring current measurements, performing analytics on that data, and providing summary analytics, according to one embodiment. The analytics system can include a client computing device 110, a nanopore device 130, an application server 125, database server 120, and a network 135. Although FIG. 29A illustrates only a single instance of most of the components of the analytics system 100, in practice more than one of each component may be present, and additional or fewer components may be used.

The client device 110 is a computer system. An example physical implementation is described more completely below with respect to FIG. 29B. Client devices 110 are one or more computing devices capable of receiving user input as well as transmitting and/or receiving data via the network 135. In one embodiment, a client device 110 is a conventional computer system, such as a desktop or a laptop computer. Alternatively, a client device 110 may be a device having computer functionality, such as a personal digital assistant (PDA), a mobile telephone, a smartphone, or another suitable device. In some embodiments, client devices 110 execute an application allowing a user of the client device 110 to interact with other entities on the network, such as servers or other client devices. For example, a client device 110 can in some cases execute a browser application to enable interaction between the client device 110 and the application server 125 or database server 120 via the network 135. In another embodiment, a client device 110 interacts through an application programming interface (API) running on a native operating system of the client device 110, such as IOS® or ANDROID™. With network 135 access, the client device 110 transmits to other entities on the network 135 the data associated with the nanopore device 130.

The nanopore device 130 can include its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 102.11). In one embodiment, the nanopore device is any nanopore device known in the art. In another embodiment, a nanopore device used with the system is one described in Section 5.7.

The application server 125 is a computer or network of computers. Although a simplified example is illustrated in FIG. 29B, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data. Additionally, the computing system includes an operating system, for example, a UNIX operating system, LINUX operating system, or a WINDOWS operating system. The operating system manages the hardware and software resources of the application server 125 and also provides various services, for example, process management, input/output of data, management of peripheral devices, and so on. The operating system provides various functions for managing files stored on a device, for example, creating a new file, moving or copying files, transferring files to a remote system, and so on.

The application server 125 includes a software architecture for supporting access and use analytics system 100 by many different client devices 110 through network 135, and thus at a high level can be generally characterized as a cloud-based system. The application server 125 generally provides a platform for a user 111 and a company 112 to report data recorded by the sensors associated with nanopore device 130.

Generally, the application server 125 is designed to handle a wide variety of data. The application server 125 includes logical routines that perform a variety of functions including checking the validity of the incoming data, parsing and formatting the data if necessary, passing the processed data to a database server 120 for storage, and confirming that the database server 120 has been updated.

The application server 125 stores and manages data at least in part on a user by user basis. Towards this end, the application server 125 creates a user profile for each user. The user profile may further specify a device identifier, such as a unique media access control (MAC) address identifying the one or more client devices 110 or nanopore devices 130 authorized to submit data to the user.

The database server 120 stores data according to defined database schemas. Typically, data storage schemas across different data sources vary significantly even when storing the same type of data including cloud application event logs and log metrics, due to implementation differences in the underlying database structure. The database server 120 may also store different types of data such as structured data, unstructured data, or semi-structured data. Data in the database server 120 may be associated with users.

The network 135 represents the various wired and wireless communication pathways between the client 110 devices, the nanopore device 130, the application server 125, and the database server 120. The network 135 may comprise any combination of local area and/or wide area networks. Network 135 can use, for example, standard Internet communications technologies and/or protocols. Thus, the network 135 can include links using technologies such as Ethernet, 801.11, IEEE 102.11, integrated services digital network (ISDN), asynchronous transfer mode (ATM), worldwide interoperability for microwave access (WiMAX), 3G, 4G, code division multiple access (CDMA), digital subscriber line (DSL), etc. Similarly, the networking protocols used on the network 135 can include the transmission control protocol/Internet protocol (TCP/IP), multiprotocol label switching (MPLS), the hypertext transport protocol (HTTP), the simple mail transfer protocol (SMTP), the file transfer protocol (FTP), etc. The data exchanged over the network 135 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

Generally, the exact physical components used in a client device 110 will vary in size, power requirements, and performance from those used in the application server 125 and the database server 120. For example, client devices 110, which will often be home computers, tablet computers, laptop computers, or smart phones, will include relatively small storage capacities and processing power, but will include input devices and displays. These components are suitable for subject input of data and receipt, display, and interaction with notifications provided by the application server 125. In contrast, the application server 125 may include many physically separate, locally networked computers each having a significant amount of processing power for carrying out the COPD risk analyses introduced above. In one embodiment, the processing power of the application server 125 provided by a service such as Amazon Web Services™. Also in contrast, the database server 120 may include many, physically separate computers each having a significant amount of persistent storage capacity for storing the data associated with the application server.

FIG. 29B is a high-level block diagram illustrating physical components of an example computer 140 that may be used as part of a client device 110, application server 125, and/or database server 120 from FIG. 29A, according to one embodiment. Illustrated is a chipset 150 coupled to at least one processor 145. Coupled to the chipset 150 is volatile memory 155, a network adapter 160, an input/output (I/O) device(s) 165, a storage device 170 representing a non-volatile memory, and a display 175. In one embodiment, the functionality of the chipset 150 is provided by a memory controller 151 and an I/O controller 152. In another embodiment, the memory 155 is coupled directly to the processor 145 instead of the chipset 150. In some embodiments, memory 155 includes high-speed random access memory (RAM), such as DRAM, SRAM, DDR RAM or other random access solid state memory devices.

The storage device 170 is any non-transitory computer-readable storage medium, such as a hard drive, compact disk read-only memory (CD-ROM), DVD, or a solid-state memory device. The memory 155 holds instructions and data used by the processor 145. The I/O device 165 may be a touch input surface (capacitive or otherwise), a mouse, track ball, or other type of pointing device, a keyboard, or another form of input device. The display 175 displays images and other information from for the computer 140. The network adapter 160 couples the computer 140 to the network 135.

As is known in the art, a computer 140 can have different and/or other components than those shown in FIG. 29B. In addition, the computer 140 can lack certain illustrated components. In one embodiment, a computer 140 acting as server 120 may lack a dedicated I/O device 165. Moreover, the storage device 170 can be local and/or remote from the computer 140 (such as embodied within a storage area network (SAN)), and, in one embodiment, the storage device 170 is not a CD-ROM device or a DVD device. As is known in the art, the computer 140 is adapted to execute computer program modules for providing functionality described herein. A module can be implemented in hardware, firmware, and/or software. In one embodiment, program modules are stored on the storage device 170, loaded into the memory 155, and executed by the processor 145.

5.8. Kits

The disclosure provides kits for the detection or characterization of biomolecules using a nanopore device. A kit for detection or characterization of a biomolecule in a sample using a nanopore device can comprise a sensing solution of Section 5.3, and instructions.

The compositions and methods of the disclosure are suited for preparation of kits, and can be readily produced in accordance with well-known procedures. The reagents or components of a kit can include identifying description or label relating to the instructions. A kit may comprise containers that each comprise at least one of the reagents or components provided with the kit.

The disclosure provides kits for conducting the methods of the disclosure. Furthermore, a kit can be customized for a particular application. In some embodiments, a kit can be tailored for characterizing: a presence or absence of, a quantity of, an identity of, a modification of, a structure of, or a sequence of a biomolecule. Often the kit provides improved accuracy as compared to the same method performed in a standard buffer.

Depending on the application, sample type, or user's needs, the kit can have additional reagents or components to conduct the method or application.

In some embodiments, a kit for detection or characterization of a biomolecule in a sample using a nanopore device can comprise a sensing solution of Section 5.3, instructions, and additional reagents or components for sample processing, sample detection, or depending on user's needs (e.g., devices, software, or the like).

The disclosure also provides kits for conducting particular applications that require accurate single-molecule level of identification and characterization. Non-limiting examples of application that the kits can be tailored to, include but are not limited to, diagnostics testing, infectious disease testing, genetic screening, including but not limited, cancer genes, a hereditary locus, genetic modifications such a copy number, mutation, an inserted transgene content, or drug/chemical agent screening.

5.8.1. Sensing Solutions

It is contemplated that any of the sensing solution compositions provided in Section 5.3, can be used with the kits of the disclosure. As discussed herein, a person skilled in the art would readily realize that additional agents can be added to a sensing solution, Any of the polyether agents described herein can be utilized in a sensing solution. In some embodiments, the kits can use a sensing solution comprising an effective amount of a polyether of Formula (I):

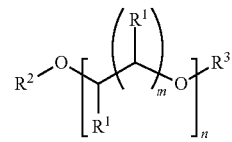

where: m is 1-3; n is 1-30; each $R^1$ is independently H or alkyl (e.g., methyl); and $R^2$ and $R^3$ are each independently H or alkyl (e.g., methyl) or a terminal group, wherein the sensing solution is capable of detecting or characterizing the biomolecule using a nanopore device.

In some embodiments, the kits comprise a sensing solution with an effective amount of a polyether of Formula (Ia)-(IV) or embodiments thereof.

In some embodiments, the kits comprise an asymmetric or gradient sensing solution as described in Section 5.4.4.

5.8.2. Instructions

Often the kit of the disclosure will comprise instructions for using a sensing solution in a nanopore device. The instructions can be on paper, stored in computer code, or provided electronically to a user.

The instructions in a kit can be tailored for a particular method, application, or sample type, characteristics, or biomolecule type. The instruction can be tailored to: diagnostics biomarker testing, infectious disease detection, genetic screening (e.g., genetic locus/mutation or an inserted transgene in a plant), and drug or chemical agent screening. In some embodiment, the instructions can be tailored any application described in Section 5.6.

5.8.3. Additional Kit Reagents and Components

It is contemplated that a kit will be tailored to either a particular method, an application, sample type, characteristics, or biomolecule type. Therefore, a kit will often will have additional components or reagents. Also, in certain embodiment, the additional components and reagents included in a kit will further depend on a user's needs.

In some embodiments, a kit for detection or characterization of a biomolecule in a sample using a nanopore device comprises: a sensing solution, instructions, and one or more components selected from the group consisting of: a buffer (e.g., HEPES, TRIS, or the like), a means for detection such as a probe, a dye, a voltage-sensitive moiety or the like, a carbohydrate solution, an electrode, a power supply, a voltage patch-clamp amplifier, a solution(s) for sample preparation, a nanopore device comprising a membrane, or a combination thereof.

The kit can include any nanopore device known in the art or the devices provided in Section 5.5 of the disclosure. As a skilled artisan will appreciate, the size of the pore in a membrane must be large enough to accommodate the translocation of the target molecule (modified with a detection means, such as a probe or other voltage-sensitive moiety or unmodified) through the membrane. As such, the pore(s) in the nanopore device can be of a nano-scale or micro-scale.

In some applications, the device can have a pore diameter size greater than about 20 nm, about 25 nm, or about 30 nm. In other applications, the device can have a pore diameter size greater than about 60 nm, about 70 nm, about 80 nm, about 90 nm, about 100 nm, about 110 nm, or about 120 nm.

Often a kit can include computer readable media that directs an operating system for detecting or characterizing a biomolecule in a sample or computer readable medium stores code that detects translocations through the nanopore device as transient drops in current and uses an algorithm that identifies events with significant standard deviation as compared to a determined baseline current.

5.9. Examples

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

5.9.1. Example 1: A Standard 1M LiCl Buffer can Detect Larger dsDNA of 3.2 kb or Greater in a 27 nm Nanopore A solid-state nanopore is a nano-scale opening formed in a thin solid-state membrane that separates two aqueous volumes. A voltage-clamp amplifier applies a voltage V across the membrane while measuring the ionic current through the open pore (FIG. 7A). Unlike any other single-molecule sensor, the nanopore device can be packaged into a hand-held form factor at very low cost. When a single charged molecule such as a double-stranded DNA (dsDNA) is captured and driven through the pore by electrophoresis, the measured current changes ($\delta I$) from baseline, generating an event, and the conductance shift depth ($\delta G = \delta I/V$) and duration are used to characterize the event (FIG. 7B).

The value $\delta G$ (also labeled $\Delta G$) can be computed as the mean current change divided by voltage. The value $\delta G$ (also labeled $\Delta G$) can also be computed as the maximum current shift divided by voltage. The duration is computed as the shift width.

We placed 0.1 nM 3.2 kb dsDNA into a nanopore device with a 27 nm diameter nanopore. The buffer solution in the nanopore device included 1M LiCl. We applied a voltage of 100 mV across the nanopore to induce translocation of the dsDNA across the nanopore. Events were detected by the current sensor and analyzed as described below.

After recording many events during an experiment, distributions of the events are analyzed to determine the detection or characteristic of a particular target molecule. FIG. 7C shows the event characteristics for a 3.2 kb dsDNA with a concentration of 0.1 nM passing through a 27 nm diameter nanopore at voltage V=100 mV in a 1M LiCl standard buffer, producing 713 events recorded in 10 minutes.

Conclusion: We observed that larger dsDNA of 3.2 kb or greater can be detected in a 27 nm diameter nanopore using a standard 1M LiCl buffer. See FIG. 7C.

5.9.2. Example 2: A Standard 4M LiCL Buffer is Unable to Detect and Resolve Small dsDNA of 74 bp and 217 bp in a 30 nm Nanopore A shown in Example 1, 1M LiCl buffer can detect large dsDNA. This study was conducted to test the ability of a standard 4M LiCl buffer to detect and resolve small dsDNA (74 bp and 217 bp), using a standard 4M LiCl buffer.

Briefly, different lengths of small double stranded DNA (dsDNA) was prepared double stranded DNA (dsDNA) was prepared at 74 bp and 217 bp in length using PCR amplification. Next, 1-2 ul of the PCR amplified dsDNA was individually diluted in 4.0M LiCl, 10 mM Tris HCl pH 8.8, 1 mM EDTA to yield a final concentration of 5 nM.

Samples were loaded onto a nanopore device with a 29 nm thick SiN membrane with pores of approximately 30 nm in size. Next, 10 ul of the sample was injected into a prototype nanopore chip holder and 100 mV bias was applied to the nanopore chip (trans side positive) using a prototype voltage-clamp amplifier. Ionic current data was recorded using software at a sampling rate of 125 kHz for approximately 5 minutes or enough time to collect ~1000 molecular translocation events. Data was re-filtered at 30 kHz using a 4 pole Bessel filter.

DNA translocations through the pore are detected as transient drops in ionic current. These translocation events were detected from the raw ionic current data using an event finding algorithm that identifies events with significant standard deviations as compared to a baseline current. Representative data is shown in FIGS. 18A-18B.

Conclusion: We observed that a standard 4M LiCl buffer was unable to detect a 74 bp dsDNA and that there was no resolution between 74 bp and 217 bp dsDNA. See FIGS. 18A-18B.

5.9.3. Example 3: Carbohydrate-Based Sensing Solutions are Unable to Detect or Resolve dsDNA Molecules Ranging from 74 bp to 550 bp in a 26 nm Nanopore This study was conducted to test the hypothesis that a carbohydrate-based sensing solution should enhance nanopore detection and resolution of small dsDNA molecules ranging from 74 bp to 550 bp.

Different lengths of small double stranded DNA (dsDNA), 74 bp, 217 bp, 309 bp and 550 bp were generated using standard PCR amplification. Next, 1-2 ul of the PCR amplified dsDNA and then individually diluted in carbohydrate solutions comprising either 20% v/v Glycerol, Sorbitol, Glucose, Maltose, or Maltodextran in 4.0M LiCl, 10 mM Tris HCl pH 8.8, 1 mM EDTA.

Next, the samples were loaded on a nanopore device with a 29 nm thick SiN membrane with pores of approximately 26 nm in size. 10 ul of the sample was injected into a nanopore chip holder and 100 mV bias was applied to the nanopore chip (trans side positive) using a voltage-clamp amplifier.

Raw ionic current data was recorded using software at a sampling rate of 125 kHz for approximately 5 minutes or enough time to collect approximately 1000 molecular translocation events. Data was re-filtered at 30 kHz using a 4 pole Bessel filter. The data collected from the 20% Maltose sensing solution is shown in FIGS. 19A-19B. Data from Glycerol, Sorbitol, Glucose, Maltose, or Maltodextran are not shown.

Conclusion: Our results indicate that carbohydrate-based sensing solutions generally are not effective for detecting and resolving small dsDNA. We detected no events using either a Glycerol, a Sorbitol, a Glucose, or a Maltodextran-based sensing solution (data not shown).

Further, the 20% Maltose carbohydrate sensing solution was unable able to efficiently detect the 74 bp dsDNA, detecting only 2 events after 5 mins. As such, the 74 bp dsDNA was essentially undetectable. In addition, the data indicates that there is no resolution between 74 bp and 217 bp dsDNA. See FIGS. 19A-19B. Lastly, although the 217 bp dsDNA was detectable, it was unresolvable from larger dsDNA of 309 bp, 550 bp (data not shown).

Figure 2:
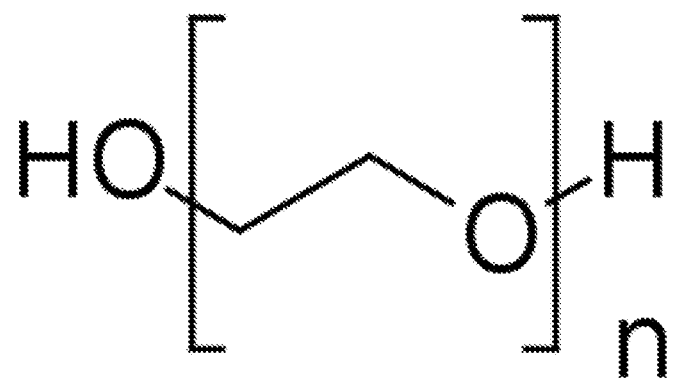
FIG. 2 illustrates the structure of a single unit of ethylene glycol, the repeating unit that makes up polyethylene glycol (PEG).

5.9.4. Example 4A: 7% PEG 200 Sensing Solution Detects and Discriminates a 217 bp from a 353 bp dsDNA and is Able to Quantify dsDNA Molecules We tested sensing solution comprising a short PEG agent comprising, 7% PEG 200 v/v, 4M LiCl, 10 mM Tris, 1 mM EDTA, pH 8.8 to determine if this solution can detect and differentiate a 217 bp dsDNA from a 353 bp dsDNA in a 35 nm nanopore. FIG. 2 illustrates the structure of a single unit of ethylene glycol, the repeating unit that makes up polyethylene glycol (PEG).

Each fragment, 217 bp dsDNA and 353 bp dsDNA, was ran in isolation, and their respective event populations were plotted according to dwell time and their current blockade (FIG. 4A). The fragments exhibited distinct dwell times (FIG. 4B). A histogram depicting the max current blockade of each population indicates that 353 bp blocks more current compared to 217 bp (FIG. 4C).

A 50/50 mixture of 217 bp and 353 bp was ran and used as a calibrant for downstream calculation of % of 217 bp in solution. A histogram of the dwell time of the 50/50 calibrant was compared to those of known mixtures of the two fragments containing 25% or 75% 217 bp respectively (FIG. 4D).

The quantity (e.g., concentration) estimates of number of dsDNA molecules for a particular fragment can be determined as described in described WO2018081178, which is incorporated herein by reference. Briefly, the dsDNA molecules were estimated by the following method. As the percentage of the 217 bp dsDNA increases in the sample, the peak representing the 217 bp dsDNA fragment progressively increases moving from 25% to 50%, and 75%. Similarly, histograms comparing other event signature parameters including area can be generated (FIG. 4E). These characteristics can then be used to estimate the % of 217 bp in solution.

Conclusion: The 25% and 75% mixtures were estimated to be 22.99% and 76.61% respectively. Taken together, these results suggest that a 7% PEG 200 sensing can detect and discriminate between 217 bp and 353 bp dsDNA, thereby allowing accurate fractional abundance estimations.

5.9.5. Example 4B: 10% PEG 200 Sensing Solution can Detect and Discriminate 108 bp and 309 bp dsDNA in a 28 nm Nanopore by Dwell Time or Maximum Current Blockade We tested sensing solution comprising a short PEG agent comprising, 10% PEG 200 v/v, 4M LiCl, 10 mM Tris, 1 mM EDTA, pH 8.8 to determine if this solution can detect and differentiate a 108 bp dsDNA from a 309 bp dsDNA in a 28 nm nanopore (100 mV applied voltage) by its log dwell time (e.g., event duration) or by its maximum current blockade.

Each DNA fragment was run in isolation, and their respective populations plotted on an all event plot according to the observed event duration (seconds) and maximum current blockade (nanosiemens; FIG. 3A). FIG. 3B shows event durations of the 108 bp and 309 bp dsDNA populations on a log scale. FIG. 3C shows the maximum depth of events in each of the 108 bp and 309 bp populations in a histogram.

Conclusion: We observed that 108 bp dsDNA molecule and the 309 bp dsDNA molecule exhibit very distinct event durations based on the log dwell time, and the populations separate clearly (FIG. 3B) in a 10% PEG 200 sensing solution. Similarly, the 309 bp and the 108 bp dsDNA each gives distinct difference in the maximum current blockade in the PEG sensing solution. See, FIG. 3A. These data suggest that a PEG buffer shorter in length may by effective for enhancing nanopore detection.

5.9.6. Example 5: 25% TEG Sensing Solution Detects and Discriminates dsDNA of 74 Bp, 108 bp, and 217 bp Run in Isolation The purpose of this study was to determine if a 25% TEG sensing solution can discriminate between dsDNA of different lengths ranging from 74 bp to 217 bp.

Figure 1:
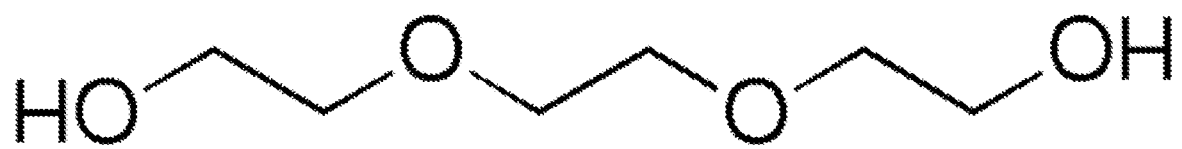
FIG. 1 illustrates the structure of triethylene glycol (TEG).

The structure of TEG is shown in FIG. 1. We tested sensing solution comprising triethylene glycol 25% (v/v), 3M LiCl, 10 mM Tris, 1 mM EDTA, pH 8.8 to determine if this solution can detect and differentiate a 74 bp dsDNA from a 108 bp and a 217 bp dsDNA in a 28 nm nanopore (100 mV applied voltage) by its log dwell time (e.g., event duration) or by its maximum current blockade Each dsDNA fragment 74 bp, 108 bp, and 217 bp was ran in isolation in a 28 nm nanopore. Representative data is shown in FIGS. 5A-5D. Each dsDNA fragment was readily detected forming, three populations (FIG. 5A). Distinct dwell times were observed for each DNA fragment (FIG. 5B), as well as different current blockades (FIG. 5C). The area of each event population shows distinct population peaks (FIG. 5D).

Conclusion: These results demonstrate that a 25% TEG-based sensing solution can detect and discriminates between 74 bp, 108 bp, and 217 bp dsDNA by either their distinct dwell times or current blockades. These data suggest that a 25% TEG-based sensing solutions can be used to multiplex at least three separate DNA fragments simultaneously for detection, discrimination, and quantification.

5.9.7. Example 6: 15% TEG Sensing Solution Enhances Detection and Resolution of Small dsDNA 74 bp, 108 bp, 217 bp, and 309 bp Run in Isolation, as Compared to a Standard 4M LiCl Buffer A panel of dsDNA fragments spanning 108 bp-309 bp were analyzed individually in a 71-73 nm nanopore, with a 15% TEG (v/v) sensing solution and with a standard 4M LiCl buffer.

Conclusion: In the standard 4M LiCl buffer we observed that the 108 bp dsDNA was undetectable. However, both 217 bp and 309 bp dsDNA were detected at modest rates, approximately 42 and 47 events/minute, respectively. However, we observed that these two populations do not differ in either event populations, in dG or dwell time, and therefore the standard 4M LiCl buffer gave considerable overlap between the 217 bp and 309 bp dsDNA. See FIG. 6A.

In contrast, the 15% TEG (v/v) sensing solution resulted in a sharp increase in detection rate as well as separation among the dsDNA populations tested. The 15% TEG sensing solution detected the 108 bp dsDNA at 28 events/minute, while 217 bp dsDNA rose to 307 events/minute, and 309 bp dsDNA increased to 256 events/minute. In addition, the 15% TEG sensing solution showed an increase in dG and dwell time resulted in increased separation of each population. See FIG. 6B. These data suggest that a TEG-based sensing solution can be used to multiplex at least three separate DNA fragments simultaneously for detection, discrimination, and quantification.

5.9.8. Example 7: 30% Ethylene Glycol Sensing Solution Enhances Detection and Resolution of Small dsDNA 108 bp and 309 bp in a 37 nm Nanopore This study was conducted to test the ability of a 30% Ethylene glycol sensing solution to detect and resolve small dsDNA individual populations, as compared to a standard 4M LiCl buffer shown in FIGS. 18A-18B.

Different sizes of dsDNA were prepared, 74 bp, 217 bp, 108 bp, and 309 bp, using standard PCR amplification. The PCR amplified dsDNA were ran in isolation and diluted in 30% Ethylene Glycol (v/v), 4.0M LiCl, 10 mM Tris HCl pH 8.8, 1 mM EDTA to a final concentration of 5 nM.

Next, the samples were loaded on to a solid-state nanopore device with a 29 nm thick SiN membrane with pores of approximately 37 nm in size. 10 ul of the prepared sample was injected into a nanopore chip holder and 100 mV bias was applied to the nanopore chip (trans side positive) using a prototype voltage-clamp amplifier.

Raw ionic current data was recorded using custom software at a sampling rate of 125 kHz for approximately 5 minutes or enough time to collect ~1000 molecular translocation events. Data was re-filtered at 30 kHz using a 4 pole Bessel filter. Representative data is shown in FIGS. 20A-20B.

Conclusion: We observed that small dsDNA fragments of 108 bp and 309 bp are robustly detected in the 30% Ethylene glycol sensing solution as compared to a standard LiCl buffer. Additionally, the 30% Ethylene glycol sensing solution showed resolution between 108 bp and 309 bp dsDNA not observed in the standard LiCl. However, the 30% Ethylene glycol sensing solution appears not as able to detect dsDNA fragments with a smaller difference in lengths, such as 74 bp and 217 bp dsDNA.

5.9.9. Example 8: 15% Triethylene Glycol (TEG) Sensing Solution is Able to Detect and Resolve Small dsDNA 74 bp and 217 bp in a 30 nm Nanopore This study was conducted to test the ability of a 15% Triethylene glycol (TEG) nanopore sensing solution to detect and resolve small dsDNA populations individually, as compared to a standard LiCl buffer shown in FIGS. 18A-18B.

Different lengths of small double stranded DNA (dsDNA) were prepared, 74 bp and 217 bp, using standard PCR amplification. The PCR amplified dsDNA were ran in isolation and diluted in 15% TEG (v/v), 4.0M LiCl, 10 mM Tris HCl pH 8.8, 1 mM EDTA to a final concentration of 5 nM.

Samples were loaded on a solid-state nanopore device with a 29 nm thick SiN membrane with a pore of approximately 30 nm in size. 10 ul of the sample was injected into a prototype nanopore chip holder and 100 mV bias was applied to the nanopore chip (trans side positive) using a prototype voltage-clamp amplifier.

Raw ionic current data was recorded using software at a sampling rate of 125 kHz for approximately 5 minutes or enough time to collect ~1000 molecular translocation events. Data was re-filtered at 30 kHz using a 4 pole Bessel filter. Representative data is shown in FIGS. 21A-21B.

Conclusion: We observed that the 15% TEG sensing solution was able to detect and resolve 74 bp and 217 bp dsDNA from each other, unlike a standard LiCl buffer.

5.9.10. Example 9: 10% Tripropylene Glycol (TPG) Sensing Solution can Detect and Resolve Small dsDNA Molecules 74 bp and 217 bp in a 30 nm Nanopore This study was conducted to test the ability of a 10% Tripropylene glycol (TPG) nanopore sensing solution to detect and resolve small DNA populations of as compared to a standard LiCl buffer shown in FIGS. 18A-18B.

Two different sizes of double stranded DNA (dsDNA) were prepared, 74 bp and 217 bp, using standard PCR amplification. The PCR amplified dsDNA was ran in isolation and diluted in 10% TPG (v/v), 4.0M LiCl, 10 mM Tris HCl pH 8.8, 1 mM EDTA to a final concentration of 5 nM.

Samples were loaded on a solid-state nanopore device with a 29 nm thick SiN membrane with a pore of approximately 30 nm in size. 10 ul of the sample was injected into a nanopore chip holder and 100 mV bias was applied to the nanopore chip (trans side positive) using a voltage-clamp amplifier.

Raw ionic current data was recorded using software at a sampling rate of 125 kHz for approximately 5 minutes or enough time to collect ~1000 molecular translocation events. Data was re-filtered at 30 kHz using a 4 pole Bessel filter. Representative data is shown in FIGS. 22A-22B.

Conclusion: Our results indicate that the 10% TPG sensing solution was able to detect and resolve 74 bp and 217 bp dsDNA from each other in, unlike a standard LiCl buffer.

5.9.11. Example 10: 10% Tetraethylene Glycol Dimethyl Ether (TTEG-DME) Sensing Solution Gave Robust Detection and Resolution of Small dsDNA of 108 bp and 217 bp in a 31 nm Nanopore This study was conducted to test the ability of a 10% Tetraethylene glycol dimethyl ether (TTEG-DME) nanopore sensing solution to detect and resolve small DNA populations of as compared to a standard LiCL buffer shown in FIGS. 18A-18B.

Different lengths of double stranded DNA (dsDNA) was prepared: 108 bp and 217 bp using standard PCR amplification. Next, the PCR amplified dsDNA samples were then individually diluted in 10% TTEG-DME (v/v), 4.5M LiCl, 10 mM Tris HCl pH 8.8, 1 mM EDTA to a final concentration of 5 nM.

Samples were loaded on to a nanopore device with a 29 nm thick SiN membrane with a pore of approximately 31 nm in size. 10 ul of the sample was injected into a nanopore chip holder and 100 mV bias was applied to the nanopore chip (trans side positive) using a voltage-clamp amplifier.

Raw ionic current data was recorded using software at a sampling rate of 125 kHz for approximately 5 minutes or enough time to collect ~1000 molecular translocation events. Data was re-filtered at 30 kHz using a 4 pole Bessel filter. Representative data is shown in FIGS. 23A-23B.

Conclusion: We observed that the 10% TTEG-DME sensing solution gave robust detection and resolution of small dsDNA of 108 bp and 217 bp, unlike a standard LiCl buffer.

5.9.12. Example 11: 10% Tripropylene Glycol Monomethyl Ether (TPG-MME) Sensing Solution Gave Robust Detection and Resolution of Small dsDNA 108 bp, 217 bp in a 34 nm Nanopore This study was conducted to test the ability of a 10% Tripropylene glycol monomethyl ether (TPG-MME) nanopore sensing solution to detect and resolve small DNA populations of as compared to a standard LiCl buffer shown in FIGS. 18A-18B.

Different sizes of double stranded DNA (dsDNA) were prepared, 108 bp and 217 bp, using standard PCR amplification. Next, the PCR amplified samples were individually ran and diluted in 10% TPG-MME (v/v), 4.5M LiCl, 50 mM Tris HCl pH 8.8, 5 mM EDTA to a final concentration of 5 nM.

Samples were loaded on a solid-state nanopore device with a 29 nm thick SiN membrane with pores of approximately 34 nm in size. 10 ul of the sample was injected into a nanopore chip holder and 100 mV bias was applied to the nanopore chip (trans side positive) using a voltage-clamp amplifier.

Raw ionic current data was recorded using custom software at a sampling rate of 125 kHz for approximately 5 minutes or enough time to collect ~1000 molecular translocation events. Data was re-filtered at 30 kHz using a 4 pole Bessel filter. Representative data is shown in FIGS. 24A-24B.

Conclusion: 10% TPG-MME sensing solution gave robust detection and resolution of small dsDNA of 108 bp and 217 bp, unlike a standard LiCl buffer.

5.9.13. Example 12: Example 12: Asymmetric 10% PEG 200 (Cis)/10% Maltose (Trans) Sensing Solutions can Detection Small dsDNA 88 bp and 266 bp in a 33 nm Nanopore This study was conducted to test the effectiveness of an asymmetric PEG 200 sensing solution either on the cis or the trans side of a solid-state nanopore device.

Different lengths of double stranded DNA (dsDNA) were prepared, 88 bp and 266 by PCR amplification. Next, the PCR amplified dsDNA samples were diluted individually at 1:100 in the following sensing solutions as outlined below.

First, we tested a solid-state nanopore device with asymmetric PEG sensing solution on the cis side. The device was set-up such that the 10% PEG (v/v), 4.5M LiCl, 50 mM Tris HCl pH 8.8, 5 mM EDTA solution was on the cis side of the pore and the 10% Maltose w/v, 4.5M LiCl, 50 mM Tris HCl pH 8.8, 5 mM EDTA solution was on the trans side of the pore. Samples were diluted into 10% PEG 200 v/v, 4.5M LiCl, 50 mM Tris HCl pH 8.8, 5 mM EDTA to match the cis chamber.

The samples were loaded on a solid-state nanopore device with a 29 nm thick SiN membrane with a pore approximately 33 nm in size. 10 ul of the sample was injected into a nanopore chip holder and 100 mV bias was applied to the nanopore chip (trans side positive) using a voltage-clamp amplifier. Representative data is shown in FIGS. 25A-25B.

Next, we tested a solid-state nanopore device with asymmetric maltose sensing solution on the cis side. The device was set-up such that the 10% Maltose w/v, 4.5M LiCl, 50 mM Tris HCl pH 8.8, 5 mM EDTA solution was on the cis side of the pore and the 10% PEG 200 v/v 4.5M LiCl, 50 mM Tris HCl pH 8.8, 5 mM EDTA solution was on the trans side of the pore. Sample was diluted into 10% maltose w/v, 4.5M LiCl, 50 mM Tris HCl pH 8.8, 5 mM EDTA to match the cis side chamber and 10 ul was injected into a nanopore chip holder.

The samples were loaded on a solid-state nanopore device with a 29 nm thick SiN membrane with a pore approximately 33 nm in size. 10 ul of the sample was injected into a nanopore chip holder and 100 mV bias was applied to the nanopore chip (trans side positive) using a voltage-clamp amplifier. Representative data is shown in FIGS. 26A-26B

For each test, raw ionic current data was recorded using software at a sampling rate of 125 kHz for approximately 5 minutes or enough time to collect ~1000 molecular translocation events. Data was re-filtered at 30 kHz using a 4 pole Bessel filter.

Conclusion: We observed that a nanopore device with a 10% Maltose sensing solution on the cis side and a 10% PEG sensing solution was on the trans side of the pore only weakly able to detect and did not resolve dsDNA populations 88 bp and 266 bp. See FIGS. 26A-26B.

However, a nanopore device with a 10% PEG sensing solution was on the cis and a 10% maltose sensing solution was on the trans side of the pore can detect and resolve small dsDNA of 88 bp and 266 bp. See FIGS. 25A-25B.

5.9.14. Example 13: PEG 8000 Sensing Solution is Unable to Detect or Only Provides Minimal Detection and is Unable to Resolve Small DNA Molecules in a 32 nm Nanopore This study was conducted to determine the ability of a longer PEG, a PEG 8000 sensing solution to detect and resolve small dsDNA molecules compared to shorter PEGs tested above.

Different lengths of double stranded DNA (dsDNA) were prepared, 74 bp, 217 bp, 309 bp, and 500 bp, using a standard PCR amplification. Next, the PCR amplified dsDNA was individually diluted in 75 µM PEG 8000, 2.0M LiCl, 10 mM Tris HCl pH 8.8, 1 mM EDTA at a final concentration of 5 nM.

Samples were loaded on a nanopore device with a 29 nm thick SiN membrane with pores of approximately 32 nm in size. Approximately 10 ul of diluted sample was injected into a prototype nanopore chip holder and 100 mV bias was applied to the nanopore chip (trans side positive) using a prototype voltage-clamp amplifier.

Raw ionic current data was recorded using software at a sampling rate of 125 kHz for approximately 5 minutes or enough time to collect ~1000 molecular translocation events. Data was re-filtered at 30 kHz using a 4 pole Bessel filter. Representative data is shown in FIGS. 27A-27B and FIGS. 28A-28B.

Conclusion: We observed almost no detection of the of 74 bp dsDNA and no resolution between 74 bp and 217 bp dsDNA populations using a PEG 8000 sensing solution. Arrows point out three of the twelve 74 bp events detected. See, FIGS. 27A-27B. Further, we observed minimal detection of dsDNA of 217 bp and 309 bp in size in a PEG 8000 buffer, and no resolution of 217 bp and 309 bp dsDNA, as shown by the completely overlapping populations in the histogram. See FIGS. 28A-28B.

Taken together, our results provided in the Examples above, suggest that sensing solutions of the disclosure, an particularly the one comprising a shorter polyether agent, provide more effective sensing of biomolecules of various sizes in a nanopore device than the other agents and various standard buffers tested.

Because the size of dsDNA molecules tested approximate those of protein molecules, the sensing solutions of the disclosure may also be applied for the detection of peptides, proteins, and antibodies.

In Examples 14-21 provided below, we focused on testing nanopore sensing solutions comprising cation-salt agents and compared the performance of these to other standard (e.g., conventional) nanopore buffers.

Here, we tested of DNA lengths below 500 bp and using nanopores with diameters of at least 25 nm. Pores used in the examples below were formed in 30 nm silicon nitride membranes using a helium ion microscope (HIM). In the examples, the amplified dsDNA fragments were cleaned and purified using a DNA cleanup kit (New England BioLabs, Cat. #T1030S).

For the following examples, a current signal is flagged as an event and extracted when the sample falls below 6 times the standard deviation ($\sigma$) of the open channel signal, with a computed using the period between every pair of flagged events. Events are rejected from the analysis if: they do not return to within $1\sigma$; if the signal-to-noise ratio of the minimum sample divided by a is less than 6; or if the duration exceeds 10 ms. For each event, the reported duration is the time-width at half maximum. Each event $\delta G$ value is the mean of all samples below 1a after trimming the number samples at the start and end of the event that correspond to the rise time (tr), thereby removing the effects of the low-pass filter. The value for tr is determined by the amplifier and bandwidth setting, as follows: Using the MultiClamp 700B (Molecular Devices, LLC) with an effective bandwidth matching the 30 kHz Bessel filter bandwidth, the 10-90 rise time (tr) is 12 $\mu$s. For events shorter than 2 tr, we report the maximal value of $\delta G$.

5.9.15. Example 14: 1M LiCl or 1M KCl Standard Buffers Cannot Detect Small dsDNA of 108 bp in a 27 nm or a 30 nm Nanopore This study was conducted to determine whether 108 bp dsDNA is detectable in solid-state nanopores with diameters of 27 nm and 30 nm using standard 1M LiCl or 1M KCl buffers.

Briefly, we added buffer comprising 1M LiCl or 1M KCl to the cis and trans volumes of a nanopore device comprising either a 27 nm diameter nanopore or a 30 nm diameter nanopore.

Next, we added a sample containing 108 bp dsDNA to the cis volume of a nanopore device a final concentration of 10 nM. Then we applied a 100 mV potential across the nanopore to induce translocation and detection of the 108 bp dsDNA. During application of the voltage potential, the ionic current passing through the nanopore was continuously monitored.

The signal generated by the current was then analyzed for the presence of events triggered by translocation of 108 bp dsDNA molecules through the 27 nm nanopore. FIGS. 8A-8B show a plot of events detected from the above experiment characterized by the change in current (Max $\delta G$), and event duration(s).

Conclusion: No events were detected in the 27 nm diameter nanopore containing a 1M KCl or 1M LiCl standard buffer. Similarly, no events were detected in the 30 nm diameter nanopore containing a standard 1M KCl or 1M LiCl buffer. Our results indicate that detection of smaller molecules, such as 108 bp dsDNA, in larger nanopores is not possible using standard nanopore buffers 1M KCl or 1M LiCl. See FIGS. 8A-8B.

5.9.16. Example 15: 1 M CsCl Sensing Solution can Detect Small dsDNA of 108 bp in a 27 Nm and a 30 nm Nanopore After our above study showed that neither a 1M LiCl nor a 1M KCl buffer could detect a 108 bp dsDNA in a 27 nm and 30 nm nanopore device, we tested the ability of a 1M CsCl sensing solution to detect a 108 bp dsDNA in a 27 nm and 30 nm nanopores.

Cesium chloride (Fisher Scientific, Cat. #BP1595-1) based nanopore recording buffer was prepared containing a final concentration of 10 mM Tris and 1 mM EDTA at pH 8.8. Following preparation, the buffer was sterile filtered using a 0.22 um membrane (Millipore, Cat. #SCGP00525), and degassed for a period of 30 minutes prior to its introduction to the nanopore.

The 1M CsCl sensing solution was applied to the cis and trans volumes of a nanopore device comprising either a 27 nm diameter nanopore or a 30 nm diameter nanopore.

We loaded the dsDNA sample a final concentration of 10 nM to the cis volume of a nanopore device with a 27 nm diameter. Next, we applied a 100 mV potential across the nanopore to induce translocation and detection of the 108 bp dsDNA. During application of the voltage potential, the ionic current passing through the nanopore was continuously monitored. The signal generated by the current was then analyzed for the presence of events triggered by translocation of 108 bp dsDNA molecules through the 27 nm nanopore. FIG. 8A shows a plot of events detected from the above experiment characterized by the change in current (Max $\delta G$), and event duration (s). FIG. 8B shows a plot of events correlated with the detection of 108 bp dsDNA in the 30 nm diameter nanopore containing 1M CsCl buffer.

Conclusion: We observed that the 27 nm device comprising a 1M CsCl was able to detect 108 bp dsDNA, with a capture rate of 88/min. Similarly, the 30 nm diameter nanopore device with 1M CsCl was able to detect 108 bp dsDNA, with a capture rate of 66/min. Our results indicate that detection of smaller molecules, such as 108 bp dsDNA, easily detectable using a 1M CsCl sensing solution but not in a standard LiCl or KCL buffer. See FIGS. 8A-8B.

5.9.17. Example 16: 1M CaCl$_2$ Sensing Solution Detects Small dsDNA of 108 bp and 74 bp in a 53 nm and a 73 nm Nanopore The purpose of this study was to test the ability of a 1M CaCl$_2$ sensing solution to detect small dsDNA. In addition to CsCl shown above, we discovered that a CaCl$_2$ sensing solution allows for the detection of small biomolecules in large nanopores.

A 53 nm diameter and a 73 nm diameter solid-state nanopore devices with a 1M CaCl$_2$ in the cis and trans volumes of each device. We added a sample containing 108 bp dsDNA or 74 bp dsDNA at a final concentration of 10 nM to the cis volume and applied a voltage of 100 mV or 150 mV across the nanopore. Signal was collected and analyzed as described in Example 14.

FIG. 16A shows a plot of events generated from 10 nM 108 bp dsDNA in a 53 nm diameter nanopore with 1M $CaCl_2$ sensing solution run at 100 mV (square) and 150 mV (circle). FIG. 16B shows a plot of events generated from 10 nM 74 bp dsDNA in a 53 nm diameter nanopore with buffer including 1M $CaCl_2$ run at 100 mV (square) and 150 mV (circle).

FIG. 17 also shows a plot of events generated from 10 nM 74 bp dsDNA in a 73 nm diameter nanopore with 1M $CaCl_2$ sensing solution run at 100 mV.

Conclusion: Our results indicate that a 1M $CaCl_2$ sensing solution can easily detect a 108 bp and 74 bp dsDNA with a 53 nm diameter nanopore. Likewise, we observed that a 1M $CaCl_2$ sensing solution can also detect 74 bp dsDNA with a 73 nm nanopore.

5.9.18. Example 17: 2M and 3M CsCl Sensing Solution Enhanced Signal-to-Noise Ratio, Useful for the Detection of Smaller Molecules in Larger Pores The purpose of this study was to determine how the different concentrations of CsCl sensing solution affect small molecule detection in a large nanopore. We discovered that high molarity of CsCl boosts the signal-to-noise ratio for events generated by translocation of 108 bp DNA through the solid-state nanopore with 30 nm nanopores.

In a 30 nm diameter solid-state nanopore we tested individually 1M CsCl, 2M CsCl, or 3M CsCl in both the cis and trans chambers of the device.

We loaded the sample containing 108 bp dsDNA to the cis volume at a final concentration of 10 nM and applied a voltage of 100 mV across the nanopore. Signal from the nanopore device was collected and analyzed as described in Example 14.

FIG. 9A shows the events detected with buffer at 1M CsCl (diamond), at 2M CsCl (square), and at 3M CsCl (circle). FIG. 9B shows a probability histogram for events detected for each buffer based on the change in current ($\delta G$).

Conclusion: We observed that higher concentrations of CsCl enhanced detection signal-to-noise ratio, as indicated by the shift in the distribution of events to a larger maximum $\delta G$ from 1M CsCl to 2M CsCl, and from 2M CsCl to 3M CsCl. See FIGS. 9A-9B. This enhanced signal-to-noise ratio facilitates detection smaller molecules in larger nanopores. Furthermore, we observed that the normalized capture rate constant increases more than 10-fold from isocratic 1M CsCl (7/nM*min) to 2M CsCl (98/nM*min). However, capture rate did not increase from 2M CsCl to 3M CsCl (53/nM*min).

5.9.19. Example 18: CsCl Gradient Sensing Solution with Increased Molarity, Further Enhanced the Signal-to-Noise Ratio This study was conducted to determine the affect of increasing molarity CsCl gradients on the signal-to-noise ratio generated by small molecules passing through a larger nanopore.

A solid-state nanopore devices with pores of 30 nm diameter were individually ran with higher concentration of CsCl in the cis volume and a lower concentration of CsCl in the trans volume in order to establish a gradient of CsCl. Specifically, the following gradients were tested with increasing molarity: 1M/0.5M CsCl, 2M/1M CsCl, or 3M/1.5M CsCl (represented as cis volume/trans volume concentrations).

Next, we added a sample containing 108 bp dsDNA to the cis volume at a final concentration of 10 nM 108 bp dsDNA. Voltage of 100 mV was applied across the nanopore. Signal was collected and analyzed as described in Example 14.

FIG. 10A shows a plot of events generated from 10 nM 108 bp dsDNA in a 30 nm nanopore with buffer at 1M/0.5M CsCl (diamond), 2M/1M CsCl (square), and 3M/1.5M CsCl (circle), where the concentrations are of the cis/trans chamber of the nanopore device on either side of the nanopore. The normalized capture rates for each gradient increase with the concentration of CsCl used (7/nm*min for 1M/0.5M CsCl, 20/nm*min for 2M/1M CsCl, and 61/nM*min for 3M/1.5M CsCl). FIG. 10B shows a distribution of Max $\delta G$ obtained for each sample. When compared with a similar plot in FIG. 9, which uses an isocratic buffer, we observe that the use of the gradient increases the signal-to-noise ratio to enhance detection of the small molecule in the larger nanopore.

Conclusion: We observed that CsCl gradient sensing solution further enhanced detection signal-to-noise ratio. Furthermore, we observed that higher concentrations of CsCl gradients sensing solutions showed a continued increase in capture rate at higher molarity and that the use of the gradient increases the signal-to-noise ratio. For example, the peak of the probability curve for Max $\delta G$ is around 2 nS when the buffer used is a gradient of 3M/1.5M CsCl in the cis/trans volumes, while the peak of the probability curve for Max $\delta G$ is around 1.2 nS when using 3M CsCl in both chambers.

5.9.20. Example 19: CsCl Gradient 3M/1.5M Sensing Solution Detects of Smaller dsDNA of 74 bp and 109 bp in a 90 nm and a 120 nm Nanopore We used a nanopore device with a 3M/1.5M CsCl gradient (cis/trans volume) to detect 109 bp and 74 bp dsDNA amplification product in a pore with a diameter of 90 nm.

dsDNA fragments 109 bp and 74 bp in length were generated using Taq polymerase according to the manufacturer's specifications (Biotium, Cat. #31014). Following amplification, the dsDNA fragments were cleaned and purified using a DNA cleanup kit (New England BioLabs, Cat. #T1030S). The concentration of the amplicons was determined using a Qubit 3 fluorometer (ThermoFisher, Cat. #Q33216), and then diluted down to the indicated concentration in nanopore recording buffer for nanopore analysis.

We added a sample containing 13 nM 109 bp dsDNA amplicon or 20 nM 74 bp dsDNA amplicon from the amplification reaction to the cis chamber of the nanopore device and applied a voltage of 100 mV across the nanopore for each of the samples. Signal was collected and analyzed as described in Example 14.

FIG. 14 shows a plot of events detected in a 3M/1.5M CsCl gradient sensing solution with a 90 nm nanopore for a 109 bp dsDNA sample with a concentration of 13 nM or a 74 bp dsDNA sample with a concentration of 20 nM.

Conclusion: We observed detection of 13 nM 109 bp dsDNA amplicon and 20 nM 74 bp dsDNA amplicon using a 90 nm diameter nanopore with a 3M/1.5M CsCl gradient buffer. As shown, both 109 bp dsDNA and 74 bp dsDNA could be easily detected. See FIG. 14.

Next, we used a nanopore device with a 3M/1.5M CsCl gradient to detect 109 bp, 74 bp, and 58 bp dsDNA amplification products with a 102 nm nanopore.

dsDNA amplification fragments of 109 bp, 74 bp, and 58 bp in length were generated as described above. We added a sample containing 13 nM 109 bp dsDNA amplicon, 1.3 nM 109 bp dsDNA amplicon, 20 nM 74 bp dsDNA amplicon, 6.66 nM 74 bp dsDNA amplicon, or 20 nM 58 bp dsDNA amplicon from the amplification reaction to the cis chamber of the nanopore device and applied a voltage of 100 mV across the nanopore for each of the samples. Signal was collected and analyzed as described in Example 14.

FIG. 15 shows the results from nanopore detection of each of the above-described samples using a 102 nm diameter nanopore with a 3M/1.5M CsCl gradient sensing solution.

Conclusion: We observed that a 58 bp, 74 bp, and 109 bp dsDNA could be easily detected in a 102 nm nanopore using the CsCl buffer. Furthermore, nearly all events detected reach full depth (duration >=72 us) in both the 90 nm and 102 nm diameter pores. Capture rates (events/min) for each dsDNA amplicon at the indicated concentration are shown in FIG. 15.

5.9.21. Example 20: CsCl Gradient 3M/1.5M Sensing Solution can Detect Small dsDNA of 58 bp, 74 bp, and 108 bp in a 65 nm Nanopore The purpose of this study was to test a nanopore device with a 3M/1.5M CsCl gradient (cis/trans chamber) is able to detect a 58 bp dsDNA, 74 bp dsDNA, or a 108 bp dsDNA in a solid-state nanopore with a 65 nm diameter nanopore.

Specifically, we provided a 65 nm diameter solid-state nanopore with 3M CsCl in the cis volume and 1.5M CsCl in the trans volume. To individual devices, we added a sample containing 108 bp dsDNA (10 nM final concentration), 74 bp dsDNA (5 nM final concentration), or 58 bp dsDNA (16 nM final concentration) to the cis volume of the nanopore device and applied a voltage of 100 mV across the nanopore. Signal was collected and analyzed as described in Example 14. Representative data generated from each 58 bp dsDNA, 74 bp dsDNA, and 108 bp dsDNA sample in the CsCl gradient 3M/1.5M sensing solution in shown in FIGS. 11A-11C. FIG. 11A shows a plot of events detected for a 58 bp dsDNA sample. FIG. 11B shows a plot of events detected for a 74 bp dsDNA sample. FIG. 11C shows a plot of events detected for a 108 bp dsDNA sample.

Conclusion: We observed that the CsCl gradient 3M/1.5M sensing solution can detect a 58 bp, a 74 bp, and a 108 bp dsDNA sample with a 65 nm nanopore in isolation.

5.9.22. Example 21: CsCl Gradient 3M/1.5M Sensing Solution can Easily Detect Small dsDNA of 109 bp in 25 nm and 32 nm Nanopores at Low Concentrations (20 PCR Cycles)

The purpose of this study was to test a nanopore device with a 3M/1.5M CsCl gradient sensing solution to detect 109 bp dsDNA at various concentrations and different voltages in 25 nm or 32 nm nanopores.

Samples ran on a 25 nm diameter solid-state nanopore with a 3M CsCl in the cis volume and 1.5M CsCl in the trans volume using the membrane indicated above.

The 109 bp dsDNA fragments were generated by PCR amplification reaction using Taq polymerase according to the manufacturer's specifications (Biotium, Cat. #31014). The amplification was performed for differing numbers of cycles to provide samples with varied dsDNA concentration. Here, dsDNA samples were collected after 20 cycles, 25 cycles, 30 cycles, 35 cycles, and 40 cycles of amplification to observe the change in capture rate under these conditions at different concentrations. Following amplification, the dsDNA fragments were cleaned and purified using a DNA cleanup kit (New England BioLabs, Cat. #T1030S).

We added a sample containing 109 bp dsDNA to the cis volume and applied a voltage of 100 mV or 150 mV across the nanopore for each of the collected samples. The signal was collected and analyzed as described in Example 14.

FIG. 12 shows data from a 3M/1.5M CsCl gradient sensing solution with a using a 25 nm nanopore for a 109 bp dsDNA amplicon at different concentrations (i.e., after 20 cycles, 25 cycles, 30 cycles, 35 cycles, and 40 cycles of amplification).

Next, we tested a 32 nm solid-state nanopore comprising 3M CsCl in the cis volume and 1.5M CsCl in the trans volume using the membrane indicated above.

FIG. 13 shows data from a with a 3M/1.5M CsCl gradient sensing solution with a 32 nm nanopore for a 109 bp dsDNA amplicon at different concentrations (i.e., after 20 cycles, 25 cycles, 30 cycles, 35 cycles, and 40 cycles of amplification).

Conclusion: We observed that a 109 bp dsDNA sample could be easily detected even at a lower concentration (20 amplification cycles) using a CsCl gradient 3M/1.5M sensing solution with either a 25 nm or a 32 nm nanopore.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. In addition, section headings, the materials, methods, and examples are illustrative only and not intended to be limiting.

6. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

7. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification

What is claimed is:

1. A method for detecting or characterization of a polynucleotide in a sample within a nanopore device comprising:
   a. contacting a sample suspected of comprising a polynucleotide with a sensing solution comprising an effective amount of a polyether agent of Formula (I):

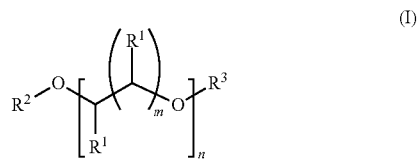

wherein:
m is 1-3;
n is 1-30;
each $R^1$ is independently H or methyl; and
$R^2$ and $R^3$ are each independently H or $C_{(1-6)}$alkyl,
wherein the sensing solution is contacting a nanoporous membrane of a nanopore device, wherein the nanoporous membrane separates the space of the nanopore device into a cis volume and a trans volume;
b. applying a voltage across a nanopore of the nanoporous membrane thereby inducing translocation of the polynucleotide through the nanoporous membrane; and
c. detecting a current during the translocation of the polynucleotide in the nanopore device; and
(d) characterizing the polynucleotide as having a length of less than 500 base pairs (bps), wherein the nanopore device containing the sensing solution allows for discrimination of the polynucleotide by size.

2. The method of claim 1, wherein the polyether agent is of Formula (Ia):

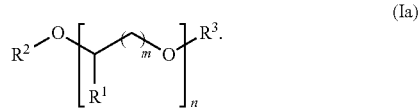

3. The method of claim 1, wherein the polyether agent is of Formula (II):

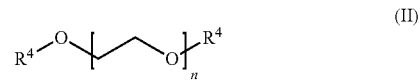

wherein each $R^4$ is H or methyl.

4. The method of claim 3, wherein n is either 1, 3, or 4, and each $R^4$ is H or is methyl.

5. The method of claim 1, wherein the polyether agent is of Formula (III), (IIIa) or (IIIb):

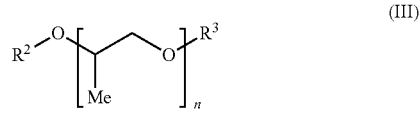

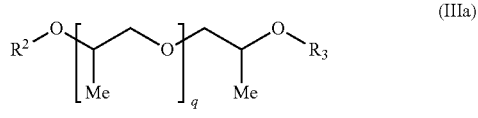

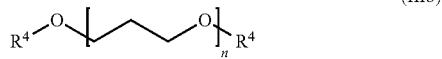

wherein:
n is 1-30;
q is 1-29;
$R^2$, $R^3$ and each $R^4$ are each independently H or methyl.

6. The method of claim 1, wherein the sensing solution further comprises a salt, wherein the salt is a monovalent or divalent salt, and wherein the salt is selected from a group consisting of: LiCl, NaCl, $MgCl_2$, CsCl, $CaCl_2$, Li, Na, K, Mg, Cs, Ca, or a combination thereof, and is at a molar concentration of greater than 0.01M, 0.02M, 0.05M, 0.1M, 0.2M, 0.5M, 1M, 2M, 3M, 4M or 5M.

7. The method of claim 6, wherein the salt is not KCl.

8. The method of claim 1, further comprising a buffer solution selected from a group consisting of: Tris-HCl, Borate, CHES, Bis-tris propane, or CAPS, and wherein the buffer solution is at a concentration of at least 10 mM.

9. The method of claim 1, further comprising a chelating agent, wherein the chelating agent is EDTA, EGTA or a combination thereof.

10. The method of claim 1, wherein the effective amount is v/v 1%, 2%, 3%, 4% 5%, 6%, 7%, 8%, 9%, 10%, 11%, 12%, 13%, 14%, 15% or more.

11. The method of claim 1, wherein the n is at least 3-4, or at least 4-5, at least 5-8, or at least 8-10, or at least 10-20, or at least 20-30.

12. The method of claim 1, wherein characterizing further comprises discrimination of different lengths or sizes of the polynucleotide in the sample.

13. The method of claim 12, wherein the different lengths or sizes of the polynucleotide in the sample is less than 300 bs, less than 200 bp, less than 100 bp, or less than 50 bp.

14. The method of claim 12, wherein the discrimination is between a ssDNA, a dsDNA, a dsRNA, a RNA, a RNA/DNA hybrid, a PNA/DNA hybrid, or a RNA/PNA hybrid with length differences of less than 50 bp, 100 bp, 200 bp, 300 bp, or 400 bp.

15. The method of claim 1, wherein characterizing further comprises one or more of: a quantity of the polynucleotide, a modification of the polynucleotide, a structure of the polynucleotide, a sequence of the polynucleotide, and a concentration of the polynucleotide.

16. The method of claim 1, wherein the nanoporous membrane comprises a pore made from a solid state substrate or from a biological substrate.

17. The method of claim 1, wherein the nanoporous membrane has a pore with a minimum diameter of greater than 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm, or 65 nm.

18. The method of claim 1, wherein the nanoporous membrane has a pore with a minimum diameter of less than 70 nm, 75 nm, 80 nm, 85 nm, 90 nm, 95 nm, 100 nm, 105 nm, or 110 nm.

19. The method of claim 1, wherein the nanoporous membrane has a pore with diameter of 20 nm to 60 nm.

20. The method of claim 1, wherein the accuracy of the characterization is improved as compared to the same method performed in a standard running buffer.

21. The method of claim 1, wherein the characterization has improved accuracy as compared to characterization from the same method performed in a standard buffer.

22. The method of claim 21, wherein the standard buffer comprises LiCl, KCl, NaCl or a monovalent ion thereof.

23. The method of claim 21, wherein the standard buffer comprises LiCl, KCl, or NaCl or a monovalent ion thereof and does not contain a polyether agent of Formula (I), (II), (III), (IV), or a combination therefore.

24. The method of claim 1, wherein the cis volume and the trans volume comprise the same sensing solution.

25. The method of claim 1, wherein the cis volume and the trans volume comprise a sensing solution that are different.

26. The method of claim 1, wherein the cis volume comprises the sensing solution, and the trans volume comprises at least a 10% carbohydrate solution.

27. The method of claim 1, wherein the cis volume comprises a 10% carbohydrate solution and the trans volume comprises a sensing solution of any one of claim 1.

28. The method of claim 1, wherein the nanopore device comprises electrodes for applying a voltage across the nanopore and for monitoring the current.

29. The method of claim 1, wherein the cis volume and trans volume are in fluidic communication through the pore.

30. The method of claim 1, wherein the contacting step further comprises a probe comprising a residue conjugated to a voltage-sensitive moiety, that binds to the polynucleotide.

31. The method of claim 1, wherein the current is an ionic current.

32. The method of claim 1, wherein the current is a tunneling current.

33. The method of claim 1, wherein the polynucleotide is a double-stranded polynucleotide.

34. A nanopore device for detecting or characterizing a polynucleotide in a sample when mixed with a sensing solution, comprising:
   a. a nanopore formed within a nanoporous membrane;
   b. the nanoporous membrane, wherein the nanoporous membrane separates an interior space of the nanopore device into a cis volume and a trans volume;
   c. a sensor comprising a set of electrodes for applying a voltage across the nanopore and for monitoring an ionic current through the nanopore;
   d. a sensing solution within the nanoporous membrane comprising an effective amount of a polyether agent of Formula (I):

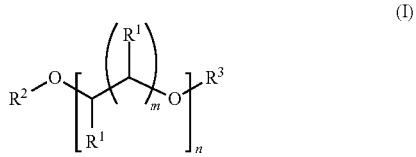

(I)

wherein:
   m is 1-3;
   n is 1-30;
   each $R^1$ is independently H or methyl; and
   $R^2$ and $R^3$ are each independently H or $C_{(1-6)}$alkyl,
   wherein the sensor is configured to measure ionic current across the nanopore, and characterize the polynucleotide within the sensing solution as having a length of less than 500 base pairs (bps) as the polynucleotide translocates through the nanopore under the applied voltage, wherein the nanopore device containing the sensing solution allows for discrimination of the polynucleotide by size.

35. The device of claim 34, wherein the cis volume and the trans volume each comprise the same sensing solution.

36. The device of claim 34, wherein the cis volume and the trans volume each comprise a different sensing solution.

37. The device of claim 34, wherein the device further comprises a voltage-clamped amplifier.

38. The device of claim 34, wherein device is a biological nanopore device.

39. The device of claim 34, wherein device is a solid-state nanopore device.

40. The device of claim 34, wherein device is a hybrid nanopore device.

41. A system for detecting or characterizing a polynucleotide in a sample comprising:
   a. a sensing solution and a nanopore device, wherein the sensing solution comprises:
      an effective amount of a polyether agent of Formula (I):

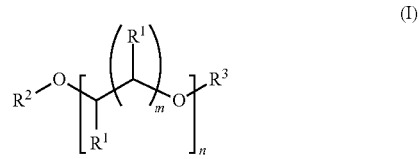

(I)

wherein:
   m is 1-3;
   n is 1-30;
   each $R^1$ is independently H or methyl; and
   $R^2$ and $R^3$ are each independently H or $C_{(1-6)}$alkyl,
   and wherein the nanopore device comprises a nanopore formed within a nanoporous membrane, wherein the nanoporous membrane separates the space of the nanopore device into a cis volume and a trans volume;
   b. a sensor for detecting a current from a polynucleotide in the nanopore device;
   c. a processor; and
   d. a computer readable medium for storing code that detects translocation of the polynucleotide through the nanopore device when executed by the processor, wherein the code further stores an algorithm that identifies one or more current signatures, that when executed by the processor, causes the processor to characterize the polynucleotide as having a length of less than 500 base pairs (bps) as the polynucleotide translocates through the nanopore of the nanopore device under the applied voltage, wherein the nanopore device containing the sensing solution allows for discrimination of the polynucleotide by size.

42. A kit for detection or characterization of a polynucleotide in a sample using a nanopore device comprising:
   a. a sensing solution and a nanopore device, wherein the sensing solution comprises:
      an effective amount of a polyether agent of Formula (I):

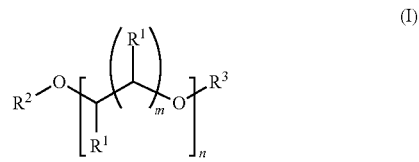

(I)

wherein:
   m is 1-3;
   n is 1-30;
   each $R^1$ is independently H or methyl; and
   $R^2$ and $R^3$ are each independently H or $C_{(1-6)}$alkyl,
   and wherein the nanopore device comprises a nanoporous membrane, wherein the nanoporous membrane separates the space of the nanopore device into a cis volume and a trans volume; and
   b. instructions for using the sensing solution with the nanopore device to detect or characterize the polynucleotide in the sample.

* * * * *